United States Patent
Gudas et al.

(10) Patent No.: US 11,266,745 B2
(45) Date of Patent: Mar. 8, 2022

(54) EXTENSION SEQUENCES FOR DIABODIES

(71) Applicant: ImaginAb, Inc., Inglewood, CA (US)

(72) Inventors: Jean Marie Gudas, Los Angeles, CA (US); Daulet Kadyl Satpayev, Redwood City, CA (US); Tove Olafsen, Reseda, CA (US); Alessandro Mascioni, Los Angeles, CA (US); Michael Yuri Torgov, Hawthorne, CA (US)

(73) Assignee: ImaginAb, Inc., Inglewood, CA (US)

( * ) Notice: Subject to any disclaimer, the term of this patent is extended or adjusted under 35 U.S.C. 154(b) by 703 days.

(21) Appl. No.: 15/866,870

(22) Filed: Jan. 10, 2018

(65) Prior Publication Data
US 2018/0221507 A1 Aug. 9, 2018

Related U.S. Application Data

(60) Provisional application No. 62/456,252, filed on Feb. 8, 2017.

(51) Int. Cl.
| | |
|---|---|
| *A61K 47/68* | (2017.01) |
| *A61K 39/395* | (2006.01) |
| *A61K 47/54* | (2017.01) |
| *C07K 16/18* | (2006.01) |
| *C07K 16/46* | (2006.01) |
| *G01N 21/00* | (2006.01) |
| *A61K 51/10* | (2006.01) |
| *C07K 16/28* | (2006.01) |
| *C07K 16/32* | (2006.01) |
| *C07K 16/30* | (2006.01) |
| *A61K 39/00* | (2006.01) |

(52) U.S. Cl.
CPC .... *A61K 47/6879* (2017.08); *A61K 39/39558* (2013.01); *A61K 47/555* (2017.08); *A61K 47/6803* (2017.08); *A61K 47/6851* (2017.08); *A61K 47/6877* (2017.08); *A61K 47/6891* (2017.08); *A61K 51/1051* (2013.01); *A61K 51/1093* (2013.01); *C07K 16/18* (2013.01); *C07K 16/2809* (2013.01); *C07K 16/2815* (2013.01); *C07K 16/3069* (2013.01); *C07K 16/32* (2013.01); *C07K 16/46* (2013.01); *G01N 21/00* (2013.01); *A61K 2039/505* (2013.01); *A61K 2039/507* (2013.01); *C07K 2317/565* (2013.01); *C07K 2317/567* (2013.01); *C07K 2317/60* (2013.01); *C07K 2317/622* (2013.01); *C07K 2317/626* (2013.01); *C07K 2317/73* (2013.01); *C07K 2317/90* (2013.01)

(58) Field of Classification Search
None
See application file for complete search history.

(56) References Cited

U.S. PATENT DOCUMENTS

| | | |
|---|---|---|
| 4,281,061 A | 7/1981 | Zuk et al. |
| 4,709,015 A | 11/1987 | Kung et al. |
| 4,892,824 A | 1/1990 | Skaletsky |
| 4,943,525 A | 7/1990 | Dawson |
| 4,946,778 A | 8/1990 | Ladner et al. |
| 5,256,395 A | 10/1993 | Barbet et al. |
| 5,332,567 A | 7/1994 | Goldenberg |
| 5,376,249 A | 12/1994 | Afeyan et al. |
| 5,518,889 A | 5/1996 | Lander et al. |
| 5,521,297 A | 5/1996 | Daggett et al. |
| 5,523,210 A | 6/1996 | Paulus |
| 5,534,254 A | 7/1996 | Huston et al. |
| 5,538,866 A | 7/1996 | Israeli et al. |
| 5,582,996 A | 12/1996 | Curtis |
| 5,591,828 A | 1/1997 | Bosslet et al. |
| 5,601,819 A | 2/1997 | Wong et al. |
| 5,627,078 A | 5/1997 | Karl et al. |
| 5,637,481 A | 6/1997 | Ledbetter et al. |
| 5,688,690 A | 11/1997 | Valiante et al. |
| 5,693,477 A | 12/1997 | Cornell et al. |
| 5,705,614 A | 1/1998 | Ring |
| 5,712,136 A | 1/1998 | Wickham et al. |
| 5,747,035 A | 5/1998 | Presta et al. |
| 5,762,930 A | 6/1998 | Fanger et al. |
| 5,807,689 A | 9/1998 | Daggett et al. |
| 5,821,333 A | 10/1998 | Carter et al. |
| 5,830,473 A | 11/1998 | Thierfelder |
| 5,830,478 A | 11/1998 | Raso et al. |
| 5,837,242 A | 11/1998 | Holliger et al. |
| 5,837,821 A | 11/1998 | Wu |
| 5,840,854 A | 11/1998 | Hellstrom et al. |
| 5,844,094 A | 12/1998 | Hudson et al. |
| 5,851,527 A | 12/1998 | Hudson et al. |
| 5,852,186 A | 12/1998 | Sodroski et al. |
| 5,859,205 A | 1/1999 | Adair |

(Continued)

FOREIGN PATENT DOCUMENTS

| | | |
|---|---|---|
| CA | 2903587 | 9/2014 |
| CN | 1356341 | 7/2002 |

(Continued)

OTHER PUBLICATIONS

US 8,748,586 B2, 06/2014, Ho et al. (withdrawn)

(Continued)

*Primary Examiner* — Meera Natarajan
(74) *Attorney, Agent, or Firm* — Knobbe, Martens, Olson & Bear, LLP

(57) ABSTRACT

Provided herein are diabodies that comprise extension sequences and antigen binding constructs that comprise extension sequences.

25 Claims, 27 Drawing Sheets

Specification includes a Sequence Listing.

(56) References Cited

U.S. PATENT DOCUMENTS

| | | |
|---|---|---|
| 5,861,156 A | 1/1999 | George et al. |
| 5,863,765 A | 1/1999 | Berry et al. |
| 5,869,049 A | 2/1999 | Noelle et al. |
| 5,869,053 A | 2/1999 | Stern et al. |
| 5,869,620 A | 2/1999 | Whitlow et al. |
| 5,876,691 A | 3/1999 | Chester et al. |
| 5,877,291 A | 3/1999 | Mezes et al. |
| 5,912,122 A | 6/1999 | Daggett et al. |
| 5,932,448 A | 8/1999 | Tso et al. |
| 5,935,818 A | 8/1999 | Israeli et al. |
| 5,942,229 A | 8/1999 | Noelle et al. |
| 5,951,982 A | 9/1999 | Zöller et al. |
| 5,959,083 A | 9/1999 | Bosslet et al. |
| 5,977,322 A | 11/1999 | Marks et al. |
| 5,980,896 A | 11/1999 | Hellstrom et al. |
| 5,989,830 A | 11/1999 | Davis et al. |
| 5,990,275 A | 11/1999 | Whitlow et al. |
| 6,001,581 A | 12/1999 | Johnson et al. |
| 6,010,902 A | 1/2000 | Ledbetter et al. |
| 6,030,792 A | 2/2000 | Otterness et al. |
| 6,051,688 A | 4/2000 | Stormann et al. |
| 6,071,490 A | 6/2000 | Griffiths et al. |
| 6,077,675 A | 6/2000 | Stormann et al. |
| 6,083,763 A | 7/2000 | Balch |
| 6,084,084 A | 7/2000 | Stormann et al. |
| 6,096,871 A | 8/2000 | Presta et al. |
| 6,099,841 A | 8/2000 | Hillan et al. |
| 6,103,524 A | 8/2000 | Belagaje et al. |
| 6,107,090 A | 8/2000 | Bander |
| 6,121,022 A | 9/2000 | Presta et al. |
| 6,136,311 A | 10/2000 | Bander |
| 6,150,508 A | 11/2000 | Murphy et al. |
| 6,193,966 B1 | 2/2001 | Deo et al. |
| 6,197,298 B1 | 3/2001 | Chang |
| 6,200,765 B1 | 3/2001 | Murphy et al. |
| 6,201,167 B1 | 3/2001 | Pothier |
| 6,221,609 B1 | 4/2001 | Belagaje et al. |
| 6,228,610 B1 | 5/2001 | Flor et al. |
| 6,241,961 B1 | 6/2001 | Benes et al. |
| 6,248,516 B1 | 6/2001 | Winter et al. |
| 6,284,742 B1 | 9/2001 | Curiel et al. |
| 6,294,391 B1 | 9/2001 | Badley et al. |
| 6,312,694 B1 | 11/2001 | Thorpe et al. |
| 6,329,503 B1 | 12/2001 | Afar et al. |
| 6,342,587 B1 | 1/2002 | Barbas, III et al. |
| 6,361,774 B1 | 3/2002 | Griffiths et al. |
| 6,362,316 B1 | 3/2002 | Daggett et al. |
| 6,368,596 B1 | 4/2002 | Ghetie et al. |
| 6,383,759 B1 | 5/2002 | Murphy et al. |
| 6,384,205 B1 | 5/2002 | Belagaje et al. |
| 6,387,350 B2 | 5/2002 | Goldenberg |
| 6,399,068 B1 | 6/2002 | Goldenberg |
| 6,413,764 B1 | 7/2002 | Daggett et al. |
| 6,458,933 B1 | 10/2002 | Hansen |
| 6,485,919 B1 | 11/2002 | Daggett et al. |
| 6,491,916 B1 | 12/2002 | Bluestone et al. |
| 6,492,123 B1 | 12/2002 | Hollinger et al. |
| 6,515,107 B2 | 2/2003 | Flor et al. |
| 6,569,432 B1 | 5/2003 | Israeli et al. |
| 6,602,684 B1 | 8/2003 | Umana et al. |
| 6,608,176 B2 | 8/2003 | Chaudhari et al. |
| 6,642,356 B1 | 11/2003 | Humphreys |
| 6,649,163 B1 | 11/2003 | Bander |
| 6,709,844 B1 | 3/2004 | Levy |
| 6,767,711 B2 | 7/2004 | Bander |
| 6,770,450 B1 | 8/2004 | Bander |
| 6,824,780 B1 | 11/2004 | Devaux et al. |
| 6,833,438 B1 | 12/2004 | Afar et al. |
| 6,835,866 B1 | 12/2004 | Mangelsdorf et al. |
| 6,861,234 B1 | 3/2005 | Simard et al. |
| 6,869,620 B2 | 3/2005 | Moore |
| 6,870,034 B2 | 3/2005 | Breece et al. |
| 6,887,975 B2 | 5/2005 | Afar et al. |
| 6,953,668 B1 | 10/2005 | Israeli et al. |
| 6,977,074 B2 | 12/2005 | Kundig et al. |
| 6,994,851 B1 | 2/2006 | Kundig et al. |
| 7,037,647 B1 | 5/2006 | Israeli et al. |
| 7,045,605 B2 | 5/2006 | Bander et al. |
| 7,053,186 B2 | 5/2006 | Afar et al. |
| 7,070,782 B1 | 7/2006 | Israeli et al. |
| 7,105,159 B1 | 9/2006 | Israeli et al. |
| 7,112,412 B1 | 9/2006 | Bander |
| 7,157,250 B2 | 1/2007 | San Gabriel et al. |
| 7,163,680 B2 | 1/2007 | Bander |
| 7,166,714 B2 | 1/2007 | Afar et al. |
| 7,192,586 B2 | 3/2007 | Bander |
| 7,232,682 B2 | 6/2007 | Simard et al. |
| 7,235,641 B2 | 6/2007 | Kufer et al. |
| 7,253,257 B2 | 8/2007 | Flor et al. |
| 7,258,971 B2 | 8/2007 | Karicheti et al. |
| 7,262,280 B1 | 8/2007 | Stormann et al. |
| 7,319,006 B2 | 1/2008 | Afar et al. |
| 7,323,553 B2 | 1/2008 | Fahrner et al. |
| 7,335,760 B2 | 2/2008 | Alexandrov et al. |
| 7,364,729 B2 | 4/2008 | Kundig et al. |
| 7,375,078 B2 | 5/2008 | Feng |
| 7,390,654 B2 | 6/2008 | Levy |
| 7,399,461 B2 | 7/2008 | Heston et al. |
| 7,435,416 B2 | 10/2008 | Devaux et al. |
| 7,446,190 B2 | 11/2008 | Sadelain et al. |
| 7,452,539 B2 | 11/2008 | Emery et al. |
| 7,455,991 B2 | 11/2008 | Afar et al. |
| 7,485,299 B2 | 2/2009 | Afar et al. |
| 7,485,704 B2 | 2/2009 | Fahrner et al. |
| 7,494,646 B2 | 2/2009 | Jakobovits et al. |
| 7,498,298 B2 | 3/2009 | Doronina et al. |
| 7,514,078 B2 | 4/2009 | Bander et al. |
| 7,517,670 B2 | 4/2009 | Umana et al. |
| 7,521,541 B2 | 4/2009 | Eigenbrot et al. |
| 7,524,813 B2 | 4/2009 | Zundel et al. |
| 7,541,441 B2 | 6/2009 | Rosen et al. |
| 7,569,389 B2 | 8/2009 | Feldmann et al. |
| 7,575,749 B2 | 8/2009 | Afar et al. |
| 7,595,379 B2 | 9/2009 | Gudas et al. |
| 7,611,904 B2 | 11/2009 | Afar et al. |
| 7,612,181 B2 | 11/2009 | Wu et al. |
| 7,622,569 B2 | 11/2009 | Raitano et al. |
| 7,642,054 B2 | 1/2010 | Afar et al. |
| 7,662,936 B2 | 2/2010 | Kadkhodayan et al. |
| 7,666,414 B2 | 2/2010 | Bander |
| 7,666,425 B1 | 2/2010 | Bander |
| 7,678,371 B2 | 3/2010 | Lugovskoy et al. |
| 7,727,533 B2 | 6/2010 | Afar et al. |
| 7,745,394 B2 | 6/2010 | Doronina et al. |
| 7,754,681 B2 | 7/2010 | Feng |
| 7,785,801 B2 | 8/2010 | Tureci et al. |
| 7,790,850 B2 | 9/2010 | Kobilka et al. |
| 7,807,799 B2 | 10/2010 | Fahrner et al. |
| 7,820,166 B2 | 10/2010 | Lanzavecchia |
| 7,834,146 B2 | 11/2010 | Kovalic et al. |
| 7,838,637 B2 | 11/2010 | Kontermann et al. |
| 7,855,275 B2 | 12/2010 | Eigenbrot et al. |
| 7,867,483 B2 | 1/2011 | Delcayre et al. |
| 7,884,179 B2 | 2/2011 | Faris et al. |
| 7,888,035 B2 | 2/2011 | Klass et al. |
| 7,897,356 B2 | 3/2011 | Klass et al. |
| 7,906,329 B2 | 3/2011 | Umana et al. |
| 7,928,201 B2 | 4/2011 | Afar et al. |
| 7,939,503 B2 | 5/2011 | Jakobovits et al. |
| 7,947,276 B2 | 5/2011 | Jakobovits et al. |
| 7,947,459 B2 | 5/2011 | Hubert et al. |
| 7,947,839 B2 | 5/2011 | Gazzard et al. |
| 7,960,109 B2 | 6/2011 | Hessels et al. |
| 7,964,566 B2 | 6/2011 | Doronina et al. |
| 7,964,567 B2 | 6/2011 | Doronina et al. |
| 7,968,307 B2 | 6/2011 | Afar et al. |
| 7,989,434 B2 | 8/2011 | Feng |
| 7,993,626 B2 | 8/2011 | McBride et al. |
| 7,994,135 B2 | 8/2011 | Doronina et al. |
| 7,998,701 B2 | 8/2011 | Chua et al. |
| 8,007,994 B2 | 8/2011 | Mangelsdorf et al. |
| 8,008,442 B2 | 8/2011 | Jakobovits et al. |
| 8,012,937 B2 | 9/2011 | Raitano et al. |
| 8,013,128 B2 | 9/2011 | Gudas et al. |

(56) References Cited

U.S. PATENT DOCUMENTS

| | | |
|---|---|---|
| 8,013,135 B2 | 9/2011 | Jakobovits et al. |
| 8,043,830 B2 | 10/2011 | Barat et al. |
| 8,071,742 B2 | 12/2011 | Kobilka et al. |
| 8,106,174 B2 | 1/2012 | Kovalic et al. |
| 8,139,715 B2 | 3/2012 | Kobilka et al. |
| 8,178,655 B2 | 5/2012 | Kobilka et al. |
| 8,206,932 B2 | 6/2012 | Gudas et al. |
| 8,260,596 B2 | 9/2012 | Kobilka et al. |
| 8,278,424 B2 | 10/2012 | Gudas et al. |
| 8,329,432 B2 | 12/2012 | Kobilka et al. |
| 8,383,778 B2 | 2/2013 | Hsieh et al. |
| 8,470,561 B2 | 6/2013 | Kobilka |
| 8,487,077 B2 | 7/2013 | Olma et al. |
| 8,586,006 B2 | 11/2013 | Hood et al. |
| 8,637,639 B2 | 1/2014 | Kobilka et al. |
| 8,680,237 B2 | 3/2014 | Strome et al. |
| 8,728,738 B2 | 5/2014 | Broet et al. |
| 8,772,459 B2 | 7/2014 | Ho et al. |
| 8,795,977 B2 | 8/2014 | Wieland |
| 8,889,377 B2 | 11/2014 | Kobilka |
| 8,940,298 B2 | 1/2015 | Wu et al. |
| 8,940,871 B2 | 1/2015 | Wu et al. |
| 8,951,737 B2 | 2/2015 | Bander et al. |
| 8,999,654 B2 | 4/2015 | Gaitanaris et al. |
| 9,045,561 B2 | 6/2015 | Kobilka |
| 9,255,131 B2 | 2/2016 | Türeci et al. |
| 9,334,324 B2 | 5/2016 | Choo et al. |
| 9,512,208 B2 | 12/2016 | Strome et al. |
| 9,512,210 B2 | 12/2016 | Strome et al. |
| 9,540,438 B2 | 1/2017 | Barfield et al. |
| 9,701,754 B1 | 7/2017 | Wu et al. |
| 9,765,155 B2 | 9/2017 | Wu et al. |
| 10,301,389 B2 | 5/2019 | Ho et al. |
| 10,377,826 B2 | 8/2019 | Ho et al. |
| 10,414,820 B2 | 9/2019 | Ho et al. |
| 2002/0004215 A1 | 1/2002 | Osbourn et al. |
| 2002/0018749 A1 | 2/2002 | Hudson et al. |
| 2002/0037289 A1 | 3/2002 | Thorpe et al. |
| 2002/0119096 A1 | 8/2002 | Griffiths |
| 2002/0119153 A1 | 8/2002 | Thorpe et al. |
| 2002/0151052 A1 | 8/2002 | Chaudhari et al. |
| 2002/0122798 A1 | 9/2002 | Young |
| 2002/0127638 A1 | 9/2002 | Flor et al. |
| 2002/0132979 A1 | 9/2002 | Chen |
| 2002/0136689 A1 | 9/2002 | Reiter et al. |
| 2003/0113868 A1 | 6/2003 | Flor et al. |
| 2003/0118583 A1 | 6/2003 | Emery et al. |
| 2003/0143668 A1 | 7/2003 | Suwa et al. |
| 2003/0170228 A1 | 9/2003 | Ashkenazi et al. |
| 2003/0175900 A1 | 9/2003 | Ashkenazi et al. |
| 2003/0211096 A1 | 11/2003 | Ashkenazi et al. |
| 2003/0235833 A1 | 12/2003 | Suwa et al. |
| 2004/0018519 A1 | 1/2004 | Wright |
| 2004/0033511 A1 | 2/2004 | Pfizenmaier et al. |
| 2004/0038339 A1 | 2/2004 | Kufer et al. |
| 2004/0071690 A1 | 4/2004 | Hudson et al. |
| 2004/0162411 A1 | 8/2004 | Lanzavecchia |
| 2004/0172684 A1 | 9/2004 | Kovalic et al. |
| 2004/0197825 A1 | 10/2004 | Karicheti et al. |
| 2004/0214272 A1 | 10/2004 | La Rosa et al. |
| 2004/0241817 A1 | 12/2004 | Umana et al. |
| 2005/0003481 A1 | 1/2005 | Gabriel et al. |
| 2005/0026178 A1 | 2/2005 | Nilsen-Hamilton |
| 2005/0136050 A1 | 6/2005 | Kufer et al. |
| 2005/0175618 A1 | 8/2005 | Carroll et al. |
| 2005/0176028 A1 | 8/2005 | Hofmeister et al. |
| 2005/0215769 A1 | 9/2005 | Breece et al. |
| 2005/0232929 A1 | 10/2005 | Kadkhodayan et al. |
| 2005/0244333 A1 | 11/2005 | Yazaki et al. |
| 2005/0272128 A1 | 12/2005 | Umana et al. |
| 2006/0002933 A1 | 1/2006 | Bluestone et al. |
| 2006/0062793 A1 | 3/2006 | Webb et al. |
| 2006/0099582 A1 | 5/2006 | Papadopoulos |
| 2006/0134105 A1 | 6/2006 | Lazar et al. |
| 2006/0134109 A1 | 6/2006 | Gaitanaris et al. |
| 2006/0150283 A1 | 7/2006 | Alexandrov et al. |
| 2006/0159689 A1 | 7/2006 | Chiang et al. |
| 2006/0234226 A1 | 10/2006 | Fahrner et al. |
| 2006/0234271 A1 | 10/2006 | Su |
| 2006/0235212 A1 | 10/2006 | Alexandrov et al. |
| 2006/0235213 A1 | 10/2006 | Alexandrov et al. |
| 2006/0269540 A1 | 11/2006 | Robert et al. |
| 2006/0275312 A1 | 12/2006 | Chua et al. |
| 2007/0009916 A1 | 1/2007 | Suwa et al. |
| 2007/0039067 A1 | 2/2007 | Feldmann et al. |
| 2007/0059306 A1 | 3/2007 | Grosmaire |
| 2007/0081993 A1 | 4/2007 | Kufer |
| 2007/0134243 A1 | 6/2007 | Gazzard et al. |
| 2007/0212331 A1 | 9/2007 | Baldassare et al. |
| 2007/0214517 A1 | 9/2007 | Alexandrov et al. |
| 2007/0243950 A1 | 10/2007 | Billings |
| 2007/0253950 A1 | 11/2007 | Jacobsen |
| 2007/0271633 A9 | 11/2007 | Kovalic et al. |
| 2007/0286858 A1 | 12/2007 | Clancy |
| 2008/0095770 A1 | 4/2008 | Umana |
| 2008/0152586 A1 | 6/2008 | Hudson et al. |
| 2008/0171040 A1 | 7/2008 | Ebens et al. |
| 2008/0193454 A1 | 8/2008 | Tureci et al. |
| 2008/0206192 A1 | 8/2008 | Moller et al. |
| 2008/0213256 A1 | 9/2008 | Kufer et al. |
| 2008/0213921 A1 | 9/2008 | Robertson et al. |
| 2008/0227736 A1 | 9/2008 | Chen et al. |
| 2008/0260744 A1 | 10/2008 | Gaitanaris et al. |
| 2008/0267872 A1 | 10/2008 | Raitano et al. |
| 2008/0269471 A1 | 10/2008 | Alexandrov et al. |
| 2008/0279850 A1 | 11/2008 | Brady et al. |
| 2008/0305105 A1 | 12/2008 | Kufer et al. |
| 2008/0305476 A1 | 12/2008 | Robertson et al. |
| 2009/0004109 A1 | 1/2009 | Jacobovits et al. |
| 2009/0022738 A1 | 1/2009 | Hofmeister et al. |
| 2009/0041758 A1 | 2/2009 | Glaser |
| 2009/0041791 A1 | 2/2009 | Feng |
| 2009/0053223 A1 | 2/2009 | Hoffmann et al. |
| 2009/0087878 A9 | 4/2009 | La Rosa et al. |
| 2009/0099344 A1 | 4/2009 | Fahrner et al. |
| 2009/0118474 A1 | 5/2009 | Kobilka et al. |
| 2009/0136475 A1 | 5/2009 | Barth |
| 2009/0155290 A1 | 6/2009 | Carroll et al. |
| 2009/0178153 A1 | 7/2009 | Gaitanaris et al. |
| 2009/0202548 A1 | 8/2009 | Gudas et al. |
| 2009/0214539 A1 | 8/2009 | Grosmaire |
| 2009/0144848 A1 | 9/2009 | Kovalic et al. |
| 2009/0226465 A1 | 9/2009 | Jackson |
| 2009/0238755 A1 | 9/2009 | Bander |
| 2009/0252729 A1 | 10/2009 | Farrington et al. |
| 2009/0252748 A1 | 10/2009 | Mi et al. |
| 2009/0272169 A1 | 11/2009 | Pan |
| 2009/0275081 A1 | 11/2009 | Barat et al. |
| 2009/0280120 A1 | 11/2009 | Bander et al. |
| 2009/0286258 A1 | 11/2009 | Kaur et al. |
| 2009/0311181 A1 | 12/2009 | Wu et al. |
| 2010/0003766 A1 | 1/2010 | Eigenbrot et al. |
| 2010/0034837 A1 | 2/2010 | Beria et al. |
| 2010/0047239 A1 | 2/2010 | Wu et al. |
| 2010/0058803 A1 | 3/2010 | Ransbarger |
| 2010/0069616 A1 | 3/2010 | Wu et al. |
| 2010/0083407 A1 | 4/2010 | Feldmann et al. |
| 2010/0111856 A1 | 5/2010 | Gill et al. |
| 2010/0111959 A1 | 5/2010 | Swanson et al. |
| 2010/0135900 A1 | 6/2010 | Cerveny |
| 2010/0184046 A1 | 7/2010 | Klass et al. |
| 2010/0189651 A1 | 7/2010 | Stagliano |
| 2010/0209343 A1 | 8/2010 | Bander et al. |
| 2010/0215581 A1 | 8/2010 | Hoffmann |
| 2010/0239633 A1 | 9/2010 | Strome et al. |
| 2010/0255479 A1 | 10/2010 | Mikolajczyk et al. |
| 2010/0266491 A1 | 10/2010 | Farokhzad et al. |
| 2010/0267933 A1 | 10/2010 | Wilson |
| 2010/0278919 A1 | 11/2010 | Denes et al. |
| 2010/0297004 A1 | 11/2010 | Wu et al. |
| 2010/0298542 A1 | 11/2010 | Igawa et al. |
| 2010/0303715 A1 | 12/2010 | Israeli |
| 2010/0303814 A1 | 12/2010 | Cizeau et al. |
| 2010/0303821 A1 | 12/2010 | Ashman |

(56) References Cited

U.S. PATENT DOCUMENTS

| | | |
|---|---|---|
| 2010/0310452 A1 | 12/2010 | Israeli |
| 2010/0310584 A1 | 12/2010 | Carroll et al. |
| 2011/0006466 A1 | 1/2011 | Ichikawa |
| 2011/0009001 A1 | 1/2011 | Chen |
| 2011/0009603 A1 | 1/2011 | Kobilka et al. |
| 2011/0014628 A1 | 1/2011 | Tureci et al. |
| 2011/0020327 A1 | 1/2011 | Moya et al. |
| 2011/0054151 A1 | 3/2011 | Lazar et al. |
| 2011/0069019 A1 | 3/2011 | Carpendale et al. |
| 2011/0076287 A1 | 3/2011 | Cohen et al. |
| 2011/0081345 A1 | 4/2011 | Moore |
| 2011/0086050 A1 | 4/2011 | Presta |
| 2011/0104059 A1 | 5/2011 | St. Croix et al. |
| 2011/0110852 A1 | 5/2011 | Miller et al. |
| 2011/0110854 A1 | 5/2011 | McBride et al. |
| 2011/0117023 A1 | 5/2011 | Yamauchi |
| 2011/0123532 A1 | 5/2011 | Gurney et al. |
| 2011/0137017 A1 | 6/2011 | Eigenbrot et al. |
| 2011/0164731 A1 | 7/2011 | Kobilka et al. |
| 2011/0171728 A1 | 7/2011 | Kobilka et al. |
| 2011/0185439 A1 | 7/2011 | Gaitanaris et al. |
| 2011/0189756 A1 | 8/2011 | Kobilka et al. |
| 2011/0207155 A1 | 8/2011 | Pengo et al. |
| 2011/0214189 A1 | 9/2011 | Gaitanaris et al. |
| 2011/0227023 A1 | 9/2011 | Bethune et al. |
| 2011/0262968 A1 | 10/2011 | Gudas et al. |
| 2011/0268656 A1 | 11/2011 | Ho et al. |
| 2011/0269637 A1 | 11/2011 | Broet et al. |
| 2012/0076728 A1 | 3/2012 | Wu et al. |
| 2012/0087862 A1 | 4/2012 | Hood et al. |
| 2012/0136137 A1 | 5/2012 | Kobilka et al. |
| 2012/0144110 A1 | 6/2012 | Smith |
| 2012/0159672 A1 | 6/2012 | Alexandrov et al. |
| 2012/0183566 A1 | 7/2012 | Barfield et al. |
| 2012/0276563 A1 | 11/2012 | Wieland |
| 2012/0283418 A1 | 11/2012 | Wu et al. |
| 2012/0301899 A1 | 11/2012 | Choo et al. |
| 2012/0309941 A1 | 12/2012 | Strome et al. |
| 2013/0197192 A1 | 8/2013 | Kobilka et al. |
| 2013/0247233 A1 | 9/2013 | Gaitanaris et al. |
| 2013/0323236 A1 | 12/2013 | Humphreys et al. |
| 2014/0017244 A1 | 1/2014 | Duerr et al. |
| 2014/0105913 A1 | 4/2014 | Strome et al. |
| 2014/0106981 A1 | 4/2014 | Hood et al. |
| 2014/0120085 A1 | 5/2014 | Tureci et al. |
| 2014/0162341 A1 | 6/2014 | Kobilka |
| 2014/0194595 A1 | 7/2014 | Kobilka et al. |
| 2014/0234215 A1 | 8/2014 | Ho et al. |
| 2014/0271462 A1 | 9/2014 | Ho et al. |
| 2014/0286951 A1 | 9/2014 | Gurney et al. |
| 2014/0302035 A1 | 10/2014 | Harms et al. |
| 2014/0335075 A1 | 11/2014 | Strome et al. |
| 2015/0017169 A1 | 1/2015 | Humphreys et al. |
| 2015/0018529 A1 | 1/2015 | Humphreys et al. |
| 2015/0056185 A1 | 2/2015 | Strome et al. |
| 2015/0057166 A1 | 2/2015 | Kobilka |
| 2015/0118252 A1 | 4/2015 | Ho et al. |
| 2015/0191543 A1 | 7/2015 | Wu et al. |
| 2015/0210751 A1 | 7/2015 | Kobilka et al. |
| 2016/0068613 A1 | 3/2016 | Regula et al. |
| 2016/0083450 A1 | 3/2016 | Wu et al. |
| 2016/0159894 A1 | 6/2016 | Hartmann et al. |
| 2016/0193335 A1 | 7/2016 | Tureci et al. |
| 2016/0194389 A1 | 7/2016 | Regula et al. |
| 2016/0219845 A1 | 8/2016 | Gaitanaris et al. |
| 2016/0272990 A1 | 9/2016 | Kovalic et al. |
| 2016/0280768 A1 | 9/2016 | Strome et al. |
| 2016/0282365 A1 | 9/2016 | Gaitanaris et al. |
| 2016/0355570 A1 | 12/2016 | Strome et al. |
| 2016/0362473 A1 | 12/2016 | Wang |
| 2016/0362474 A1 | 12/2016 | Wang |
| 2017/0029507 A1 | 2/2017 | Ho et al. |
| 2017/0051044 A1 | 2/2017 | Chan et al. |
| 2018/0221507 A1 | 8/2018 | Gudas et al. |
| 2018/0346605 A1 | 12/2018 | Chiu |
| 2020/0157204 A1 | 5/2020 | Humphreys et al. |
| 2021/0371527 A1 | 12/2021 | Mascioni et al. |

FOREIGN PATENT DOCUMENTS

| | | |
|---|---|---|
| CN | 1854295 | 11/2006 |
| EP | 1 550 729 | 7/2005 |
| EP | 0 956 506 | 3/2006 |
| EP | 1 005 494 | 12/2008 |
| EP | 1 997 514 | 12/2008 |
| EP | 1 629 011 | 1/2010 |
| EP | 2 226 394 | 9/2010 |
| EP | 2 260 858 | 12/2010 |
| EP | 2 476 754 | 7/2012 |
| EP | 2 966 085 | 1/2016 |
| JP | 2008-528668 | 7/2008 |
| WO | WO 89/01974 | 3/1989 |
| WO | WO 93/11794 | 6/1993 |
| WO | WO 93/015199 | 8/1993 |
| WO | WO 94/05690 | 3/1994 |
| WO | WO 94/009820 | 5/1994 |
| WO | WO 95/22609 | 8/1995 |
| WO | WO 96/008570 | 3/1996 |
| WO | WO 96/026272 | 8/1996 |
| WO | WO 98/52975 | 11/1998 |
| WO | WO 99/15549 | 4/1999 |
| WO | WO 99/056779 | 11/1999 |
| WO | WO 00/014234 | 3/2000 |
| WO | WO 01/005427 | 1/2001 |
| WO | WO 01/009303 | 2/2001 |
| WO | WO 01/68708 | 9/2001 |
| WO | WO 01/082963 | 11/2001 |
| WO | WO 02/022680 | 3/2002 |
| WO | WO 03/038098 | 5/2003 |
| WO | WO 04/108158 | 12/2004 |
| WO | WO 05/026334 | 3/2005 |
| WO | WO 05/043165 | 5/2005 |
| WO | WO 05/061547 | 7/2005 |
| WO | WO 05/068616 | 7/2005 |
| WO | WO 05/094882 | 10/2005 |
| WO | WO 07/064345 | 6/2007 |
| WO | WO 07/087673 | 8/2007 |
| WO | WO 07/109321 | 9/2007 |
| WO | WO 07/137117 | 11/2007 |
| WO | WO 09/017823 | 2/2009 |
| WO | WO 09/032949 | 3/2009 |
| WO | WO 09/041613 | 4/2009 |
| WO | WO 09/076099 | 6/2009 |
| WO | WO 09/082443 | 7/2009 |
| WO | WO 09/097128 | 8/2009 |
| WO | WO 09/130575 | 10/2009 |
| WO | WO 10/003108 | 1/2010 |
| WO | WO 10/003118 | 1/2010 |
| WO | WO 10/037397 | 4/2010 |
| WO | WO 10/040105 | 4/2010 |
| WO | WO 10/042904 | 4/2010 |
| WO | WO 10/065578 | 6/2010 |
| WO | WO 10/102195 | 9/2010 |
| WO | WO 10/136492 | 12/2010 |
| WO | WO 11/000054 | 1/2011 |
| WO | WO 11/056983 | 5/2011 |
| WO | WO 11/069019 | 6/2011 |
| WO | WO 11/075786 | 6/2011 |
| WO | WO 11/090762 | 7/2011 |
| WO | WO 11/096894 | 8/2011 |
| WO | WO 11/107480 | 9/2011 |
| WO | WO 11/109440 | 9/2011 |
| WO | WO 12/022982 | 2/2012 |
| WO | WO 12/143524 | 10/2012 |
| WO | WO 13/020074 | 2/2013 |
| WO | WO 14/025828 | 2/2014 |
| WO | WO 14/164553 | 10/2014 |
| WO | WO 15/107015 | 7/2015 |
| WO | WO 15/107025 | 7/2015 |
| WO | WO 15/107026 | 7/2015 |
| WO | WO 15/175357 | 11/2015 |
| WO | WO 16/016299 | 2/2016 |
| WO | WO 17/027325 | 2/2017 |

(56) References Cited

FOREIGN PATENT DOCUMENTS

| WO | WO 17/176769 | 10/2017 |
|----|--------------|---------|
| WO | WO 18/111973 | 6/2018 |
| WO | WO 18/147960 | 8/2018 |
| WO | WO 19/023148 | 1/2019 |

OTHER PUBLICATIONS

De Genst et al., Dev Comp Immunol 2006; 30:187-98 (Year: 2006).*
Yoshinaga et al., J. Biochem 2008; 143:593-601 (Year: 2008).*
Almagro & Fransson, Frontiers in Bioscience 2008; 13:1619-33 (Year: 2008).*
Office Action dated Jul. 10, 2020 in U.S. Appl. No. 15/228,616.
Summons to attend oral proceedings pursuant to Rule 115(1) EPC dated Jul. 30, 2020 in European Application No. 14 779 573.6.
U.S. Appl. No. 10/690,990, filed Oct. 23, 2003, Wu et al.
U.S. Appl. No. 12/788,477, filed May 27, 2010, Wu et al.
Aarntzen et al., Nov. 8, 2011, Early identification of antigen-specific immune responses in vivo by [18F]-labeled 3'-fluoro-3'-deoxy-thymidine ([18F]FLT) PET imaging. Proc Natl Acad Sci USA, 108(45):18396-1839.
Adams et al., Sep. 1, 1993, Highly specific in vivo tumor targeting by monovalent and divalent forms of 741F8 anti-c-erbB-2 single-chain Fv, Cancer Res., 53(17):4026-4034.
Adlersberg, J,., The immunoglobulin hinge (interdomain) region., Ric Clin Lab, vol. 6, No. 3. pp. 191-205, (1976).
Albrecht et al., Dec. 2007, Development of anti-MUC1 di-scFvs for molecular targeting of epithelial cancers, such as breast and prostate cancers, 51(4):304-313.
Ali et al., 2012, Xenogeneic graft-versus-host-disease in NOD-scid IL2R gamma null mice display a T-effector memory phenotype. PLoS One, 7(8), e44219. doi:10.1371/journal.pone.0044219.
Al-Lazikani et al., 1997, Standard conformations for the canonical structures of immunoglobulins, Journal of Molecular Biology, 273(4):927-948.
Almagro et al, 2008, Humanization of antibodies, Frontiers in Bioscience, 13:1619-1633.
Altschul et al., 1997, Gapped BLAST and PSI-BLAST: a new generation of protein database search programs, Nucleic Acids Research, 1997, 25(17):3389-3402.
Altschul et al., Oct. 5, 1990, Basic local alignment search tool, Journal of Molecular Biology, 215(3):403-410.
Asano et al., 2006, Humanization of the bispecific epidermal growth factor receptor x CD3 diabody and its efficacy as a potential clinical reagent, Clinical Cancer Research, 12(13):4036-4042.
Atwell et al., Jul. 1999, scFv multimers of the anti-neuranminidase antibody NC10: length of the linker between VH and VL domains dictates precisely the transition between diabodies and triabodies, Protein Engineering, 12(7):597-604.
Ausubel et al., 1995, Current protocols in molecular biology, 1, cap. 2—Preparation and analysis of DNA. Phenol extraction and ethanol precipitation of DNA. by John Wiley & Sons, Inc. 2.1.1-2.1.3.
Baeuerle et al., 2009, Bispecific T-Cell Engaging Antibodies for Cancer Therapy, Cancer Res, 69:4941-4944.
Bander et al., Jul. 20, 2005, Phase I trial of 177 Lutetium-labeled J591, a monoclonal antibody to prostate-specific membrane antigen, in patients with androgen-independent prostate cancer, Journal of Clinical Oncology, 23(21):4591-4601.
Bander et al., Nov. 2003, Targeting Metastatic Prostate Cancer with Radiolabeled Monoclonal Antibody J591 to the Extracellular Domain of Prostate Specific Membrane Antigen, The Journal of Urology, 170:1717-1721.
Barat et al., Aug. 19, 2009, Cys-Diabody Quantum Dot Conjugates (immunoQdots) for Cancer Marker Detection, Bioconjug. Chem., 20(8):1474-1481.
Basu S. et al., Jan. 2009, Positron emission tomography as a diagnostic tool in infection: present role and future possibilities. Semin Nucl Med., 39(1):36-51.

Batzer et al., 1991, Enhanced Evolutionary PCR Using Oligonuleotides with Inosine at the 3'-Terminus, E Nucleic Acid Res. 19:5081.
Boerman and Oyen, 2011, Immuno-PET of Cancer: A Revival of Antibody Imaging, J. Nucl Med. 52(8):1171-1172.
Brahmer, J. et al., 2012, Safety and activity of anti-PD-L1 antibody in patients with advanced cancer, N Engl J Med, 366(26):2455-2465. doi:10.1056/NEJMoa1200694.
Brezski et al., 2011, The in vitro resistance of IgG2 to proteolytic attack concurs with a comparative paucity of autoantibodies against peptide analogs of the IgG2 hinge. Mabs, pp. 558-567.
Brochet et al., 2008, IMGT/V-QUEST: the highly customized and integrated system for IG and TR standardized V-J and V-D-J sequence analysis, Nucl. Acids Res, 36:W503-508.
Caldas et al., May 2003, Humanization of the Anti-CD18 Antibody 6.7: an unexpected effect of a framework residue in binding to antigen, Mol. Immunol. 39(15):941-952.
Carmichael et al., Feb. 14, 2003, The crystal structure of an anti-CEA scFv diabody assembled from T84.66 scFvs in V(L)-to-V(H) orientation: Implications for diabody flexibility, J. Mol. Biol., 326(2):341-351.
Carter et al., Aug. 1997, Engineering antibodies for imaging and therapy, Curr. Opin. Biotechnol., 8(4):449-454.
Chaderjian et al., 2005, Effect of copper sulfate on performance of a serum-free CHO cell culture process and the level of free thiol in the recombinant antibody expressed, Biotechnol. Prog., 21:550-553.
Chang et al., Aug. 1997, Prostate-Specific Membrane Antigen is Produced in Tumor-Associated Neovasculature1, Clin. Cancer Res., 5:2674-2681.
Chatenoud, L. and Bluestone, J.A CD3-specific antibodies: a portal to the treatment of autoimmunity Nature Reviews Immunoloqy 2007, 7: 622-632.
Chen et al., Jun. 14, 2016., Analysis of Immune Signatures in Longitudinal Tumor Samples Yields Insight into Biomarkers of Response and Mechanisms of Resistance to Immune Checkpoint Blockade Cancer Discovery Cancer Discov 2016;6:827-837.
Chien et al., Jul. 1989, Significant Structural and Functional Change of an Antigen-Bidning Site by a Distant Amino Acid Substitution: Proposal of a Structural Mechanism, Proc. Natl. Acad. Sci. USA. 86(14):5532-5536.
Chothia et al., Aug. 20, 1987, Canonical structures for the hypervariable regions of immunoglobulins, Journal of Molecular Biology, 196(4):901-917.
Chothia et al., Dec. 1989, Conformations of immunoglobulin hypervariable regions, Nature, 342:877-883.
Chothia et al., Oct. 5, 1992, Structural repertoire of the human VH segments, Journal of Molecular Biology, 227(3):799-817.
Cipponi et al., 2011, Tumor-infiltrating lymphocytes: apparently good for melanoma patients. But why?, Cancer Immunol Immunother, 60:1153-1160.
City of Hope National Medical Center, Nov. 27, 2004, Anti-CEA antibody T84.66 humanized, Medical Imaging Law Weekly, http://www.newsrx.com/newsletters/Medical-Imaging-Law-Weekly ; dated for online publication Nov. 27, 2004.
Clemente et al., 1996, Prognostic value of tumor infiltrating lymphocytes in the vertical growth phase of primary cutaneous melanoma. Cancer, 77:1303-1310.
Cole et al., 1985, Monoclonal Antibodies and Cancer Therapy, Alan R. Liss, Inc., pp. 77-96.
De Pascalis et al., 2002, Grafting of Abbreviated Complementarity-Determining Regions Containing Specificity-Determining Residues Essential for Ligand Contact to Engineer a Less Immunogenic Humanized Monoclonal Antibody, J. Immunol., 169(6):3076-3084.
Deri et al., Jan. 2013, PET Imagining with 89Zr: From Radiochemistry to the Clinic, Nucl Med Biol., 40(1):27 pp.
Desplancq et al., Aug. 1994, Multimerization behaviour of single chain Fv variants for the tumour-binding antibody B72.3, Protein Engineering, 7(8):1027-1033.
Devine et al., 1999, Molecular analysis of protein interactions mediating the function of the cell surface protein CD8. Immunol Res, 19(2-3):201-210. doi:10.1007/bf02786488.
Eisenhauer, E. A., et al., 2009, New response evaluation criteria in solid tumours: revised RECIST guideline (version 1.1) Eur J Cancer, 45(2):228-247. doi:10.1016/j.ejca.2008.10.026.

(56) References Cited

OTHER PUBLICATIONS

Elzinga E.H. et al., Nov.-Dec. 2007, 2-Deoxy-2-[F-18]fluoro-D-glucose joint uptake on position emission tomography images: rheumatoid arthritis versus osteoarthritis. Mal Imaging Biol., 9(6):357-360.

Feng Z., et al., 2015, Multispectral imaging of formalin fixed tissue predicts ability to generate tumor-infiltration lymphocytes from melanoma. Journal for Immunotherapy of Cancer, 3:47, doi:10.1186/s40425-015-0091-z.

Fitzgerald et al., 1997, Improved tumour targeting by disulphide stabilized diabodies expressed in Pichia pastoris, Protein Engineering, 10(10):1221-1225.

Fukunaga et al., 2004, CD8+ tumor-infiltrating lymphocytes together with CD4+ tumor-infiltrating lymphocytes and dendritic cells improve the prognosis of patients with pancreatic adenocarcinoma. Pancreas 28:e26-e31.

Galati et al., 2003, Increased Resistance of Peptides to Serum Proteases by Modification of their Amino Groups, Z. Naturforsch, 58:558-561.

Galon et al., 2006, Type, density, and location of immune cells within human colorectal tumors predict clinical outcome. Science, 313:1960-1964.

Garon et al., 2018, Pembrolizumab for the Treatment of Non-Small-Cell Lung Cancer. N Engl J Med, 372(21):28.

George et al., Aug. 1995, Radiometal labeling of recombinant proteins by a genetically engineered minimal chelation site: technetium-99m coordination by single-chain Fv antibody fusion proteins through a C-terminal cysteinyl peptide, Proc. Natl. Acad. Sci. USA, 92(18):8358-8362.

Gillies et al., 1990, Antigen Binding and Biological Activities of Engineered Mutant Chimeric Antibodies with Human Tumor Specificities, Hum Antibodies Hybridomas. 1(1):47-54.

Giudicelli et al., 2006, IMGT/LIGM-DB, the IMGT.RTM. comprehensive database of immunoglobulin and T cell receptor nucleotide sequences, Nucleic Acids Research, 34:D781-D784.

Giusti et al., May 1987, Somatic Diversification of S107 from an Antiphosphocholine to an anti-DNA Autoantibody is due to a Single Base Changes in its Heavy Chain Variable Region, Proc. Natl. Acad. Sci. USA, 84(9):2926-2930.

Glaser et al., 2005, Novel Antibody Hinge Regions for Efficient Production of CH2 Domain-deleted Antibodies, Journal of Biological Chemistry, 280:41494-41503.

Glockshuber et al., 1990, A comparison of strategies to stabilize immunoglobulin Fv-fragments, Biochemistry, 29(6):1362-1367.

Goldsby et al., 2002, Immunology, 5th edition, W.H. Freeman and Company, New York, pp. 79-83.

Gu et al., 2005, Biological activity and microPET imaging properties of chimeric and humanized anit-prostate stem cell antigen (PSCA) antibodies, Proc Amer Assoc Cancer Res., 46, Abstract #696 [Retrieved on May 14, 2012], URL: http://aacrmeetingabstracts.org/cgi/content/abstract/2005/1/164-b.

Gussow et al. 1991, Methods in Enzymology. 203:99-121.

Hamanishi et al., 2007, Programmed cell death 1 ligand 1 and tumor-infiltrating CD8+ T lymphocytes are prognostic factors of human ovarian cancer. Proc Natl Acad. Sci USA, 104:3360-3365.

Harlow and Lane, 1998, Using Antibodies, A Laboratory Manual, Cold Spring Harbo Laboratory, USA.

Haurum, Jul. 2006, Recombinant polyclonal antibodies: the next generation of antibody therapeutics?, Drug Discovery Today, 11(13/14).

Henikoff et al., Nov. 1992, Amino acid substitution matrices from protein blocks, Proc. Natl. Acad. Sci. USA, 89:10915-10919.

Hingeprot, An Algorithm for protein hinge prediction using elastic network models, 2 pp. //bioinfo3d.cs.tau.ac.il/HingeProt/hingeprot.html (pp. 1-2; Aug. 26, 2018).

Hiraoka Net al., 2006, Prevalence of FOXP3+ regulatory T cells increases during the progression of pancreatic ductal adenocarcinoma and its premalignant lesions. Clin. Cancer Res., 12:5423-5434.

Hodi et al., 2010, Improved survival with ipillimumab in patients with metastatic melanoma. N Engl J Med, 363(8):711-723. doi:10.1056/NEJMoa1003466.

Hoffman et al., 1980, Simple and rapid measurement of human T lymphocytes and their subclasses in peripheral blood. Proc Natl Acad Sci USA, 77:4914-4917.

Hollinger et al., Jul. 1993, Diabodies: Small bivalent and bispecific antibody fragments, Proc. Natl. Acad. Sci. USA, 90:6444-6448.

Holm et al. Feb. 2007, Mol. Immunol. 44(6):1075-1084.

Hopp et al., 1983, A Computer Program for Predicting Protein Antigenic Determinants, Molecular Immunology, 20(4):6444-6448.

Hu et al., 1996, Minibody: a novel engineered anti-carcinoembryonic antigen antibody fragment (single-chain Fv-CH3) which exhibits rapid, high-level targeting of xenografts, Cancer Research, 56:3055-3061.

InvivoGen, 2011, Engineering Fc regions for altered properties, retrieved using the WayBackMachine Internet Archive captured on Dec. 13, 2011 (including banner on top).

InvivoGen, 2011, Engineering Fc regions for altered properties, retrieved using the WayBackMachine Internet Archive captured on Dec. 13, 2011 (with banner on top removed).

Issekutz et al., Nov. 2011, Coexpression of Chemokine Receptors CCR5, CXCR3, and CCR4 and Ligands for P- and E-Selectin on T Lymphocytes of Patients With Juvenile Idiopathic Arthritis, Arthritis & Rheumatism, 63(11):3467-3476.

Janeway et al., 2001, Chapter 3: Antigen recongnition by B-cell and T-cell Receptors, in Immunobiology, 5th Ed., Garland Publishing, New York, NY, pp. 94-105.

Jochems et al., 2011, Tumor-infiltrating immune cells and prognosis: the potential link between conventional cancer therapy and immunity. Exp Biol Med (Maywood), 236(5):567-579.

Johnson et al., Jun. 11, 2010, Effector cell recruitment with novel Fv-based dual-affinity re-targeting protein leads to potent tumor cytolysis and in vivo B-cell depletion, J. Mol. Biol., 399(3):436-449.

Jones et al., May 29, 1986, Replacing the complementarity-determining regions in a human antibody with those from a mouse, Nature, 321:522-525.

Juweid M.E. et al., Feb. 2, 2006, Positron-emission tomography and assessment of cancer therapy. N Engl J Med., 354(5):496-507.

Kabat et al., 1991, Sequences of Proteins of Immunological Interest, 5th ed., NIH Publication No. 91-3242.

Karja et al., 2005, Tumour-infiltrating lymphocytes: a prognostic factor of PSA-free survival in patients with local prostate carcinoma treated by radical prostatectomy. Anticancer Res. 25:4435-4438.

Karlin et al., Jun. 1993, Applications and statistics for multiple high-scoring segments in molecular sequences, Proc. Natl. Acad. Sci. USA, 90:5873-5877.

Keymeulen et al., 2010, Transient Epstein-Barr virus reactivation in CD3 monoclonal antibody-treated patients, Blood, 115:1145-1155.

Kim et al., Aug. 2008, Anti-CD30 diabody-drug conjugates with potent antitumor activity, Mol. Cancer Ther., 7(8):2486-2497.

Kjer-Nielsen et al., 2004, Crystal structure of the human T cell receptor CD3{epsilon}-{gamma} heterodimer complexed to the therapeutic mAB OKT3, PNAS, 101(20):7675-7680.

Klein et al., Apr. 1, 2009, Melan-A-specific Cytotoxic T Cells Are Associated with Tumor Regression and Autoimmunity Following Treatment with Anti-CTLA-4, Clin Cancer Res, 15(7):2507-2513.

Knappik, et al. 2000, Fully synthetic human combinatorial antibody libraries (HuCAL) based on modular consensus frameworks and CDRs randomized with trinucleotides, J.Mol Biol., 296(1):57-86.

Knowles S.M. et al., Nov. 1, 2012, Advances in immuno-positron emission tomography: antibodies for molecular imaging in oncology, J Clin Oneal. (31):3884-3892.

Kohler et al., 1975, Continuous cultures of fused cells secreting antibody of predefined specificity, Nature, 256(5517):495-497.

Koya R.C. et al., Aug. 10, 2010, Kinetic phases of distribution and tumor targeting by T cell receptor engineered lymphocytes inducing robust antitumor responses. Proc Natl Acad Sci USA, 107(32):14286-14291.

Kozbor et al., Mar. 1983, The production of monoclonal antibodies from human lymphocytes, Immunology Today, 4(3):72-79.

(56) References Cited

OTHER PUBLICATIONS

Kuby, Immunology, 4th ed., Chapter 4. W.H. Freeman & Co., New York, 2000.
Kukis et al., Feb. 1, 1995, Effect of the extent of chelate substitution on the immunoreactivity and biodistribution of 2IT-BAT-Lym-1 immunoconjugates, Cancer Research, 55:878-884.
Laing R.E. et al., Feb. 2010, Visualizing cancer and immune cell function with metabolic positron emission tomography. Curr Opin Genet Dev., 20(1):100-105.
Le Gall et al., 2004, Immunosuppressive properties of anti-CD3 single-chain Fv and diabody, Journal of Immunological Meth, 285(1):111-127.
LeFranc et al., Jan. 2003, IMGT unique numbering for immunoglobulin and T cell receptor variable domains and Ig superfamily V-like domains, Developmental & Comparative Immunology, 27(1):55-77.
Leung, S., 1995, Engineering a unique glycosylation site for site-specific conjugation of haptens to antibody fragments, The Journal of Immunology, 154:5919-5926.
Lewis et al., 2001, An improved method for conjugating monoclonal antibodies with N-Hydroxysulfosuccinimidyl DOTA, Bioconjugate Chem, 12:320-324.
Leyton et al., Nov. 15, 2008, Humanized radioiodinated minibody for imaging of prostate stem cell antigen-expressing tumors, Clinical Cancer Research, 14(22):7488-7496.
Li et al., 1997, Mammalian cell expression of dimeric small immune proteins (SIP), Protein Engineering, 10(6):731-736.
Li et al., 2002, Reduction of kidney uptake in radiometal labeled peptide linkers conjugated to recombinant antibody fragments, site-specific conjugation of DOTA-peptides to a Cys-diabody, Bioconjugate Chem., 13(5):985-995.
Li et al., Jan.-Feb. 2006, Improved biodistribution and radioimmunoimaging with poly(ethylene glycol)-DOTA-conjugated anti-CEA diabody, Bioconjug. Chem., 7(1):68-76.
Liu et al., Jul. 1, 2009, Prostate-Specific Membrane Antigen Retargeted Measles Virotherapy for the Treatment of Prostate Cancer, Prostate, 69(10):1128-1141.
Liu et al., Mar. 15, 2012, CD8+ lymphocyte infiltration is an independent favorable prognostic indicator in basal-like breast cancer. Breast Cancer Res. 14(2).
Liu et al., Sep. 1, 1997, Monoclonal antibodies to the extracellular domain of prostate-specific membrane antigen also react with tumor vascular endothelium, Cancer Research, 57:3629-3634.
Liu et al., Sep. 1, 1998, Constitutive and antibody-induced internalization of prostate-specific membrane antigen, Cancer Research, 58:4055-4060.
Lo, 2004, Antibody Humanization by CDR Grafting, Methods in Molecular Biology, 248:135-159.
Lopes et al., 2010, Use of 99mTc-anti-CD3 scintigraphy in the differential diagnosis of rheumatic diseases, Rheumatology, 49:933-939.
MacCallum et al., Oct. 11, 1996, Antibody-antigen Interactions: Contact Analysis and Binding Site Topography, Journal of Molecular Biology, 262(5):732-745.
Mackensen et al., 1993, Evidence for in situ amplification of cytotoxic T-lymphocytes with antitumor activity in a human regressive melanoma. Cancer Res. 53:3569-3573.
Mahmoud et al., 2011, Tumor-infiltrating CD8+ lymphocytes predict clinical outcome in breast cancer. J Clin Oncol., 29(15):1949-1955.
Mahmoud et al., May 1, 2012, CD8+ T lymphocytes infiltrating breast cancer: A promising new prognostic marker? Oncoimmunology. 1(3):364-365.
Malviya, et al., 2014, Targeting T and B lymphocytes with radiolabelled antibodies fodiagnostic and herapeutic applications, Journal of Nuclear Medicine and Molecular Imagining, 54:654-676.
Mamede et al., Mar.-Apr. 2003, Differential uptake of (18)F-fluorodeoxyglucose by experimental tumors xenografted into immunocompetent and immunodeficient mice and the effect of imnnomodification. Neoplasia. 5(2):179-183.

Mariuzza et al., "The Structural Basics of Antigen-Antibody Recognition," Annu. Rev. Biophys. Biophys. Chem. 1987; 16: 139-159.
Marks et al., 1992, By-Passing Immunization: Building High Affinity Human Antibodies by Chain Shuffling, Nature Biotechnology 10:779-783.
Martin et al., Dec. 1989, Modeling antibody hypervariable loops: A combined algorithm, Proc. Natl. Acad. Sci. USA, 86:9268-9272.
Martin, 2010, Protein Sequence and Structure Analysis of Antibody Variable Domains, in Chapter 3 of Antibody Engineering 2, Kontermann and Dubel Eds., Springer-Verlag Berlin Heidelberg 2010, pp. 33-51.
Martins et al., Jan. 2008, Monitoring rheumatoid arthritis synovitis with 99mTc-anti-CD3, Br J Radiol., 81(961):25-29.
Marty et al., Feb. 2001, Production of functionalized single-chain Fv antibody fragments binding to the ED-B domain of the B-isoform of fibronectin in Pichia pastoris, Protein Expression and Purification, 21(1):156-164.
Massoud et al., 2003, Molecular Imaging in Living Subjects: Seeing Fundamental Biological Processes in a New Light, Genes Dev, 17(5):545-580.
Matsui K. et al., Nov. 2004, Quantitation and visualization of tumor-specific cells in the secondary lymphoid organs during and after tumor elimination by PET. Nucl Med Biol. 31(8):1021-1031.
McCafferty et al., Dec. 6, 1990, Phage antibodies: filamentous phage displaying antibody variable domains, Nature 348:552-554.
Mccartney et al., 1993, Refolding of single-chain Fv with C-terminal cysteine (sFv); formation of disulfide-bonded homodimers of antic-À£'r/7B-2 and anti-digoxin sFv', Miami Short Rep., 3:91.
Mccartney et al., Sep. 1, 1997, Engineering disulfide-linked single-chain Fv dimers [(sFv')2] with improved solution and targeting properties: Anti-digoxin 26-10 (sFv')2 and anti-c-erbB-2 741F8 (sFv')2 made by protein folding and bonded through C-termincal cysteinyl peptides, Protein Eng., 8(3):301-314.
McCracken et al., 2016, Advances in PET Detection of the Anti-tumor T Cell Response, Adv Immunol 131.
Mcdevitt, M. et al., 2000, An Particle Emmitting Antibody For Radioimmunotherapy of Prostate Acnecer, Cancer Research, 60:6095-6100.
Mellman, 2011, Cancer immunotherapy comes of age. Nature, 480(7378):480-489. doi:10.1038/nature10673.
Milowsky et al., Feb. 10, 2007, Vascular targeted therapy with anti-prostate-specific membrane antigen monoclonal antibody J591 in advanced solid tumors, Journal of Clinical Oncology, 25(5):540-547.
Milowsky et al., Jul. 1, 2004, Phase I Trial of yttrium-90-labeled anti-prostate-specific membrane antigen monoclonal antibody J591 for androgen-independent prostate cancer, Journal of Clinical Oncology, 22(13):2522-2531.
Mlecnik et al., Feb. 20, 2011, Histopathologic-based prognostic factors of colorectal cancers are associated with the state of the local immune reaction. J Clin Oncol. 29(6).
Moebius et al., 1991, Expression of different CD8 isoforms on distinct human lymphocyte subpopulations. Eur J Immunol, 21(8):1793-1800. doi:10.1002/eji.1830210803.
Moore et al., Apr. 28, 2011, Application of dual affinity retargeting molecules to achieve optimal redirected T-cell killing B-cell lymphoma, Blood, 117(17):4542-4551.
Morris et al., 2005, Pilot trial of unlabeled and indium-111-labeled anti-prostate-specific membrane antigen antibody J591 for castrate metastatic prostate cancer, Clinical Cancer Research, 11:7454-7461.
Nagengast et al, Jan. 1, 2011, VEGF-PET Imaging is a Noninvasive Biomarker Showing Differential Changes in the Tumor during Sunitinib Treatment, Cancer Res, 71(1):143-153.
Nair-Gill et al., Feb. 2008, Non-invasive imaging of adaptive immunity using positron emission tomography. Immunol Rev. 221:214-228.
Nair-Gill et al., Jun. 2010, PET probes for distinct metabolic pathways have different cell specificities during immune responses in mice. J Clin Invest., 120(6):2005-2015.
Nakakubo et al. 2003, Clinical significance of immune cell infiltration within gallbladder cancer. Br. J. Cancer, 89:1736-1742.

(56) References Cited

OTHER PUBLICATIONS

Nakano et al., 2001, Proliferative activity of intratumoral CD8(+) T-lymphocytes as a prognostic factor in human renal cell carcinoma: Clinicopathologic demonstration of antitumor immunity. Cancer Res. 61:5132-5136.
Nanus et al., Dec. 2003, Clinical Use of Monoclonal Antibody HuJ591 Therapy: Targeting Prostate Specific Membrane Antigen, The Journal of Urology, 170:S84-S89.
NCBI Predicted: galectin-7-like [Python bivittatus]; NCBI Reference Sequence: XP_007443107.1; Reference bears a date of Mar. 11, 2016; however, as this item refers to a webpage, it may have been available in some form at an earlier date; Accessed, downloaded, and printed on Dec. 21, 2017.
NCBI Predicted: late cornified envelope-like proline-rich protein 1 [Cricetulus griseus] NCBI Reference Sequence: XP_007650016.1; Reference bears a date of May 27, 2016; however, as this item refers to a webpage, it may have been available in some form at an earlier date; Accessed, downloaded, and printed on Dec. 20, 2017.
NCBI Predicted: late cornified envelope-like proline-rich protein 1 [Erinaceus europaeus]; NCBI Reference Sequence: XP_007525458.1; Reference bears a date of Apr. 11, 2016; however, as this item refers to a webpage, it may have been available in some form at an earlier date; Accessed, downloaded, and printed on Dec. 20, 2017.
NCBI Predicted: late cornified envelope-like proline-rich protein 1 [Mesocricetus auratus]; NCBI Reference Sequence: XP_005080368.1; Reference bears a date of May 22, 2017; however, as this item refers to a webpage, it may have been available in some form at an earlier date; Accessed, downloaded, and printed on Dec. 20, 2017.
NCBI Predicted: late cornified envelope-like proline-rich protein 1 [Mus musculus]; NCBI Reference Sequence: NP_081318.1; Reference bears a date of Oct. 31, 2017; however, as this item refers toa webpage, it may have been available in some form at an earlier date; Accessed, downloaded, and printed on Dec. 20, 2017.
NCBI Predicted: late cornified envelope-like proline-rich protein 1 [Peromyscus maniculatus bairdii]; NCBI Reference Sequence: XP_006976519.1; Reference bears a date of Mar. 21, 2016; however, asthis item refers to a webpage, it may have been available in some form at an earlier date; Accessed, downloaded, and printed on Dec. 20, 2017.
NCBI Predicted: late cornified envelope-like proline-rich protein 1 [Pteropus vampyrus]; NCBI Reference Sequence: XP_011379372.1; Reference bears a date of Feb. 23, 2015; however, as this item refers to a webpage, it may have been available in some form at an earlier date; Accessed,downloaded, and printed on Dec. 20, 2017.
NCBI Predicted: late cornified envelope-like proline-rich protein 1 [Vicugna pacos] ; NCBI Reference Sequence: XP_006214801.1; Reference bears a date of Dec. 29, 2015; however, as this item refers to a webpage, it may have been available in some form at an earlier date; Accessed, downloaded, and printed on Dec. 20, 2017.
NCBI Predicted: LIM domain only protein 7 [Astyanax mexicanus]; NCBI Reference Sequence: XP_015461938.1; Reference bears a date of Feb. 11, 2016; however, as this item refers to a webpage, it may have been available in some form at an earlier date; Accessed, downloaded, and printed on Dec. 20, 2017.
NCBI Predicted: Low Quality Protein: zinc finger protein 345-like [Microtus ochrogaster]; NCBI Reference Sequence: XP_013202654.1; Reference bears a date of Aug. 7, 2015, however, as thisitem refers to a webpage, it may have been available in some form at an earlier date; Accessed, downloaded, and printed on Dec. 19, 2017.
NCBI Predicted: mitochondria-eating protein [Parus major]; NCBI Reference Sequence: XP_015479149.1; Reference bears a date of Nov. 14, 2016; however, as this item refers to a webpage, it may have been available in some form at an earlier date; Accessed, downloaded, andprinted on Dec. 20, 2017.
NCBI Predicted: serpin B9 isoform X1 [Ovis aries]; NCBI Reference Sequence: XP_011956764.1; Reference bears a date of Dec. 17, 2015; however, as this item refers to a webpage, it may have been available in some form at an earlier date; Accessed, downloaded, and printed on Dec. 20, 2017.
NCBI Predicted: small proline-rich protein 2E [Sus scrofa]; NCBI Reference Sequence: XP_005663482.1; Reference bears a date of May 13, 2017; however, as this item refers to a webpage, it may have been available in some form at an earlier date; Accessed, downloaded, and printed on Dec. 20, 2017.
NCBI Predicted: uncharacterized protein C12orf60 homolog [Sarcophilus harrisii]; NCBI Reference Sequence: XP_012406148.1; Reference bears a date of May 15, 2015; however, as this item refers toa webpage, it may have been available in some form at an earlier date; Accessed, downloaded, and Printed on Dec. 20, 2017.
NCBI Predicted: zinc finger protein 135, partial [Erinaceus europaeus]; NCBI Reference Sequence: XP_016050621.1; Reference bears a date of Apr. 11, 2016, however, as this item refers to a webpage,it may have been available in some form at an earlier date; Accessed, downloaded, and printed on Dec. 19, 2017.
Needleman et al., Mar. 28, 1970, A general method applicable to the search for similarities in the amino acid sequence of two proteins, Journal of Molecular Biology, 48(3):443-453.
Neumaier et al., 1990, Cloning of the genes for T84.66, and antibody that has a high specificity and affinity for carcinoembryonic antigen, and expression of chimeric human/mouse T84.66 genes in myeloma and Chinese hamster ovary cells, Cancer Research, 50:2128-2134.
Ohtsuka et al., Mar. 10, 1985, An Alternative Approach to Deoxyoligonucleotides as Hybridization Probes by Insertion of Deoxyinosine at Ambiguous Codon Positions, J. Biol. Chem., 260(5):2605-2608.
Olafsen et al. 2010, Chapter 6: Generation of Single-Chain Fv Fragments and Multivalent Derivatives scFv-Fc and scFv-CH3 (Minibodies), in Antibody Engineering, 2, Springer-Verlag Berlin Heidelberg, pp. 69-84.
Olafsen et al., 2004, Characterization of engineered anti-p185 HER-2 (scFv-CH3)2 antibody fragments (minibodies) for tumor targeting, Protein Engineering, Design & Selection, Oxford University Press, 17(4):315-323.
Olafsen et al., 2006, Tunable pharmacokinetics: modifying the in vivo half-life of antibodies by directed mutagenesis of the Fc fragment, Nature Protocols, 1(4):2048-2060.
Olafsen et al., Apr. 2010, ImmunoPET imaging of B-cell lymphoma using 124I-anti-CD20 scFv dimers (diabodies), Protein Eng. Des. Sel., 23(4):243-249.
Olafsen et al., Jan. 2004, Covalent disulfide-linked anti-CEA diabody allows site-specific conjugation and radiolabeling for tumor targeting applications, Protein Eng. Des. Sel., 17(1):21-27.
Olafsen et al., May 1, 2010, Antibody Vectors for Imaging, Seminars in Nuclear Medicine, 40(3:)167-181.
Olafsen et al., Nov. 11-13, 2016, Development and clinical translation of 89Zr-Df-IAB22M2C for detecting CD8+ T Cells for immunotherapy applications, Abstract # 442 presented at the 31.sup.st Annual Meeting and Associated Programs of the Society of Immunotherapy of Cancer (SITC 2016), The abstract and corresponding poster are provided in 13 pp.
Olafsen et al., November 408, 2015, Pet imaging of cytotoxic human T cells using an 89Zr-labeled anti-CD8 minibody, Abstract # P338 presented at the 30.sup.th Annual Meeting and Associated Programs of the Society for Immunotherapy of Cancer (SITC 2015), The abstract and corresponding poster are provided in 12 pages.
Olafsen et al., Sep. 2009, Recombinant anti-CD20 antibody fragments for small-animal PET imaging of B-Cell lymphomas, The Journal of Nuclear Medicine, 50(9):1500-150.
Olson et al., 2007, Clinical trials of cancer therapies targeting prostate-specific membrane antigen, Reviews on Recent Clinical Trials, 2:182-190.
Overwijk et al., Aug. 18, 2003, Tumor Regression and Autoimmunity after Reversal of a Functionally Tolerant State of Self-reactive CD8.sup.+T Cells, The Journal of Experimental Medicine, 198(4):569-580.
Pages et al., 2009, In situ cytotoxic and memory T cells predict outcome in patients with early-stag colorectal cancer. J Clin Oncol, 27:5944-5951.
Pandit-Taskar, Neeta First-in-Human Imaging with Zr-Df-IAB2M Anti-PSMA Minibody in Patients with Metastatic Prostate Cancer:

(56) References Cited

OTHER PUBLICATIONS

Pharmacokinetics, Biodistribution, Dosimetry, and Lesion Uptake, The Journal of Nuclear Medicine, vol. 57, No. 12, pp. 1858-1864, Dec. 2016.

Pardoll et al., 2012, Immunotherapy earns its spot in the ranks of cancer therapy. J Exp Med, 209(2):201-209. doi:10.1084/jem.20112275.

Park et al., 2017, Prediction of radio-responsiveness with immune-profiling in patients with rectal cancer, Oncotarget. 8:79793-79802.

Paul, 1993, Fundamental Immunology, 3d ed., Raven Press, Ltd. New York.

Pearson et al., Apr. 1988, Improved tools for biological sequence comparison, Proc. Nat'l. Acad. Sci. USA, 85:2444-2448.

Peng et al., Oct. 15, 2012, PD-1 Blockade Enhances T-cell Migration to Tumors by Elevating IFN-.gamma. Inducible Chemokines, Cancer Res, 72(20):5209-5218.

Perk, et al., 2006, Preparation and evaluation of (89)Zr-Zevalin for monitoring of (90)Y-Zevalin biodistribution with positron emission tomography. European Journal of Nuclear Medicine and Molecular Imaging, 33:1337.

Piittet et al.,, Jul. 24, 2007, In vivo imaging ofT cell delivery to tumors after adoptive transfer therapy. Proc Natl Acad Sci USA, 104(30):12457-12461.

Pillay V. et al., Sep. 2011, Antibodies in oncology. N Biotechnol, 28(5):518-529.

Predicted: late cornified envelope-like proline-rich protein 1 [Microtus ochrogaster]; NCBI Reference Sequence: XP_005367325.1; Reference bears a date of Aug. 7, 2015; however, as this item refers toa webpage, it may have been available in some form at an earlier date; Accessed, downloaded, and printed on Dec. 20, 2017.

Presta, Aug. 1992, Antibody engineering, Current Opinion in Biotechnology, 3(4):394-398.

Raag et al., Jan. 1995, Single-chain Fvs. FASEB J., 9(1):73-80.

Radiosynthesis Database of PET Probes, dated Mar. 31, 2017 accessed on the World Wide Web at < http://www.nirs.qst.go.jp/research/division/mic/db2/>, As this item refers to a webpage, it may have been available in some form at an earlier date.

Radu et al., 2007, Positron emission tomography with computed tomography imaging of neuroinflammation in experimental autoimmune encephalomyelitis., Proc Natl Acad Sci USA, 104(6):1937-1942.

Radu et al., 2008, Molecular imaging of lymphoid organs and immune activation by positron emission tomography with a new [18F]-labeled 2'-deoxycytidine analog, Nat Med, 14(7):783-780.

Randall et al., 2008, A dual-label technique for the immunohistochemical demonstration of T-lymphocyte subsets in formalin-fixed, paraffin-embedded rat lymphoid tissue. Toxicol Pathol, 36(6):795-804. doi:10.1177/0192623308322311.

Remington, The Science and Practice of Pharmacy 21st Edition, Pharmaceutical Press, London, Reprinted 2011, Copyrights 1889-2006.

Richardsen et al., 2008, The prognostic impact of M CSF, CSF 1 receptor, CD68 and CD3 in prostatic carcinoma. Histopathology, 53:30-38.

Riechmann et al., Mar. 1988, Reshaping human antibodies for therapy, Nature, 332:323-327.

Rizvi et al., 2012, Biodistribution, radiation dosimetry and scouting of 90Y-ibritumomab tiuxetan therapy in patients with relapsed B-cell non-Hodgkin's lymphoma using 89Zribritumomab tiuxetan and PET. European Journal of Nuclear Medicine and Molecular Imaging, 39:512.

Robert et al., 2011, Ipilimumab plus dacarbazine for previously untreated metastatic melanoma. N Engl J Med, 364(26):2517-2526 doi:10.1056/NEJMoa1104621.

Romer et al., 2011, Preculture of PBMCs at high cell density increases sensitivity of T-cell responses, revealing cytokine release by CD28 superagonist TGN1412. Blood, 118(26):6772-6782. doi:10.1182/blood-2010-12-319780.

Rossolini et al., Apr. 1994, Use of deoxyinosine-containing primers vs degenerate primers for polymerase chain reaction based on ambiguous sequence information, Molecular and Cellular Probes, 8(2):91-98.

Rothe et al., Sep. 2011, Recombinant proteins in rheumatology—recent advances. N Bioteehnol. 28(5):502-551.

Rudd et al., Jul. 2009, Inflammation imaging in atheroscleriosis. Arterioscler Thromb Vase Biol. 29(7):1009-1016.

Rudikoff et al., Mar. 1982, Single Amino Acid Substitution Altering Antigen-Binding Specificity, Proc. Natl. Acad. Sci. USA, 79:1979-1983.

Salgado et al., Feb. 2015, The evaluation of tumor-infiltrating lymphocytes (TILs) in breast cancer: recommendations by an International TILs Working Group 2014 Annals of Oncology, 26(2):259-271.

Saruta, M. et al., "Characterization of FOXP3+CD4+ regulatory T cells in Crohn's disease," Clinical Immunology, vol. 125, No. 3, pp. 281-290; 2007.

Sathaliyawala et al., 2013, Distribution and compartmentalization of human circulating and tissue-resident memory T cell subsets. Immunity, 38(1):187-197. doi:10.1016/j.immuni.2012.09.020.

Sato et al., 2005, Intraepithelial CD8+ tumor-infiltrating lymphocytes and a high CD8+/regulatory T cell ratio are associated with favorable prognosis in ovarian cancer. Proc Natl Acad Sci USA 102:18538-18543.

Schaefer, J. et al., Chapter 7: Miniantibodies In Knotermann & Duebel Antibody Engineering, vol. 2, pp. 85-100, (2010).

Sharif-Paghaleh et al., 2011, In vivo SPECT reporter gene imaging of regulatory T cells, PLoS One. 6(10):e25857.

Sharma et al., 2007, CD8 tumor-infiltrating lymphocytes are predictive of survival in muscle-invasive urothelial carcinoma. Proc Natl Acad Sci U S A, 104(10):3967-3972.

Sharma et al., Oct. 24, 2011, Novel cancer immunotherapy agents with survival benefit: recent successes and next steps. Nat Rev Cancer. 11(11):805-812. doi: 10.1038/nrc3153.

Sharon et al., Oct. 1, 2005, Recombinant polyclonal antibodies for cancer therapy,J Cell Biochem., 96(2):305-313.

Shore et al., 2008, The crystal structure ofCD8a.about.in complex with YTS156.7.7 Fab and interaction with other CDS antibodies define the binding mode of CD8a to MHC class I. J Mol Biol, 384(5):1190-1202.

Shultz et al., 2005, Human lymphoid and myeloid cell development in NOD.LtSz-scid IL2R gamma null mice engrafted with mobilized human hemopoietic stem cells. J Immunol., 174(10):6477-89.

Sirk et al., Dec. 2008, Site-specific, thiol-mediated conjugation of fluorescent probes to cysteine-modified diabodies targeting CD20 or HER2, 19(12):2527-2534.

Sljoka et al. Jul. 25-29, 2011, Predicting protein hinge motions and allostery using rigidity theory, International Conference on Applied Mathematics, Modeling & Computational Science, Waterloo, Canada, 4 pp.

Slovin, Jun. 2005, Targeting novel antigens for prostate cancer treatment: focus on prostate-specific membrane antigen, NIH Public Access: Author Manuscript, Expert Opinon Ther Targets, 9(3):561-570.

Smith and Waterman, 1981, Comparison of Biosequences, Adv. Appl. Math., 2,:482-489.

Stebbings et al., 2007, Cytokine storm in the phase I trial of monoclonal antibody TGN1412: better understanding the causes to improve preclinical testing of immunotherapeutics. J Immunol. 179(5):3325-31.

Stellhes et al., Mar. 1, 2008, Clinical molecular imaging in intestinal graft-versus-host disease: mapping of disease activity, prediction, and monitoring of treatment efficency by positron emission tomography. Blood. 111(5):2909-2918.

Stimmel et al., Sep. 29, 2000, Site-specific conjugation on serine → Cysteine variant monoclonal antibodies, The Journal of Biological Chemistry, 275(39):30445-30450.

Sundaresan Gobalakrishan et al., 2003, J-Labeled Engineered Anti-CEA Miniantibodies and Diabodies Allow High-Contrast, Antigen-Specific Small-Animal PET Imaging of Xenografts in Athymic Mice. The Journal of Nuclear Medicine, 44(12):1962-1969.

(56) References Cited

OTHER PUBLICATIONS

Tai et al., Dec. 1, 1995, Targeting c-erbB-2 expressing tumors using single-chain Fv monomers and dimers, Cancer Res., 55(23 Suppl.):5983s-5989s.
Tan, L. et al., Influence of the hinge region on complement activation, Ciq binding, and segmental flexibility in chimeric, Proc. Natl. Acad. Sci. USA; vol. 87, pp. 162-166, (1990).
Tavare et al., 2016, An Effective Immuno-PET Imaging Method to Monitor CD8-Dependent Responses to Immunotherapy Cancer Research 76(1):73-82.
Tavare, Dec. 2-6, 2012, Engineered Anti-Murine CD8 Minibody Fragment for Cu-64 ImmunoPET Imaging of CD8 Expression in Vivo, IBC's 23.sup.rd Annual International Conference, Diagnostic Antibody Engineering, Abstract No. F3. San Diego, CA.
Tefany et al., 1991, Immunocytochemical analysis of the cellular infiltrate in primary regressing and non-regressing malignant melanoma. J. Invest. Dermatol. 97:197-202.
Topalian et al., 2014, Survival, durable tumor remission, and long-term safety in patients with advanced melanoma receiving nivolumab. J Clin Oncol, 32(10):1020-1030. doi:10.1200/jco.2013. 53.0105.
Tumeh et al., 2008, PET Imaging of Cancer Immunotherapy, J. Uncl Med, 49(6):865-868.
Tumeh et al., 2014, PD-1 blockade induces responses by inhibiting adaptive immune resistance. Nature, 515(7528):568-571.
Urva et al., 2008, Physiologically based pharmacokinetic (PBPK) model for T.84.66, a monoclonal anti-CEA antibody, Am. Assoc. Pharm. Sci. 10(Supp. 2):957.
Vaidyanathan et al., 2009, Evaluation of an anti-p 185HER2 (scFv-CH2-CH2)2 fragment following radioiodination using two different residualizing labels: SGMIB and IB-Mal-D-GEEEK*, Nuclear Medicine and Biology, 36:671-680.
Vajdos et al., 2002, Comprehensive functional maps of the antigen-binding site of an anti-ErbB2 antibody obtained with shotgun scanning mutagenesis, J Mol Biol., 320(2):415-28.
Van Oijen et al., 2004, On the role of melanoma-specific CD8+ T-cell immunity in disease progression of advanced-stage melanoma patients. Clin Cancer Res., 10:4754-4760.
Verhaar et al., May 1996, Technetium-99m radiolabeling using a phage-derived single-chain Fv with a C-terminal cysteine, The Journal of Nuclear Medicine, 37(5):671-680.
Verhoeyen et al., 1988, Reshaping Human Antibodies: Grafting an Antilysozyme Activity, Science, 239:1534-1536.
Veri et al., Jul. 2010, Therapeutic control of B cell activation via recruitment of Fcgamma receptor llb (CD32B) inhibitory function with a novel bispecific antibody scaffold, Arthritis Rheum., 62(7):1933-1943.
Viola-Villegas et al., Nov. 3, 2014, Noninvasive Imaging of PSMA in Prostate Tumors with 89 Zr-Labeled huJ591 Engineered Antibody Fragments: The Faster Alternatives, Molecular Pharmaceutics, 11(11):3965-3973.
Vosjan et al., Apr. 2012, Nanobodies Targeting the Hepatocyte Growth Factor: Potential New Drugs for Molecular Cancer Therapy, Mol Cancer Ther, 11(4):1017-1025.
Wahlin et al., 2007, CD8+ T-Cell Content in Diagnostic Lymph Nodes Measured by Flow Cytometry is a Predictor of Survival in Follicular Lymphoma, Clin Cancer Res (2007), 13(2).
Wang, S., 2011, Advances in the production of human monoclonal antibodies, Antibody Technology Journal, 1:1-4.
Wang, X et al., Disulfide Scrambling in IgG2 Monoclonal Antibodies: Insights from Molecular Dynamics Simulations, Pharmacetuical Research, vol. 28, No. 12, pp. 3128-3144, (2011).
Westermann et al., 1992, Distribution of lymphocyte subsets and natural killer cells in the human body. Clin Investig, 70(7):539-544.
Whitlow et al., Aug. 1994, Multivalent Fvs: characterization of single-chain Fv oligomers and preparation of a bispecific Fv, Protein Engineering, 7(8):1017-1026.
Williamson et al., (1998). New monoclonal antibodies to the T cell antigens CD4 and CD8. Production and characterization in formalin-fixed paraffin-embedded tissue. Am J Pathol, 152(6):1421-1426.
Winkler et al., Oct. 15, 2000, Changing the Antigen Binding Specificity by Single Point Mutations of an Anti-p24 (HIV-1) Antibody, J. Immunol., 165(8):4505-4514.
Wolchok et al., 2009, Guidelines for the evaluation of immune therapy activity in solid tumors: immune-related response criteria. Clin Cancer Res, 15(23):7412-7420. doi:10.1158/1078-0432.ccr-09-1624.
Wong et al., Aug. 1, 2004, Pilot trial evaluating on 123I-Labeled 80-Kilodalton engineered anticarcinoembryonic antigen antibody fragment (cT84.66 minibody) in patients with colorectal cancer, Clinical Cancer Reasearch, 10:5014-5021.
Wu et al., 1970, An analysis of the sequences of the variable regions of Bence Jones proteins and myeloma light chains and their implications for antibody complementarity, J. Exp. Med. 132:211-250.
Wu et al., 1996, Tumor localization of anti-CEA single-chain Fvs: Improved targeting by non-convalent dimmers, Immunotechnology, 2:21-36.
Wu et al., 1999, Anti-carcinoembryonic antigen (CEA) diabody for rapid tumor targeting and imaging, Tumor Targeting, 4:47-58.
Wu et al., 2000, High-resolution microPET imaging of carcinoembryonic antigen-positive xenografts by using a copper-64-labeled engineered antibody fragment, Proc. Natl. Acad. Sci. USA, 97(15)8495-8500.
Wu et al., Jan. 2009, Antibodies and antimatter: The Resurgence of Immuno-PET, The Journal of Nuclear Medicine, 50(1):2-5.
Wu et al., Nov. 19, 1999, Humanization of a Murine Monoclonal Antibody by Simultaneous Optimization of Framework and CDR Residues, J. Mol. Biol. 294 (1):151-162.
Wu et al., Sep. 2005, Arming antibodies: prospects and challenges for immunoconjugates, Nature Biotechnology, 23( 9):1137-1146.
Yaghoubi et al., 2012, Positronemission tomography reporter genes and reporter probes: gene and cell therapy applications. Theranostics. 2(4):374-3.
Yamaguchi et al., Nov. 1, 2014, Development of a Sensitive Screening Method for Selecting Monoclonal Antibodies to be Internalized by Cells, Biochem. Biophys. Res. Commun. 454(4):600-603.
Yazaki et al., 2001, Mammalian expression and hollow fiber bioreactor production of recombinant anti-CEA diabody and minibody for clinical applications, Journal of Immunological Methods, 253:195-208.
Yazaki et al., 2001, Tumor targeting of radiometal labeled anti-CEA recombinant T84.66 diabody and T84.66 minibody: Comparison to radioiodinated fragments, Bioconjugate Chem., 12:220-228.
You et al., 1998, Expression, purification, and characterization of a two domain carcinoembryonic antigen minigene (N-A3) in pichia pastoris the essential role of the N-domain, Anticancer Research, 18:3193-3202.
Zhou et al., 2012, T-cell receptor gene transfer exclusively to human CD8+ cells enhances tumore cell killing, Blood, 120(22):4334-4342 and Supplemental pp. 1-6.
Ziai, 2018, CD8+ T cell infiltration in breast and colon cancer: A histologic and statistcal analysis, Plos One.
Preliminary Amendment filed on Dec. 21, 2011 in U.S. Appl. No. 12/788,477, filed May 27, 2012 in 9 pages.
Office Action dated Aug. 24, 2012 in U.S. Appl. No. 12/788,477, filed May 27, 2012 in 22 pages.
Written Opinion dated Apr. 23, 2008, from Int'l Appl. No. PCT/US2007/007020 (WO 07/109321).
Communication pursuant to Rules 70(2) and 70a(2) EPC dated Dec. 28, 2010, received in EP Appl. No. 08799192.3, 11 pages.
Written Opinion dated Apr. 22, 2009, from Int'l Appl. No. PCT/US2008/075291 (WO 09/032949).
Restriction Requirement dated Aug. 7, 2012 in U.S. Appl. No. 12/959,340.
Office Action dated Feb. 4, 2013 in U.S. Appl. No. 12/959,340.
Office Action dated Oct. 18, 2013 in U.S. Appl. No. 12/959,340.
Notice of Allowance dated Jan. 30, 2014 in U.S. Appl. No. 12/959,340.
Office Action dated Jan. 8, 2015 in Australian Application No. 2010325969.
Office Action dated Oct. 27, 2016 in Canadian Application No. 2,782,333.

(56) References Cited

OTHER PUBLICATIONS

Office Action dated Nov. 1, 2017 in Canadian Application No. 2782333.
Office Action dated Jun. 24, 2013 in Chinese Application No. 201080062988.4 (with English Translation).
Office Action dated Jan. 30, 2014 in Chinese Application No. 201080062988.4 with English Translation.
Office Action dated Jul. 7, 2014 in Chinese Application No. 201080062988.4 with English Translation.
Office Action dated Oct. 23, 2014 in Chinese Application No. 201080062988.4 with English Translation.
Office Action dated Dec. 28, 2017 in Chinese App. No. 201510333807.1.
Office Action dated Mar. 5, 2014 in European Application No. 10835159.4.
Communication pursuant to Article 94(3) EPC dated Aug. 26, 2014 in European Application No. 10835159.4.
Communication pursuant to Article 94(3) EPC dated Nov. 10, 2014 in European Application No. 10835159.4.
Summons to attend oral proceedings dated Jul. 10, 2015 in European Patent Application No. 10835159.4.
Extended European Search Report dated Jan. 18, 2017 in Application No. 16191132.6.
Office Action dated Dec. 20, 2017 in European Application No. 16191132.6.
Office Action dated Mar. 6, 2018 in Indian Patent App. No. 5792/DELNP/2012.
Office Action dated Feb. 23, 2015 in Japanese Application No. 2012-542204 with English translation.
Office Action dated Oct. 26, 2015, received in Japanese Patent Application No. 2012-542204 (with English translation).
Office Action dated Mar. 27, 2017 in Japanese Application No. 2012-542204 with English Translation.
Office Action dated Jan. 4, 2017 in Japanese Application No. 2016-34045 with English Translation.
Office Action dated Dec. 8, 2014 in Mexican Application No. MX/a/2012/006301 with English Translation.
Office Action dated Mar. 13, 2015 in Mexican Application No. MX/a/2012/006301 with English translation.
Office Action dated Sep. 5, 2016 in Mexican Application No. MX/a/2016/003128 with summary translation.
Office Action dated Nov. 16, 2016 in Mexican Application No. MX/a/2016/003128 with summary English Translation.
Office Action dated Jun. 9, 2017 in Mexican Application No. MX/a/2016/003128 with summary English Translation.
Office Action dated Apr. 24, 2013 in Russian Application No. 2012123550/20 (035853) (English Translation).
Office Action dated Dec. 9, 2014 in Russian Application No. 2012123550 with English Translation.
Office Action dated May 7, 2015 in Russian Application No. 2012123550 with English Translation.
Office Action dated Aug. 4, 2016 in Russian Application No. 2012123550 with English Translation.
Office Action dated Dec. 23, 2016 in Russian Application No. 2012123550 with English Translation.
Office Action dated Apr. 16, 2019 in European App. No. 14 779 573.6.
Office Action dated Feb. 6, 2018 in Japanese Patent App. No. 2016-501063, with English translation.
Office Action dated May 7, 2019 in Japanese Patent Application No. 2016-501063 with English Translation.
Office Action dated Jan. 4, 2017 in U.S. Appl. No. 14/773,710.
Office Action dated May 19, 2017 in U.S. Appl. No. 14/773,710.
Office Action dated Nov. 22, 2017 in U.S. Appl. No. 14/773,710.
Notice of Allowance dated May 10, 2018 in U.S. Appl. No. 14/773,710.
Notice of Allowance dated Sep. 17, 2018 in U.S. Appl. No. 14/773,710.
Notice of Allowance dated Mar. 27, 2019 in U.S. Appl. No. 14/773,710.
International Search Report and Written Opinion dated Aug. 1, 2014 in Application No. PCT/US14/22782.
Supplementary Partial Search Report dated May 3, 2016 in European Application No. 13804247.8.
Extended European Search Report dated Aug. 29, 2016 in Application No. 13804247.8.
Office Action dated Aug. 29, 2017 in European Application No. 13804247.8.
Office Action dated Jul. 28, 2015 in U.S. Appl. No. 14/407,440.
Office Action dated Feb. 22, 2016 in U.S. Appl. No. 14/407,440.
Office Action dated Sep. 14, 2016 in U.S. Appl. No. 14/407,440.
Office Action dated Mar. 9, 2017 in U.S. Appl. No. 14/407,440.
Office Action dated Nov. 1, 2017 in U.S. Appl. No. 14/407,440.
Office Action dated Mar. 13, 2018 in U.S. Appl. No. 14/407,440.
Final Office Action dated Aug. 1, 2018 in U.S. Appl. No. 14/407,440.
International Search Report and Written Opinion dated Nov. 15, 2013 in International Application No. PCT/US2013/045719.
International Search Report dated Oct. 14, 2013 in International Application No. PCT/US2013/053862.
Office action dated Mar. 28, 2018 in U.S. Appl. No. 15/228,616.
Amendment and response to non-final office action dated Jun. 18, 2018 in U.S. Appl. No. 15/228,616.
Office action dated Aug. 30, 2018 in U.S. Appl. No. 15/228,616.
Office action dated Dec. 27, 2018 in U.S. Appl. No. 15/228,616.
Amendment and response to non-final office action dated Mar. 25, 2019 in U.S. Appl. No. 15/228,616.
Office action dated Jun. 17, 2019 in U.S. Appl. No. 15/228,616.
Amendment and response to final office action dated Aug. 19, 2019 in U.S. Appl. No. 15/228,616.
Office action dated Oct. 22, 2019 in U.S. Appl. No. 15/228,616.
Response to non-final office action dated Jan. 26, 2020 in U.S. Appl. No. 15/228,616.
Office action dated Feb. 27, 2020 in U.S. Appl. No. 15/228,616.
Office Action dated Nov. 7, 2018 in Canadian Patent Application No. 2,994, 951.
Office Action dated Dec. 19, 2019 in Canadian Application No. 2,994,951.
Extended European Search Report dated Apr. 26, 2019 in European Patent Application No. 16835664.0.
Office Action dated Dec. 5, 2019 in European Application No. 16835664.0.
Office Action dated Apr. 1, 2019 in Japanese Patent Application No. 2018-526609.
Office Action dated Nov. 18, 2019 in Japanese Application No. 2018-526609 with English Translation.
First Examination Report dated Oct. 10, 2018 in New Zealand Patent Application No. 739721.
Examination Report dated May 28, 2019 in New Zealand Patent Application No. 739721.
Office Action dated Jul. 11, 2019 in Russian Patent Application No. 2018105374 with English Translation.
Office Action dated Mar. 11, 2020 in Russian Patent Application No. 2018105374 with English Translation.
International Search Report and Written Opinion, dated Jan. 5, 2017, in International Application No. PCT/US2016/045580.
International Search Report and Written Opinion, dated May 15, 2018, in International Application No. PCT/US2018/013117.
File History of U.S. Appl. No. 12/483,300.
File History of U.S. Appl. No. 14/419,225.
File History, U.S. Appl. No. 08/256,156, filed Jun. 24, 1994.
File History, U.S. Appl. No. 08/838,682, filed Apr. 9, 1997.
File History, U.S. Appl. No. 08/895,914, filed Jul. 17, 1997.
File History, U.S. Appl. No. 09/357,704, filed Jul. 20, 1999.
File History, U.S. Appl. No. 09/357,707, filed Jul. 20, 1999.
File History, U.S. Appl. No. 09/357,708, filed Jul. 20, 1999.
File History, U.S. Appl. No. 09/357,709, filed Jul. 20, 1999.
File History, U.S. Appl. No. 09/929,546, filed Aug. 13, 2001.
File History, U.S. Appl. No. 10/160,505, filed May 30, 2002.
File History, U.S. Appl. No. 10/449,379, filed May 30, 2003.
File History, U.S. Appl. No. 10/690,990, filed Oct. 23, 2003.
File History, U.S. Appl. No. 11/218,813, filed Sep. 2, 2005.
File History, U.S. Appl. No. 11/219,563, filed Sep. 2, 2005.
File History, U.S. Appl. No. 12/293,860, filed Sep. 22, 2008.

(56) References Cited

OTHER PUBLICATIONS

File History, U.S. Appl. No. 12/363,678, filed Jan. 30, 2009.
File History, U.S. Appl. No. 12/371,399, filed Feb. 13, 2009.
File History, U.S. Appl. No. 12/537,145, filed Aug. 6, 2009.
File History, U.S. Appl. No. 12/676,348, filed Aug. 5, 2010.
File History, U.S. Appl. No. 12/788,477, filed May 27, 2010.
File History, U.S. Appl. No. 12/959,340, filed Dec. 2, 2010.
File History, U.S. Appl. No. 13/554,306, filed Jul. 20, 2012.
File History, U.S. Appl. No. 15/228,616, filed Aug. 4, 2016.
Diamond et al., Sep. 1984, Somatic mutation of the T15 heavy chain gives rise to an antibody with autoantibody specificity, Proc. Natl. Acad. Sci. USA, 81:5841-5844.
Hasemann et al., 1991, Mutational analysis of arsonate binding by a CRIA+ antibody. VH and VL junctional diversity are essential for binding activity. Journal of Biological Chemistry, 266(12):7626-7632.
Jeger, ed., 1990, Clinical Immunology and Allergiology, translation from German, Moscow, Medicine, in 3 volumes, V.2, p. 484-485 [A Russian translation of ISBN-13: 978-3437112553 in German].
Ohno et. al., May 1985, Antigen-binding specificities of antibodies are primarily determined by seven residues of VH, Proc. Natl. Acad. Sci. USA, 82:2945-2949.
Paul ed., 1987, Immunology, in 3 volumes, translated from English, Moscow: Mir, 1987-1989, V.1 (1987), pp. 212-215 [A Russian translation of the 1st edition of Fundamental Immunology by William E. Paul.
Yarilin A.A., "Osnovy Immunologii" ("Basics of Immunology"), Moscow.: Medicine, 1999, pp. 176-177 [a reference in Russian].
Amendment, Response to Final Office Action and Request for Continued Examination (RCE) dated May 22, 2020 in U.S. Appl. No. 15/228,616.
Amendment and Response to Non-Final Office Action dated Oct. 22, 2020 in U.S. Appl. No. 15/228,616.
Office Action dated Dec. 16, 2020 in U.S. Appl. No. 15/228,616.
Office Action dated Jan. 7, 2021 in Canadian Application No. 2,994,951.
Notification of the First Office Action dated Nov. 12, 2020 in Chinese patent application No. 2016800583411.
Office Action dated Aug. 24, 2020 in European Application No. 16835664.0.
Pre-Appeal Examination Report dated Apr. 22, 2020 in Japanese Application No. 2018-526609 with English Translation.
Office Action dated Aug. 10, 2020 in Russian Patent Application No. 2018105374 with English Translation.
Angal et al., 1993, A single amino acid substitution abolishes the heterogeneity of chimeric mouse/human (IgG4) antibody. Molecular Immunology, 30(1):105-108.
Chiu et al., Dec. 3, 2019, Antibody Structure and Function: The Basis for Engineering Therapeutics, Antibodies 8:55:1-80.
Amendment and Response to Final Office Action and Request for Continued Examination dated Mar. 15, 2021 in U.S. Appl. No. 15/228,616.
Office Action dated Apr. 5, 2021 in U.S. Appl. No. 15/228,616.
Amendment and Response to Action dated Jun. 30, 2021 in U.S. Appl. No. 15/228,616.
Search Report dated Jan. 19, 2021 in Brazilian patent application No. BR112018002451-1.
Notification of the Second Office Action dated Jul. 5, 2021 in Chinese patent application No. 2016800583411.
Notice of Reasons for Rejection dated May 10, 2021, in Japanese Application No. 2018-526609.
Notice of Reasons for Rejection dated May 17, 2021, in Japanese Application No. 2020-047973.
Office Action dated Apr. 9, 2021 in Russian Patent Application No. 2018105374.
ImaginAb, Jul. 2018, Accelerating Immuno-Oncology Beyond Biopsy, PowerPoint presentation, 79 pp.
Gordon, Imaging of tumor infiltrating T cells with an anti-CD8 minibody 89Zr-IAB22M2C in advanced solid tumors: a phase 1 first-in-human study, PowerPoint presentation, 14 pp., Oct. 2018.
Gordon, Imaging of tumor infiltrating T cells with an anti-CD8 minibody 89Zr-IAB22M2C in advanced solid tumors: a phase 1 first-in-human study, Abstract, 5 pp., Sep. 2018.
ImaginAb, Apr. 2019, Accelerating Immuno-Oncology through Imaging Immune System, PowerPoint presentation, 28 pp.
ImaginAb, ASCO Meeting, PowerPoint presentation, 30 pp., 2019.
ImaginAb, Better biomarkers will be able to predict efficacy, photo with PowerPoint slide, 1 p., ASCO-SITC Clinical Immuno-Oncology Symposium, 2018.
ImaginAb, Jun. 18, 2018, CD8 ImmunoPET accelerating immuno-oncology, PowerPoint presentation, 26 pp.
ImaginAb, Jun. 2018, Accelerating Immuno-Oncology Beyond Biopsy, PowerPoint presentation, 19 pp.
ImaginAb, Jun. 2019, Non-confidential Investment Presentation, PowerPoint presentation, 34 pp.
ImaginAb, Jun. 1, 2018, CD8 ImmunoPET accelerating immuno-oncology, PowerPoint presentation, 26 pp.
ImaginAb, May 2019, Non-confidential Investment Presentation, PowerPoint presentation, 32 pp.
ImaginAb, Nov. 2018, Accelerating Immuno-Oncology through Imaging Immune System, PowerPoint presentation, 20 pp.
ImaginAb, Oct. 11, 2018, In vivo clinical PET imaging of CD8 T cells using the Zr89 minibody IAB22M2C, Advances in Immuno-Oncology USA Congress, PowerPoint presentation, 17 pp.
ImaginAb, Patient 2—Subject: 64 years old, male metastatic hepatocellular carcinoma, PowerPoint slide, 1 p., ASCO, Jun. 2018.
ImaginAb, Unlocking the immune system for cancer therapy, PowerPoint presentation, 18 pp., Feb. 2018.
ImaginAb, Improvement on Radiolabeling Process for Zr-89 labeled CD8 Tracer, SNMMI Abstract, 2019.
Joshi et al., PET scanner harmonization for multi-center clinical trials using 89Zr tracers in partnership with clinical trials network (CTN), Poster No. 1201, 1 p., 2019.
Notice of Allowance dated Aug. 20, 2021 in U.S. Appl. No. 15/228,616.
Notice of Reasons for Rejection dated Aug. 23, 2021, in Japanese Application No. 2018-526609.
Pandit-Tasker, First in human phase 1 imaging study with 89Zr-Df-IAB22M2C anti-CD8 minibody in patients with solid tumors, PowerPoint presentation, 15 pp., SNMMI, 2018.
Pandit-Tasker, First in human trial of 89Zr-Dr-IAB22M2C anti-CD8 minibody in patients with solid tumors, PowerPoint presentation, 18 pp., WMIC, 2018.
Pandit-Tasker, First-in-human imaging with $^{89}$Zr-Df-IAB22M2C anti-CD8 minibody in patients with solid malignancies: preliminary pharmacokinetics, biodistribution, and lesion targeting, 2019. 32 pp.
Wu, May 2, 2016, Zr-labeled antibodies and fragments for imaging immune cells, NCI/SNMM/CTN Immune Modulation Therapy and Imaging Workshop, Shady Grove, MD, PowerPoint presentation, 349 pp.
U.S. Appl. No. 17/454,938, filed Nov. 15, 2021, Chan et al.
Notice of Allowance dated Oct. 27, 2021 in U.S. Appl. No. 15/228,616 in 12 pages.
Corrected Notice of Allowability, dated Nov. 12, 2021 in U.S. Appl. No. 15/228,616.
Official Filing Receipt received Dec. 6, 2021 in U.S. Appl. No. 17/454,938 in 3 pages.
Office Action with English Translation dated Nov. 25, 2021 in Japanese Application No. 2020-047973.
Office Action dated Dec. 13, 2021, in Canadian Patent Application No. 2,994, 951.
Office Action with English translation dated Dec. 30, 2021, in Chinese Patent Application No. 2016800583411.
Corrected Notice of Allowability dated Dec. 30, 2021, in U.S. Appl. No. 15/228,616.

\* cited by examiner

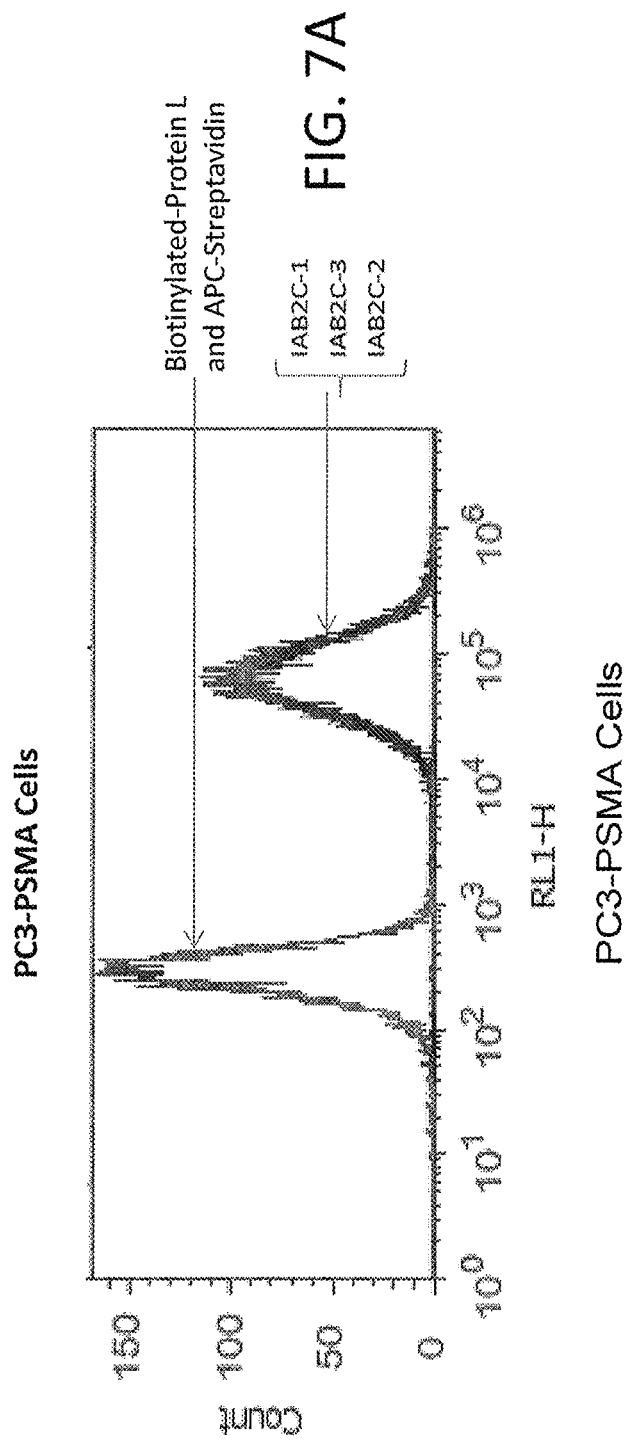
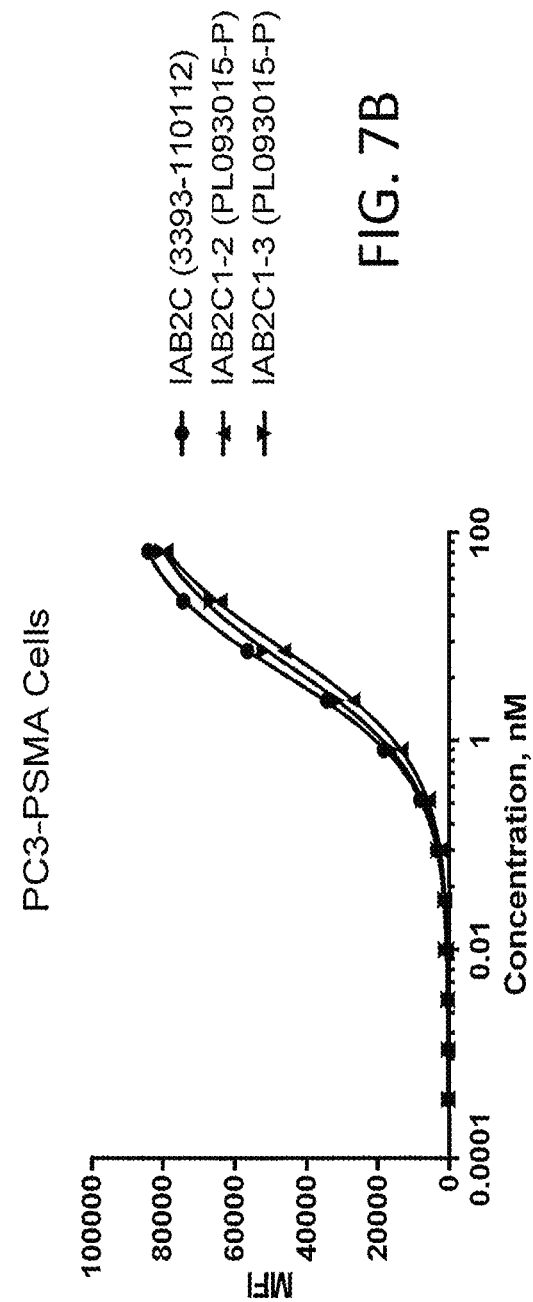
FIG. 7A
FIG. 7B

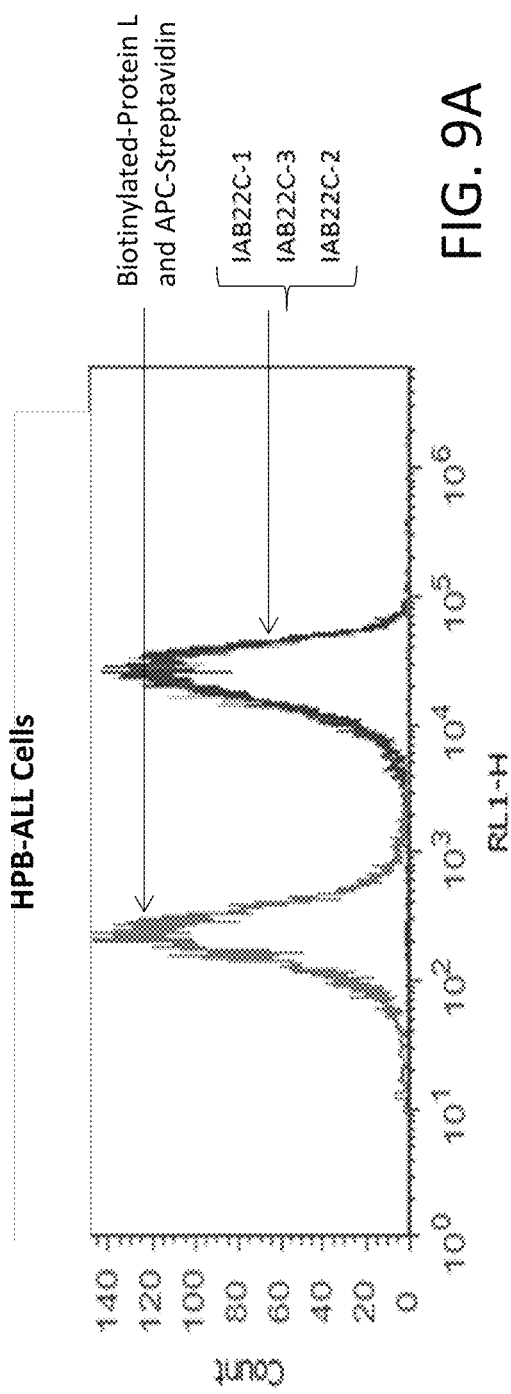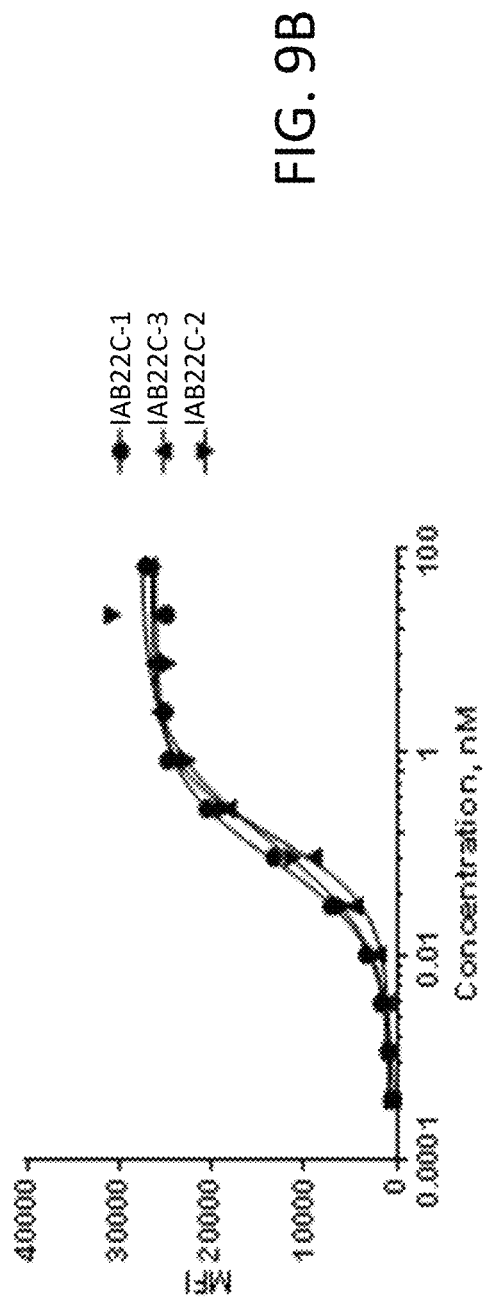

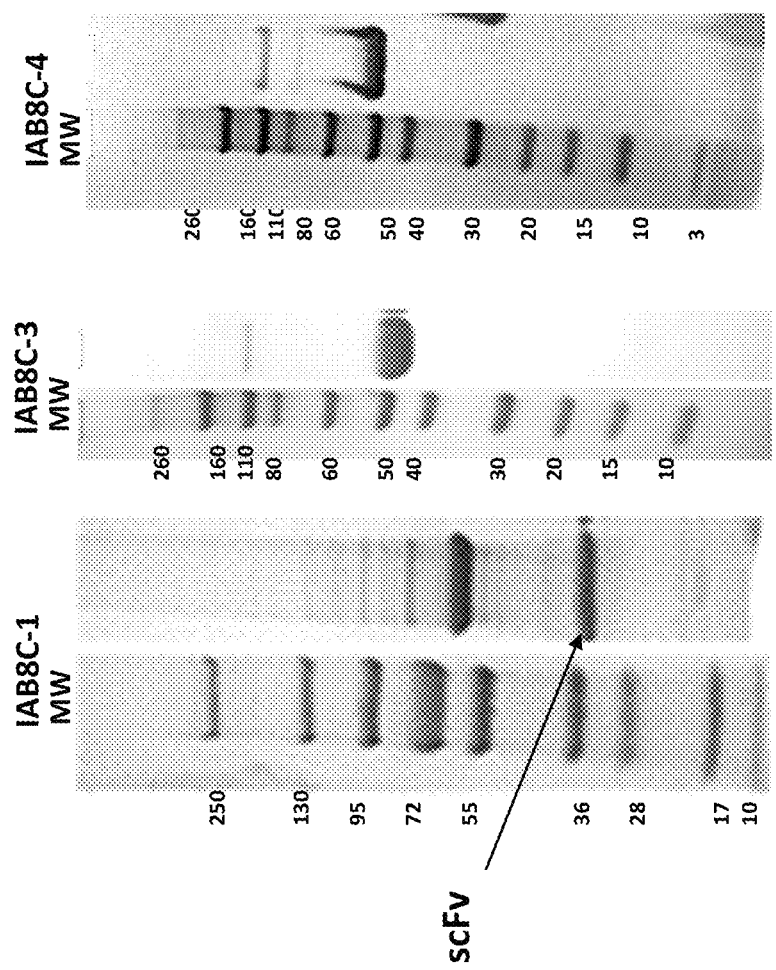

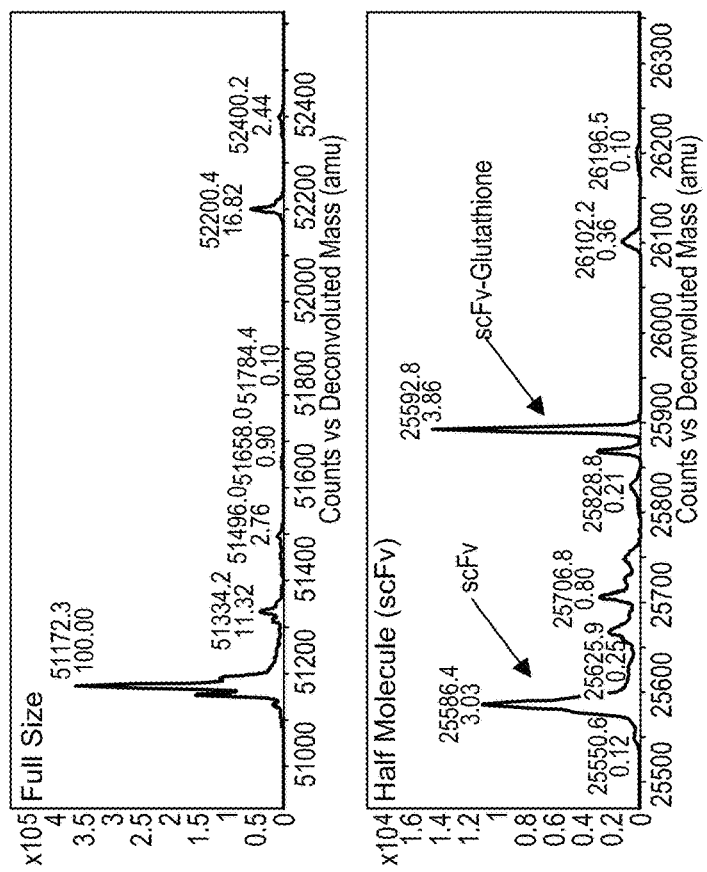
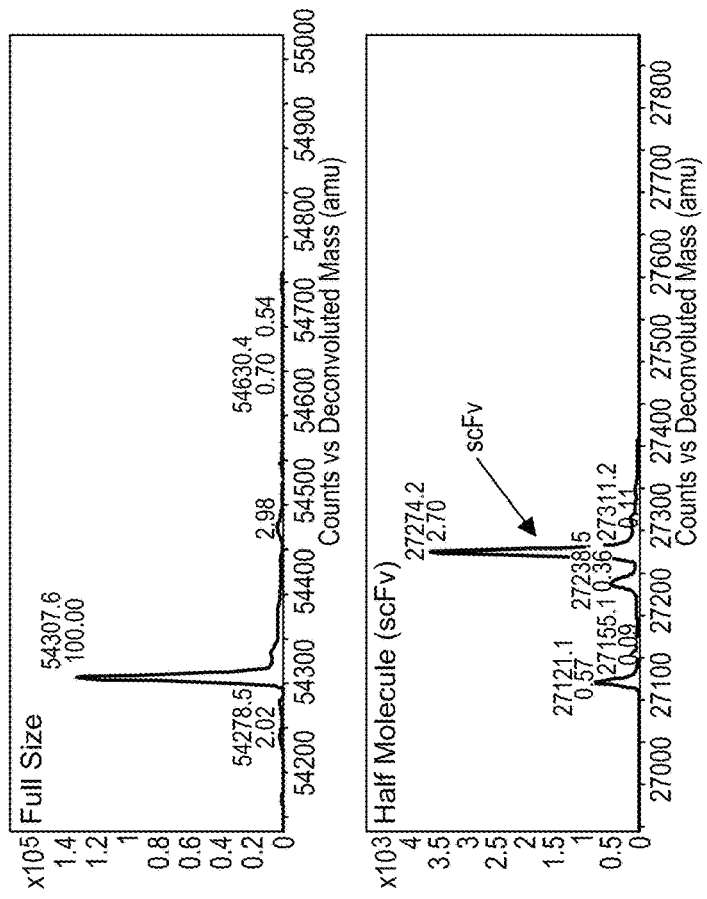
FIG. 14A
FIG. 14B

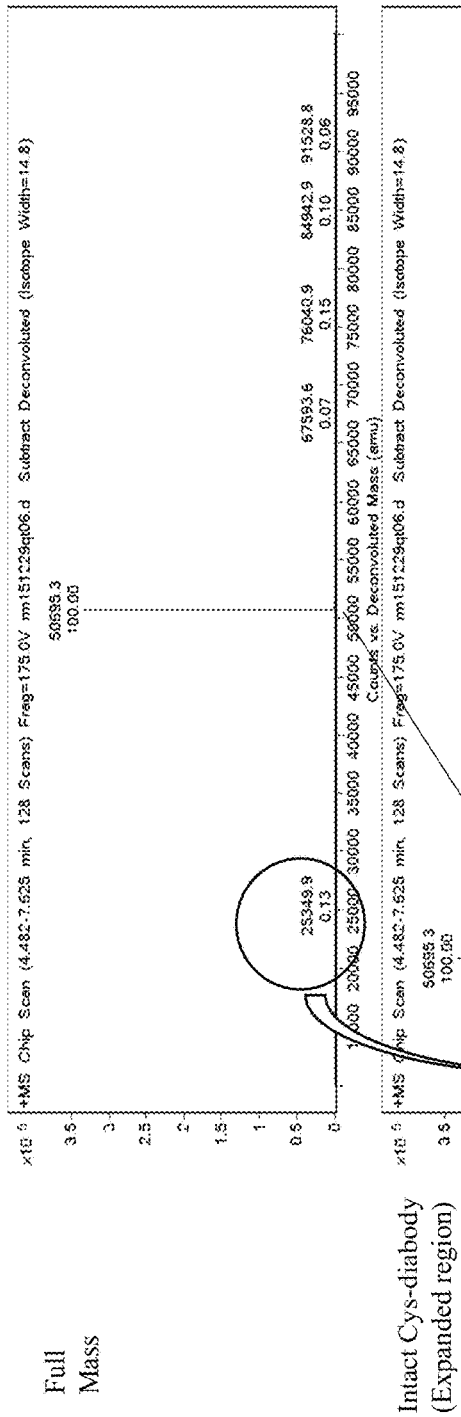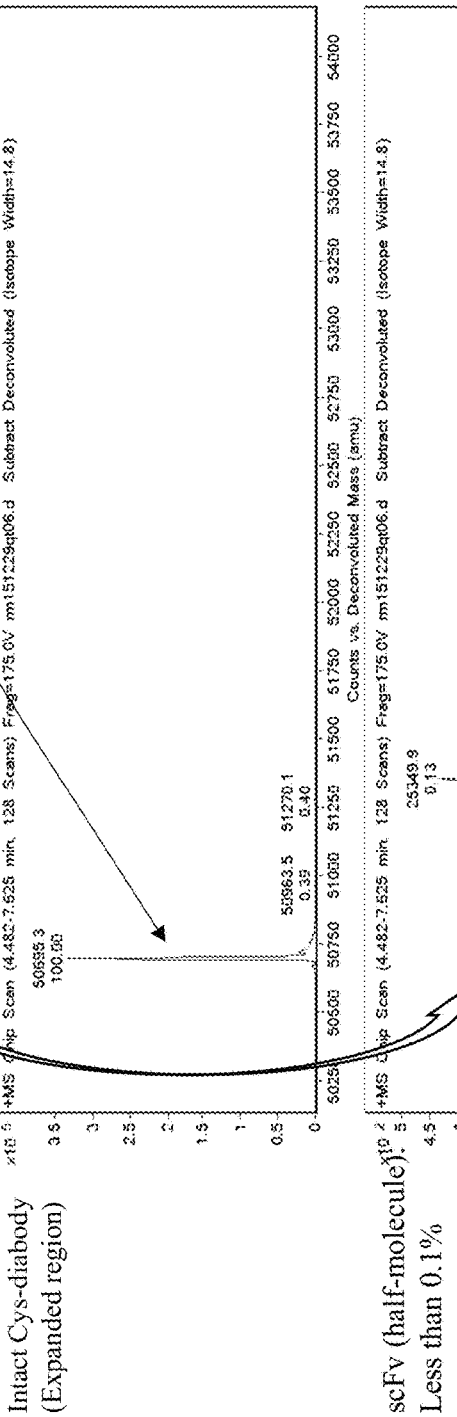
FIG. 15A  FIG. 15B  FIG. 15C

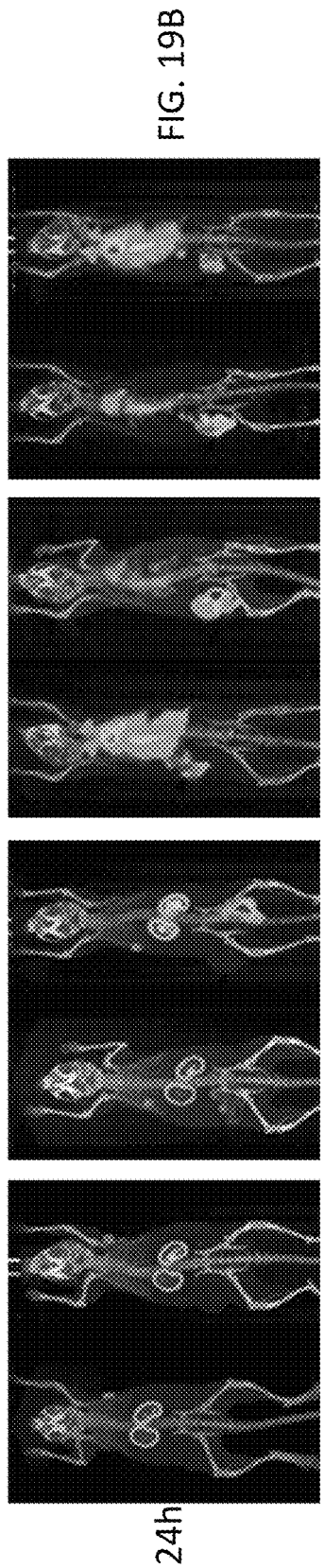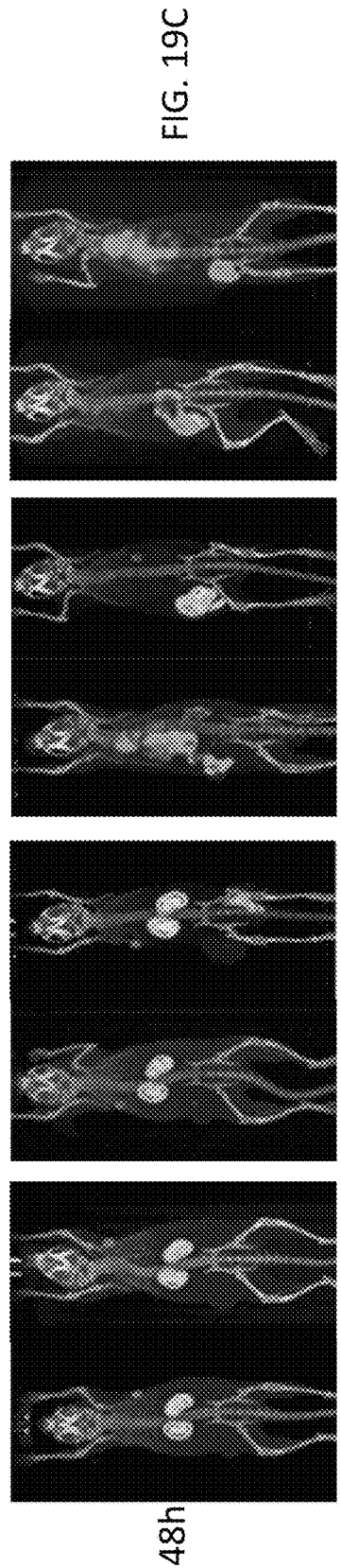

IAB22C-1:

DVQITQSPSSLSASVGDRVTITCRTSRSISQYLAWYQQKPGKVP
KLLIYSGSTLQSGVPSRFSGSGSGTDFTLTISSLQPEDVATYYC
QQHNENPLTFGGGTKVEIKGGGSGGGGSGGGGEVQLVESGGGLVQPGGS
LRLSCAASGFNIKDTYIHFVRQAPGKGLEWIGRIDPANDNTLYA
SKFQGKATISADTSKNTAYLQMNSLRAEDTAVYYCGRGYGYYVF
DHWGQGTLVTVSSGGC (SEQ ID NO: 161)

FIG. 22

IAB22C-2:
DVQITQSPSSLSASVGDRVTITCRTSRSISQYLAWYQQKPGKVPKLLIYSG
STLQSGVPSRFSGSGSGTDFTLTISSLQPEDVATYYCQQHNENPLTFGGGT
KVEIKSGGGGEVQLVESGGGLVQPGGSLRLSCAASGFNIKDTYIHFVRQAP
GKGLEWIGRIDPANDNTLYASKFQGKATISADTSKNTAYLQMNSLRAEDTA
VYYCGRGYGYYVFDHWGQGTLVTVSSGGCPPC (SEQ ID NO: 162)

FIG. 23

IAB22C-3:
DVQITQSPSSLSASVGDRVTITCRTSRSISQYLAWYQQKPGKVPKLLIYSG
STLQSGVPSRFSGSGSGTDFTLTISSLQPEDVATYYCQQHNENPLTFGGGT
KVEIKSGGGGEVQLVESGGGLVQPGGSLRLSCAASGFNIKDTYIHFVRQAP
GKGLEWIGRIDPANDNTLYASKFQGKATISADTSKNTAYLQMNSLRAEDTA
VYYCGRGYGYYVFDHWGQGTLVTVSSGGCPPCPPC (SEQ ID NO: 163)

FIG. 24

EXTENSION SEQUENCES FOR DIABODIES

CROSS REFERENCE TO RELATED APPLICATIONS

This Application claims the benefit of U.S. Provisional Application No. 62/456,252, filed Feb. 8, 2017, which is incorporated herein by reference in its entirety.

The present application is being filed along with a Sequence Listing in electronic format. The Sequence Listing is provided as a file entitled IGNAB043ASEQLIST.TXT, created on Jan. 10, 2018, which is 61,428 bytes in size. The information in the electronic format of the Sequence Listing is incorporated herein by reference in its entirety.

BACKGROUND

Field

Embodiments described herein relate generally to extension sequences.

Description of the Related Art

Various antigen binding constructs exist. Some such constructs include diabodies. Diabodies contain a $V_L$ domain associated with a $V_H$ domain.

SUMMARY OF THE INVENTION

In some embodiments, a diabody is provided that comprises a heavy chain variable domain, a light chain variable domain, a linker that links the heavy chain variable domain to the light chain variable domain, and an extension sequence. The extension sequence can be selected from the group consisting of: EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPCPPC (SEQ ID NO: 5), and GGC(PPC)$_n$ (SEQ ID NO: 11), wherein n is 2, 3, 4, 5, 6, 7, 8, or 9, wherein X$_{n1}$, X$_{n2}$, X$_{n3}$, X$_{n4}$, and X$_{n5}$ can be any amino acid. The linker connects $V_H$ to $V_L$ through its peptide backbone, while the extension sequence can connect $V_H$ to $V_H$ or $V_L$ to $V_L$ through a disulfide bond.

In some embodiments, a diabody comprising a heavy chain variable domain, a light chain variable domain a linker that links the heavy chain variable domain to the light chain variable domain, and an extension sequence attached to either the heavy chain variable domain or the light chain variable domain is provided. The extension sequence comprises CPPCPPCPPC (SEQ ID NO: 6).

In some embodiments, a method of manufacturing a diabody as provided herein can comprise providing yeast or a mammalian cell comprising a nucleic acid sequence encoding a diabody; and expressing the diabody as described herein.

In some embodiments, an extension sequence configured for use within an antigen binding construct is provided. The extension sequence is selected from the group consisting of: EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPCPPC (SEQ ID NO: 5), and GGC(PPC)$_n$ (SEQ ID NO: 11), wherein n is 2, 3, 4, 5, 6, 7, 8, or 9, wherein X$_{n1}$, X$_{n2}$, X$_{n3}$, X$_{n4}$, and X$_{n5}$ can be any amino acid.

In some embodiments, a diabody is provided. The diabody can comprise a first heavy chain variable domain, a first light chain variable domain, a first linker that connects the first heavy chain variable domain and the first light chain variable domain, a second heavy chain variable domain, a second light chain variable domain, a second linker that connects the second heavy and second light chain variable domains, and at least two extension sequences that covalently connect either a) the first heavy chain variable domain to the second heavy chain variable or b) the first light chain variable domain to the second light chain variable domain. The extension sequence can be selected from the group consisting of: EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPCPPC (SEQ ID NO: 5), and GGC(PPC)$_n$ (SEQ ID NO: 11), wherein n is 1, 2, 3, 4, 5, 6, 7, 8, or 9. X$_{n1}$, X$_{n2}$, X$_{n3}$, X$_{n4}$, and X$_{n5}$ can be any amino acid. The linker connects $V_H$ to $V_L$ through its peptide backbone, while the extension sequence can connect $V_H$ to $V_H$ or $V_L$ to $V_L$ through a disulfide bond.

In some embodiments, a cell line is provided that produces any of the diabodies disclosed herein.

In some embodiments, a kit is provided that comprises any of the diabodies disclosed herein and a detectable marker.

In some embodiments, a method of manufacturing any of the diabodies disclosed herein is provided comprising providing yeast or mammalian cells comprising a nucleic acid encoding the diabody and expressing the diabody.

In some embodiments, an extension sequence is provided that is configured for use within an antigen binding construct, wherein the extension sequence is selected from the group consisting of: EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2); ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPCPPC (SEQ ID NO: 5), and GGC(PPC)$_n$ (SEQ ID NO: 11), wherein n is 2, 3, 4, 5, 6, 7, 8, or 9, wherein X$_{n1}$, X$_{n2}$, X$_{n3}$, X$_{n4}$, and X$_{n5}$ can be any amino acid.

In some embodiments, a method of detecting a presence or absence of a marker is provided, the method comprising: applying any of the diabodies disclosed herein to a sample; and detecting the presence or absence of the marker.

In some embodiments, a pharmaceutical composition is provided comprising any of the extension sequences disclosed herein. In some embodiments, a pharmaceutical composition is provided comprising any of the diabodies disclosed herein.

In some embodiments, a method of treatment is provided comprising: administering a therapeutically effective amount of any pharmaceutical composition disclosed herein.

In some embodiments, a nucleic acid is provided that encodes for any diabody described herein. In some embodiments, a nucleic acid is provided that encodes for any extension sequence described herein.

In some embodiments, a vector comprising any of the nucleic acids disclosed herein is provided.

In some embodiments, a diabody comprising two chains is provided. The first chain comprises a first heavy chain variable domain, a first light chain variable domain, a first linker that connects the first heavy chain variable domain and the first light chain variable domains, and a first extension sequence. The diabody further comprises a second chain that comprises a second heavy chain variable domain, a second light chain variable domain, a second linker that connects the second heavy and second light chain variable domains, and a second extension sequence. The first extension sequence and the second extension sequence are covalently connected to one another. The first extension sequence and the second extension sequence are selected from the group consisting of: EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3)$_n$, ESKYGPPCX$_{n1}$X$_{n2}$CX$_{n3}$X$_{n4}$C (SEQ ID NO: 4), CPPCPPC (SEQ ID NO: 5), and GGC(PPC)$_n$ (SEQ ID NO: 11), wherein n is 2, 3, 4, 5, 6, 7, 8, or 9, wherein X$_{n1}$, X$_{n2}$, X$_{n3}$, X$_{n4}$, and X$_{n5}$ can be any amino acid. The linker connects V$_H$ to V$_L$ through its peptide backbone, while the extension sequence can connect V$_H$ to V$_H$ or V$_L$ to V$_L$ through a disulfide bond.

In some embodiments, diabodies comprising one or more of the extension sequences can be used in the treatment of a subject in need of treatment with a diabody directed to a specific target.

BRIEF DESCRIPTION OF THE DRAWINGS

FIG. 7A depicts peaks showing binding of the IAB2C-1, IAB2C-2, and IAB2C-3 constructs to PSMA expressed on the surface of PC3-PSMA cells.

FIG. 7B depicts a graph that compares binding of the IAB2C-1, IAB2C-2, and IAB2C-3 constructs to PSMA at different concentrations of the constructs.

FIG. 9A depicts peaks showing binding of the IAB22C-1, IAB22C-2, and IAB22C-3 constructs to CD8 expressed on the surface of HPB-ALL cells.

FIG. 9B depicts a graph that compares binding of the IAB22C-1, IAB22C-2, and IAB22C-3 constructs to CD8 at different concentrations of the constructs.

FIG. 10A depicts an SDS-PAGE gel that shows bands that correspond to both an intact Cys-diabody and a single chain fragment variable derived from the IAB8C-1 construct.

FIG. 10B depicts an SDS-PAGE gel that shows bands that correspond to an intact Cys-diabody from the IAB8C-3 construct with no detectable scFv.

FIG. 10C depicts an SDS-PAGE gel that shows bands that correspond to an intact Cys-diabody from the IAB8C-4 construct with no detectable scFv.

FIG. 14A depicts Mass Spectrometry analysis of the full and half molecule of IAB1C-1.

FIG. 14B depicts Mass Spectrometry analysis of the full and half molecule of IAB20C-1.

FIG. 15A depicts Mass Spectrometry analysis of the IAB2C-3 intact diabody.

FIG. 15B depicts Mass Spectrometry analysis of the relevant expanded region of the IAB2C-3 intact diabody.

FIG. 15C depicts Mass Spectrometry analysis of the IAB2C-3 single chain fragment variable.

FIG. 19A depicts images showing distribution of $^{89}$Zr-DF-IABDBC-1, $^{89}$Zr-DF-IABDBC-1-10kPEG, $^{89}$Zr-DF-IABDBC-4-10kPEG, and $^{89}$Zr-DF-IABDBC-4-20kPEG 4 hours after injection of the construct.

FIG. 19B depicts images showing distribution $^{89}$Zr-DF-IABDBC-1, $^{89}$Zr-DF-IABDBC-1-10kPEG, $^{89}$Zr-DF-IABDBC-4-10kPEG, $^{89}$Zr-DF-IABDBC-4-20kPEG 24 hours after injection of the construct.

FIG. 19C depicts images showing distribution $^{89}$Zr-DF-IABDBC-1, $^{89}$Zr-DF-IABDBC-1-10kPEG, $^{89}$Zr-DF-IABDBC-4-10kPEG, $^{89}$Zr-DF-IABDBC-4-20kPEG 48 hours after injection.

FIG. 22 is an amino acid sequence of a diabody construct of IAB22C-1, having a sequence comprising GGC.

FIG. 23 is an amino acid sequence of a diabody construct of IAB22C-2, having a sequence comprising CPPC.

FIG. 24 is an amino acid sequence of a diabody construct of IAB22C-3, having a sequence comprising CPPCPPC.

DETAILED DESCRIPTION

Figure 1:
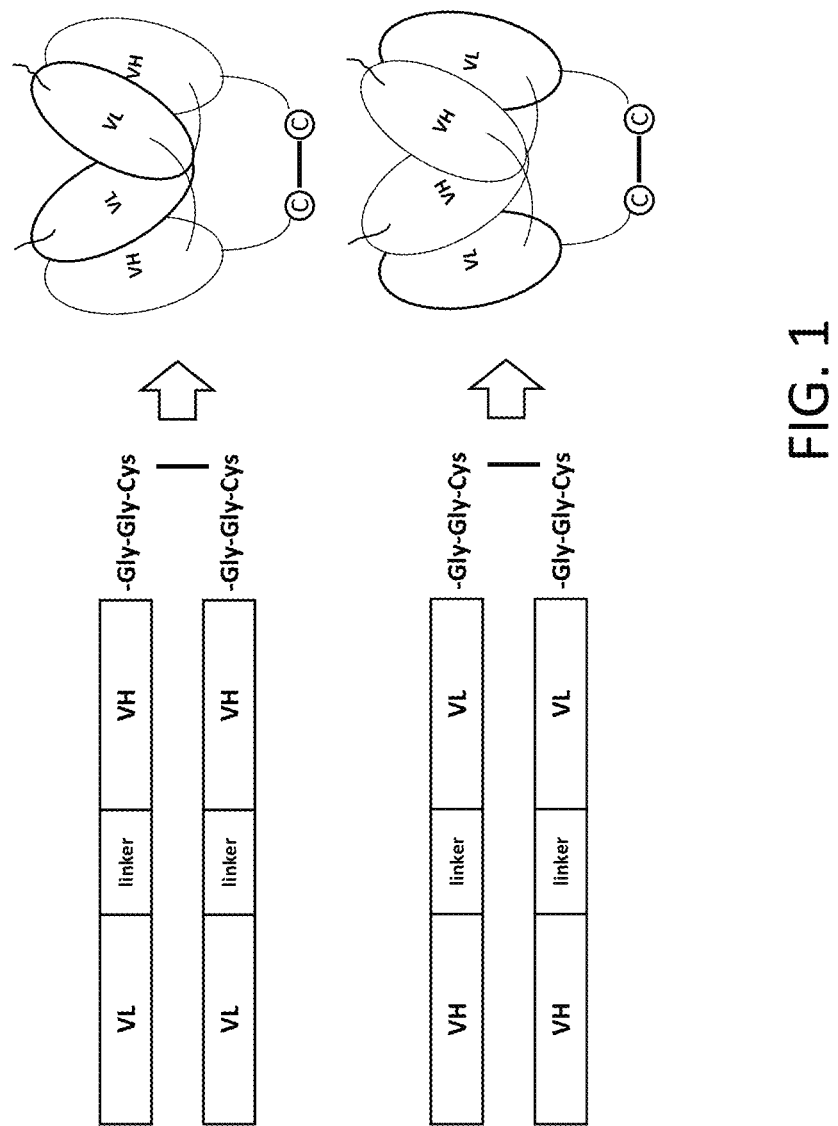
FIG. 1 depicts a Cys-diabody that contains a single Cys-Cys bridge at the C-terminus.

Described herein are components of antigen binding constructs, including, for example, diabodies. These diabodies can include a heavy chain variable domain, a light chain variable domain, a linker, and an extension sequence. The linker connects $V_H$ to $V_L$ through its peptide backbone, while the extension sequence can connect $V_H$ to $V_H$ or $V_L$ to $V_L$ through a (meaning one or more) disulfide bond(s). In some embodiments, specific extension sequences are employed in diabodies. In some embodiments, the extension sequences provide various benefits when they are associated with diabodies. In some embodiments, the benefits of extension sequences can include one or more of, but are not limited to, (i) increasing the stability of diabodies, (ii) reducing the impurities consisting of the single chain fragment variable, and (iii) increasing the proper assembly of bispecific diabodies. Also described herein are extension sequences that are associated with antigen binding constructs. In some embodiments, the extension sequence allows for additional cysteines for attaching moieties such as cytotoxic drugs, chelators and/or PEGs while maintaining the overall stability and characteristics of the protein.

Definitions

The term "diabody" denotes a dimer that comprises heavy chain ($V_H$) domains and light-chain variable ($V_L$) domains. Each heavy chain domain is connected to a light chain domain through a linker.

The term "linker" denotes a peptide sequence that connects the $V_H$ and $V_L$ domains. Linkers can orient the $V_H$ and $V_L$ domains in either a $V_L$-$V_H$ or $V_H$-$V_L$ orientation. The linker connects $V_H$ to $V_L$ through its peptide backbone.

The term "extension sequence" denotes a region that connects a first $V_H$ domain to a second $V_H$ domain or a first $V_L$ to a second $V_L$ domain, in for example, a diabody. Extension sequences can connect the domains through the C-terminus of each domain. In some embodiments, extension sequences connect the domains through covalent bonds. In some embodiments, the extension sequence will include one or more cysteine, allowing for one or more disulfide bonds to be formed between two such extension sequences. An example of a pair of extension sequences is shown as the line with two cysteines connecting either the two heavy chain domains or the two light chain domains. While the extension sequence will be towards the C-terminus of the constructs in FIG. 1, it need not be the absolute last amino acid in the variable domain. That is, the linker can be positioned slightly N-terminal to the C-terminus. For example, the extension sequence can be placed within the 10 amino acids at the C-terminus. Similarly, additional sequence can be placed between the native C-terminus and where the extension sequence starts. The extension sequence can connect $V_H$ to $V_H$ or $V_L$ to $V_L$ through a disulfide bond The term "treating" or "treatment" of a condition can include preventing the condition, slowing the onset and/or rate of development of the condition, reducing the risk of developing the condition, preventing and/or delaying the development of symptoms associated with the condition, reducing or ending symptoms associated with the condition, generating a complete or partial regression of the condition, or some combination thereof. The term "prevent" does not require the absolute prohibition of the disorder or disease.

A "therapeutically effective amount" or a "therapeutically effective dose" is an amount that produces a desired therapeutic effect in a subject, such as preventing, treating a target condition, delaying the onset of the disorder and/or symptoms, and/or alleviating symptoms associated with the condition. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and/or the route of administration. One skilled in the clinical and pharmacological arts will be able to determine a therapeutically effective amount through routine experimentation, for example by monitoring a subject's response to administration of a compound and adjusting the dosage accordingly, given the present disclosure. For additional guidance, see Remington: The Science and Practice of Pharmacy 21st Edition, Univ. of Sciences in Philadelphia (USIP), Lippincott Williams & Wilkins, Philadelphia, Pa., 2005.

The term "antigen binding construct" includes all varieties of antibodies, including binding fragments thereof. Further included are constructs that include 1, 2, 3, 4, 5, and/or 6 CDRs. In some embodiments, tandem scFvs can be provided, which can provide two arms with bivalent binding. In some embodiments, these CDRs can be distributed between their appropriate framework regions in a traditional antibody. In some embodiments, the CDRs can be contained within a heavy and/or light chain variable region. In some embodiments, the CDRs can be within a heavy chain and/or a light chain. In some embodiments, the CDRs can be within a single peptide chain. Unless otherwise denoted herein, the antigen binding constructs described herein bind to the noted target molecule. The term "target" or "target molecule" denotes the protein to which the antigen binding construct binds.

The term "antibody" includes, but is not limited to, genetically engineered or otherwise modified forms of immunoglobulins, such as intrabodies, chimeric antibodies, fully human antibodies, humanized antibodies, antibody fragments, scFv, and heteroconjugate antibodies (for example, bispecific antibodies, diabodies, triabodies, tetrabodies, etc.). The term "antibody" includes scFv and minibodies. Thus, each and every embodiment provided herein in regard to "antibodies" is also envisioned as scFv and/or minibody embodiments, unless explicitly denoted otherwise. The term "antibody" includes a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. In some embodiments, a full length antibody can be composed of two identical pairs of polypeptide chains, each pair having one "light" and one "heavy" chain (connected through a disulfide bond). The recognized immunoglobulin genes include the kappa, lambda, alpha, gamma, delta, epsilon, hinge, and mu constant region genes, as well as the myriad immunoglobulin variable region genes. For full length chains, the light chains are classified as either kappa or lambda. For full length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this application, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (for example, F(ab')2) with the same binding specificity. In some embodiments, the antibody binds specifically to a desired target.

An "antibody variable light chain" or an "antibody variable heavy chain" as used herein refers to a polypeptide comprising the VL or VH, respectively. The endogenous VL is encoded by the gene segments V (variable) and J (junctional), and the endogenous VH by V, D (diversity), and J. Each of VL or VH includes the CDRs as well as the framework regions. In this application, antibody variable light chains and/or antibody variable heavy chains may, from time to time, be collectively referred to as "antibody chains." These terms encompass antibody chains containing mutations that do not disrupt the basic structure of VL or VH, as one skilled in the art will readily recognize. In some embodiments, full length heavy and/or light chains are contemplated. In some embodiments, only the variable region of the heavy and/or light chains are contemplated as being present.

Antibodies can exist as intact immunoglobulins or as a number of fragments produced by digestion with various peptidases. Thus, for example, pepsin digests an antibody below the disulfide linkages in the hinge region to produce F(ab)'2, a dimer of Fab' which itself is a light chain (VL-CL) joined to VH-CH1 by a disulfide bond. The F(ab)'2 can be reduced under mild conditions to break the disulfide linkage in the hinge region, thereby converting the F(ab)'2 dimer into an Fab' monomer. The Fab' monomer is a Fab with part of the hinge region. (Paul, W. E., "Fundamental Immunology," 3d Ed., New York: Raven Press, 1993). While various antibody fragments are defined in terms of the digestion of an intact antibody, one of skill will appreciate that such fragments can be synthesized de novo either chemically or by using recombinant DNA methodology. Thus, the term "antibody," as used herein, also includes antibody fragments either produced by the modification of whole antibodies, or those synthesized de novo using recombinant DNA methodologies (for example, single chain Fv) or those identified using phage display libraries (see, for example, McCafferty, J. et al., "Phage antibodies: filamentous phage displaying antibody variable domains," Nature, Vol. 348, No. 66301, pp. 552-554, 1990).

Antibodies further include one or more immunoglobulin chains that are chemically conjugated to, or expressed as, fusion proteins with other proteins. It also includes bispecific antibodies. A bispecific or bifunctional antibody is an artificial hybrid antibody having two different heavy/light chain pairs and two different binding sites.

Other antigen-binding fragments or antibody portions of the invention include, bispecific scFv antibodies where the antibody molecule recognizes two different epitopes, single binding domains (sdAb or nanobodies), and minibodies.

The term "antibody fragment" includes, but is not limited to one or more antigen binding fragments of antibodies alone or in combination with other molecules, including, but not limited to Fab', F(ab')2, Fab, Fv, rIgG (reduced IgG), scFv fragments, single domain fragments (nanobodies), peptibodies, minibodies. The term "scFv" refers to a single chain Fv ("fragment variable") antibody in which the variable domains of the heavy chain and of the light chain of a traditional two chain antibody have been joined to form one chain.

A pharmaceutically acceptable carrier can be a pharmaceutically acceptable material, composition, or vehicle that is involved in carrying or transporting a compound of interest from one tissue, organ, or portion of the body to another tissue, organ, or portion of the body. For example, the carrier can be a liquid or solid filler, diluent, excipient, solvent, or encapsulating material, or some combination thereof. Each component of the carrier is "pharmaceutically acceptable" in that it is be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits. The pharmaceutical compositions described herein may be administered by any suitable route of administration. A route of administration can refer to any administration pathway known in the art, including but not limited to aerosol, enteral, nasal, ophthalmic, oral, parenteral, rectal, transdermal (for example, topical cream or ointment, patch), or vaginal. "Transdermal" administration can be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the antigen binding construct can be delivered intraoperatively as a local administration during an intervention or resection.

The term "nucleic acid" or "polynucleotide" refers to deoxyribonucleic acids (DNA) or ribonucleic acids (RNA) and polymers thereof in either single- or doublestranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (for example, degenerate codon substitutions), alleles, orthologs, SNPs, and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer, M. A. et al., "Enhanced evolutionary PCR using oligonucleotides with inosine at the 3'-terminus," Nucleic Acid Res., Vol. 19, No. 18, pp. 5081, 1991; Ohtsuka, E. et al., "An alternative approach to deoxyoligonucleotides as hybridization probes by insertion of deoxyinosine at ambiguous codon positions," J. Biol. Chem., Vol. 260, No. 5, pp. 2605-2608, 1985; Rossolini, G. M. et al., "Use of deoxyinosine containing primers vs degenerate primers for polymerase chain reaction based on ambiguous sequence information," Mol. Cell. Probes, Vol. 8, No. 2, pp. 91-98, 1994).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine. Amino acid analogs refer to compounds that have the same basic chemical structure as a naturally occurring amino acid, for example, an alpha-carbon that is bound to a hydrogen, a carboxyl group, an amino group, and an R group, for example, homoserine, norleucine, methionine sulfoxide, methionine methyl sulfonium. Such analogs have modified R groups (for example, norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, for example, Creighton, T. E., "Proteins—Structures and Molecular Properties," W. H. Freeman & Co. Ltd., 1984).

The term "percentage of sequence identity" can be determined by comparing two optimally aligned sequences over a comparison window, wherein the portion of the polynucleotide sequence in the comparison window can comprise additions or deletions (i.e., gaps) as compared to the reference sequence (for example, a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (for example, 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. Optionally, the identity exists over a region that is at least about 15, 25 or 50 nucleotides in length, or more preferably over a region that is 100 to 500 or 1000 or more nucleotides in length, or over the full length of the reference sequence.

With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, for example, amino acid sequences of 20 or fewer amino acids, in some embodiments, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (1970) Adv. Appl. Math. 2:482c, by the homology alignment algorithm of Needleman, S. B. et al., "A general method applicable to the search for similarities in the amino acid sequence of two proteins," J. Mol. Biol., Vol. 48, No. 3, pp. 443-453, 1970, by the search for similarity method of Pearson, W. R. et al., "Improved tools for biological sequence comparison," Proc. Natl. Acad. Sci. U.S.A., Vol. 85, No. 8, pp. 2444-2448, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, for example, Ausubel, F. M. et al., Current Protocols in Molecular Biology, Supplement, 1995).

Two examples of algorithms that are suitable for determining percent sequence identity and sequence similarity are the BLAST and BLAST 2.0 algorithms, which are described in Altschul, S. F. et al., "Gapped BLAST and PSI-BLAST: a new generation of protein database search programs," Nucleic Acids Res., Vol. 25, No. 17, pp. 3389-3402, 1977, and Altschul, S. F. et al., "Basic local alignment search tool," J. Mol. Biol., Vol. 215, No. 3, pp. 403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, S. F. et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see, Henikoff, S. et al., "Amino acid substitution matrices from protein blocks," Proc. Natl. Acad. Sci. U.S.A., Vol. 89, No. 22, pp. 10915-10919, 1992) alignments (B) of 50, expectation (E) of 10, M=5, N=−4, and a comparison of both strands.

The BLAST algorithm also performs a statistical analysis of the similarity between two sequences (see, for example, Karlin, S. et al., "Applications and statistics for multiple high-scoring segments in molecular sequences," Proc. Natl. Acad. Sci. U.S.A., Vol. 90, No. 12, pp. 5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, in some embodiments, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "subject," "patient," and "individual" interchangeably refer to an entity that is being examined and/or treated. This can include, for example, a mammal, for example, a human or a non-human primate mammal. The mammal can also be a laboratory mammal, for example, mouse, rat, rabbit, hamster. In some embodiments, the mammal can be an agricultural mammal (for example, equine, ovine, bovine, porcine, camelid) or domestic mammal (for example, canine, feline).

The term "co-administer" refers to the administration of two active agents in the blood of an individual or in a sample to be tested. Active agents that are coadministered can be concurrently or sequentially delivered.

Diabodies with Extension Sequences

Provided herein are diabodies that can include an extension sequence. In some embodiments, the diabody comprises a heavy chain variable domain a light chain variable domain, a linker, and an extension sequence. In some embodiments, the extension sequence can comprise or consist of at least one of the following:

(a) EPKSX$_{n5}$DKTHTCX$_{n1}$X$_{n2}$CX$_{n3}$X$_{n4}$C, (SEQ ID NO: 1)

(b) ERKX$_{n5}$CX$_{n1}$X$_{n2}$CX$_{n3}$X$_{n4}$C, (SEQ ID NO: 2)

(c) ELKTPLGDTTHTCX$_{n1}$X$_{n2}$CX$_{n3}$X$_{n4}$C, (SEQ ID NO: 3)

(d) ESKYGPPCX$_{n1}$X$_{n2}$CX$_{n3}$X$_{n4}$C, (SEQ ID NO: 4)

(e) CPPCPPC, (SEQ ID NO: 5)

(f) CPPCPPCPPC, (SEQ ID NO: 6)

or (g) GGC(PPC)$_n$, (SEQ ID NO: 11)

wherein n is 1, 2, 3, 4, 5, 6, 7, 8, or 9.

$X_{n1}$ can be any amino acid. $X_{n2}$ can be any amino acid. $X_{n3}$ can be any amino acid. $X_{n4}$ can be any amino acid. $X_{n5}$ can be any amino acid. Each of these arrangements will form one half of the diabody. The linker connects a heavy chain variable domain to a light chain variable domain through its peptide backbone, while the extension sequence can connect $V_H$ to $V_H$ or $V_L$ to $V_L$ through a disulfide bond. Some embodiments of these extension sequences are shown in Table 0.1 below:

TABLE 0.1

| SEQUENCE LISTING | |
|---|---|
| NUMBER | SEQUENCE |
| SEQ ID NO: 1 | EPKSX$_{n5}$DKTHTCX$_{n1}$X$_{n2}$CX$_{n3}$X$_{n4}$C |
| SEQ ID NO: 2 | ERKX$_{n5}$CX$_{n1}$X$_{n2}$CX$_{n3}$X$_{n4}$C |
| SEQ ID NO: 3 | ELKTPLGDTTHTCX$_{n1}$X$_{n2}$CX$_{n3}$X$_{n4}$C |
| SEQ ID NO: 4 | ESKYGPPCX$_{n1}$X$_{n2}$CX$_{n3}$X$_{n4}$C |
| SEQ ID NO: 5 | CPPCPPC |
| SEQ ID NO: 6 | CPPCPPCPPC |
| SEQ ID NO: 7 | CPPC |
| SEQ ID NO: 8 | CPPCPPCPPCPPC |
| SEQ ID NO: 9 | CPPCPPCPPCPPCPPC |
| SEQ ID NO: 10 | CPPCPPCPPCPPCPPCPPC |
| SEQ ID NO: 11 | GGC(PPC)$_n$ |
| SEQ ID NO: 12 | CX$_{n1}$X$_{n2}$CX$_{n3}$X$_{n4}$CX$_{n5}$X$_{n6}$C |
| SEQ ID NO: 13 | CX$_{n1}$X$_{n2}$CX$_{n3}$X$_{n4}$CX$_{n5}$X$_{n6}$CX$_{n7}$X$_{n8}$C |
| SEQ ID NO: 14 | CX$_{n1}$X$_{n2}$CX$_{n3}$X$_{n4}$CX$_{n5}$X$_{n6}$CX$_{n7}$X$_{n8}$CX$_{n9}$X$_{n10}$C |
| SEQ ID NO: 15 | CX$_{n1}$X$_{n2}$CX$_{n3}$X$_{n4}$CX$_{n5}$X$_{n6}$CX$_{n7}$X$_{n8}$CX$_{n9}$X$_{n10}$C X$_{n11}$X$_{n12}$C |

TABLE 0.1 -continued

| SEQUENCE LISTING | |
|---|---|
| NUMBER | SEQUENCE |
| SEQ ID NO: 16 | CX$_{n1}$X$_{n2}$CX$_{n3}$X$_{n4}$C |
| SEQ ID NO: 17 | GGC(X$_{n1}$X$_{n2}$C)$_n$ |

In some embodiments, the diabody comprises a first heavy chain variable domain, a first light chain variable domain, a first linker that connects the first heavy chain variable domain and the first light chain variable domains, a second heavy chain variable domain, a second light chain variable domain, a second linker that connects the second heavy and second light chain variable domains, and two extension sequences that covalently connect either a) the first heavy chain variable domain to the second heavy chain variable or b) the first light chain variable domain to the second light chain variable domain. The linker connects a heavy chain variable domain to a light chain variable domain through its peptide backbone. The connection between the two extension sequences can be achieved through crosslinking one or more of the cysteines within the extension sequences. As noted above, the extension sequence can be selected from the group consisting of: a) EPKSX$_{n5}$DKTHTCX$_{n1}$X$_{n2}$CX$_{n3}$X$_{n4}$C (SEQ ID NO: 1), b) ERKX$_{n5}$CX$_{n1}$X$_{n2}$CX$_{n3}$X$_{n4}$C (SEQ ID NO: 2), c) ELKTPLGDTTHTCX$_{n1}$X$_{n2}$CX$_{n3}$X$_{n4}$C (SEQ ID NO: 3), d) ESKYGPPCX$_{n1}$X$_{n2}$CX$_{n3}$X$_{n4}$C (SEQ ID NO: 4), e) CPPCPPC (SEQ ID NO: 5), and f) CPPCPPCPPC (SEQ ID NO: 6) and g) GGC(PPC)$_n$ (SEQ ID NO: 11), wherein n is 1, 2, 3, 4, 5, 6, 7, 8, or 9. $X_{n1}$, $X_{n2}$, $X_{n3}$, $X_{n4}$, and $X_{n5}$ can be any amino acid. Additional options for extension sequences are disclosed herein and can be combined with any one or more of the diabody arrangements provided herein.

In some embodiments, the diabody comprises a first chain and a second chain. The first chain comprises a first heavy chain variable domain, a first light chain variable domain, a first linker that connects the first heavy chain variable domain and the first light chain variable domain, and a first extension sequence. In some embodiments, the first chain comprises a single, continuous, peptide backbone. The diabody further comprises the second chain that comprises a second heavy chain variable domain, a second light chain variable domain, a second linker that connects the second heavy and second light chain variable domains, and a second extension sequence. In some embodiments, the second chain comprises a single, continuous, peptide backbone. The first extension sequence and the second extension sequence are covalently connected or bonded to one another. This connection can be through one or more of the cysteines in the first extension sequence forming one or more disulfide bonds with the cysteines in the second extension sequence. The linker connects a heavy chain variable domain to a light chain variable domain through its peptide backbone, while the extension sequence can connect $V_H$ to $V_H$ or $V_L$ to $V_L$ through a disulfide bond. The first extension sequence and the second extension sequence are selected from the group consisting of at least one of: EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPCPPC (SEQ ID NO: 5), and GGC(PPC)$_n$ (SEQ ID NO: 11), wherein n is 1, 2, 3, 4, 5, 6, 7, 8, or 9, wherein $X_{n1}$, $X_{n2}$, $X_{n3}$, $X_{n4}$, and $X_{n5}$ can be any amino acid.

In some embodiments, the diabody is monospecific. In some embodiments, the diabody is bispecific. A bispecific diabody can be comprised of two different heavy/light chain pairs and/or it can recognize two different epitopes. Examples of targets to which the diabodies can bind include, but are not limited to, one or more of PCSA, PSMA, CD8, HER2, CD3, 5T4, PD-L1, folate receptor alpha, Mesothelin, CA19-9, CD19, CD20, and Her2/neu. In some embodiments, the first heavy chain variable domain and the second light chain variable domain are associated so as to form a first binding domain. In some embodiments, the second heavy chain variable domain and the first light chain variable domain are associated so as to form a second binding domain (e.g., as shown in FIG. 1). In some embodiments, the first light chain variable domain and the second heavy chain variable domain are associated so as to form a first binding domain.

In addition to the extension sequences noted above, other variations and subsets of extension sequences are contemplated as well. In some embodiments, amino acid sequences of extension sequences within diabodies are provided. Any of the diabodies described herein can comprise any of the extension sequences described herein.

In some embodiments, the extension sequence is EPKSX$_{n5}$DKTHTCX$_{n1}$X$_{n2}$CX$_{n3}$X$_{n4}$C (SEQ ID NO: 1). X$_{n1}$ can be any amino acid. X$_{n2}$ can be any amino acid. X$_{n3}$ can be any amino acid. X$_{n4}$ can be any amino acid. X$_{n5}$ can be any amino acid. In some embodiments, any of X$_{n1}$, X$_{n2}$, X$_{n3}$, X$_{n4}$, and X$_{n5}$ are P (SEQ ID NO: 18). In some embodiments, at least one of X$_{n1}$, X$_{n2}$, X$_{n3}$, X$_{n4}$, and X$_{n5}$ is P (SEQ ID NO: 19). In some embodiments, X$_{n1}$ is P (SEQ ID NO: 20). In some embodiments X$_{n2}$ is P (SEQ ID NO: 21). In some embodiments, X$_{n3}$ is P (SEQ ID NO: 22). In some embodiments, X$_{n4}$ is P (SEQ ID NO: 23). In some embodiments, X$_{n5}$ is P (SEQ ID NO: 24). The remaining positions can be any amino acid (SEQ ID NO: 18-SEQ ID NO: 24).

In some embodiments, at least any two of X$_{n1}$, X$_{n2}$, X$_{n3}$, X$_{n4}$, and X$_{n5}$ are P (SEQ ID NO: 25) in EPKSX$_{n5}$DKTHTCX$_{n1}$X$_{n2}$CX$_{n3}$X$_{n4}$C (SEQ ID NO: 1). In some embodiments the X$_{n1}$ and X$_{n2}$ are P (SEQ ID NO: 26). In some embodiments, X$_{n1}$ and X$_{n3}$ are P (SEQ ID NO: 27). In some embodiments, X$_{n1}$ and X$_{n4}$ are P (SEQ ID NO: 28). In some embodiments, X$_{n1}$ and X$_{n5}$ are P (SEQ ID NO: 29). In some embodiments, X$_{n2}$ and X$_{n3}$ are P (SEQ ID NO: 30). In some embodiments, X$_{n2}$ and X$_{n4}$ are P (SEQ ID NO: 31). In some embodiments, X$_{n2}$ and X$_{n5}$ are P (SEQ ID NO: 32). In some embodiments, X$_{n3}$ and X$_{n4}$ are P (SEQ ID NO: 33). In some embodiments, X$_{n3}$ and X$_{n5}$ are P (SEQ ID NO: 34). In some embodiments, X$_{n4}$ and X$_{n5}$ are P (SEQ ID NO: 35). The remaining positions can be any amino acid (SEQ ID NO: 25-SEQ ID NO: 35).

In some embodiments, at least any three of X$_{n1}$, X$_{n2}$, X$_{n3}$, X$_{n4}$, and X$_{n5}$ are P (SEQ ID NO: 36) in EPKSX$_{n5}$DKTHTCX$_{n1}$X$_{n2}$CX$_{n3}$X$_{n4}$C (SEQ ID NO: 1). In some embodiments, X$_{n1}$, X$_{n2}$, X$_{n3}$ are P (SEQ ID NO: 37). In some embodiments, X$_{n2}$, X$_{n3}$ and X$_{n4}$ are P (SEQ ID NO: 38). In some embodiments, X$_{n3}$, X$_{n4}$, and X$_{n5}$ are P (SEQ ID NO: 39). In some embodiments, X$_{n1}$, X$_{n2}$, and X$_{n4}$ are P (SEQ ID NO: 40). In some embodiments, X$_{n1}$, X$_{n2}$, and X$_{n5}$ are P (SEQ ID NO: 41). In some embodiments, X$_{n1}$, X$_{n3}$, and X$_{n4}$ are P (SEQ ID NO: 42). In some embodiments, X$_{n1}$, X$_{n4}$, and X$_{n5}$ are P (SEQ ID NO: 43). In some embodiments, X$_{n2}$, X$_{n3}$, and X$_{n5}$ are P (SEQ ID NO: 44). In some embodiments, X$_{n2}$, X$_{n4}$, and X$_{n5}$ are P (SEQ ID NO: 45). In some embodiments, X$_{n1}$, X$_{n3}$, and X$_{n5}$ are P (SEQ ID NO: 46). The remaining positions can be any amino acid (SEQ ID NO: 36-SEQ ID NO: 46).

In some embodiments, at least any four of X$_{n1}$, X$_{n2}$, X$_{n3}$, X$_{n4}$, and X$_{n5}$ are P (SEQ ID NO: 47) in EPKSX$_{n5}$DKTHTCX$_{n1}$X$_{n2}$CX$_{n3}$X$_{n4}$C (SEQ ID NO: 1). In some embodiments, X$_{n1}$, X$_{n2}$, X$_{n3}$, and X$_{n4}$ are P (SEQ ID NO: 48). In some embodiments, X$_{n2}$, X$_{n3}$, X$_{n4}$, and X$_{n5}$ are P (SEQ ID NO: 49). In some embodiments, X$_{n1}$, X$_{n3}$, X$_{n4}$, and X$_{n5}$ are P (SEQ ID NO: 50). In some embodiments, X$_{n1}$, X$_{n2}$, X$_{n4}$, and X$_{n5}$ are P (SEQ ID NO: 51). The remaining positions can be any amino acid (SEQ ID NO: 47-SEQ ID NO: 51).

In some embodiments all of X$_{n1}$, X$_{n2}$, X$_{n3}$, X$_{n4}$, and X$_{n5}$ are P (SEQ ID NO: 52) in EPKSX$_{n5}$DKTHTCX$_{n1}$X$_{n2}$CX$_{n3}$X$_{n4}$C (SEQ ID NO: 1).

In some embodiments, the extension sequence comprises greater than 70% sequence identity to the EPKSX$_{n5}$DKTHTCX$_{n1}$X$_{n2}$CX$_{n3}$X$_{n4}$C (SEQ ID NO: 1) sequence, for example, 75%, 85%, or 95%.

In some embodiments, a nucleic acid sequence is provided that encodes for EPKSX$_{n5}$DKTHTCX$_{n1}$X$_{n2}$CX$_{n3}$X$_{n4}$C (SEQ ID NO: 1). The nucleic acid sequence can comprise conservative substitutions of EPKSX$_{n5}$DKTHTCX$_{n1}$X$_{n2}$CX$_{n3}$X$_{n4}$C (SEQ ID NO: 1), which results in expression of a conservatively modified variant of the sequence.

In some embodiments the extension sequence is ERKX$_{n5}$CX$_{n1}$X$_{n2}$CX$_{n3}$X$_{n4}$C (SEQ ID NO: 2) X$_{n1}$ can be any amino acid. X$_{n2}$ can be any amino acid. X$_{n3}$ can be any amino acid. X$_{n4}$ can be any amino acid. X$_{n5}$ can be any amino acid. In some embodiments, any of X$_{n1}$, X$_{n2}$, X$_{n3}$, X$_{n4}$, and X$_{n5}$ are P (SEQ ID NO: 53). In some embodiments, at least one of X$_{n1}$, X$_{n2}$, X$_{n3}$, X$_{n4}$, and X$_{n5}$ is P (SEQ ID NO: 54). In some embodiments, X$_{n1}$ is P (SEQ ID NO: 55). In some embodiments X$_{n2}$ is P (SEQ ID NO: 56). In some embodiments, X$_{n3}$ is P (SEQ ID NO: 57). In some embodiments, X$_{n4}$ is P (SEQ ID NO: 58). In some embodiments, X$_{n5}$ is P. The remaining positions can be any amino acid (SEQ ID NO: 53-SEQ ID NO: 58).

In some embodiments, at least any two of X$_{n1}$, X$_{n2}$, X$_{n3}$, X$_{n4}$, and X$_{n5}$ are P (SEQ ID NO: 59) in ERKX$_{n5}$CX$_{n1}$X$_{n2}$CX$_{n3}$X$_{n4}$C (SEQ ID NO: 2). In some embodiments the X$_{n1}$ and X$_{n2}$ are P (SEQ ID NO: 60). In some embodiments, X$_{n1}$ and X$_{n3}$ are P (SEQ ID NO: 61). In some embodiments, X$_{n1}$ and X$_{n4}$ are P (SEQ ID NO: 62). In some embodiments, X$_{n1}$ and X$_{n5}$ are P (SEQ ID NO: 63). In some embodiments, X$_{n2}$ and X$_{n3}$ are P (SEQ ID NO: 64). In some embodiments, X$_{n2}$ and X$_{n4}$ are P (SEQ ID NO: 65). In some embodiments, X$_{n2}$ and X$_{n5}$ are P (SEQ ID NO: 66). In some embodiments, X$_{n3}$ and X$_{n4}$ are P (SEQ ID NO: 67). In some embodiments, X$_{n3}$ and X$_{n5}$ are P (SEQ ID NO: 68). In some embodiments, X$_{n4}$ and X$_{n5}$ are P (SEQ ID NO: 69). The remaining positions can be any amino acid (SEQ ID NO: 59-SEQ ID NO: 69).

In some embodiments, at least any three of X$_{n1}$, X$_{n2}$, X$_{n3}$, X$_{n4}$, and X$_{n5}$ are P (SEQ ID NO: 70) in ERKX$_{n5}$CX$_{n1}$X$_{n2}$CX$_{n3}$X$_{n4}$C (SEQ ID NO: 2). In some embodiments, X$_{n1}$, X$_{n2}$, X$_{n3}$ are P (SEQ ID NO: 71). In some embodiments, X$_{n2}$, X$_{n3}$ and X$_{n4}$ are P (SEQ ID NO: 72). In some embodiments, X$_{n3}$, X$_{n4}$, and X$_{n5}$ are P (SEQ ID NO: 73). In some embodiments, X$_{n1}$, X$_{n2}$, and X$_{n4}$ are P (SEQ ID NO: 74). In some embodiments, X$_{n1}$, X$_{n2}$, and X$_{n5}$ are P (SEQ ID NO: 75). In some embodiments, X$_{n1}$, X$_{n3}$, and X$_{n4}$ are P (SEQ ID NO: 76). In some embodiments, X$_{n1}$, X$_{n4}$, and X$_{n5}$ are P (SEQ ID NO: 77). In some embodiments, X$_{n2}$, X$_{n3}$, and X$_{n5}$ are P (SEQ ID NO: 78). In some embodiments, X$_{n2}$, X$_{n4}$, and X$_{n5}$ are P (SEQ ID NO: 79). In some embodiments, $X_{n1}$, $X_{n3}$, and $X_{n5}$ are P (SEQ ID NO: 80). The remaining positions can be any amino acid (SEQ ID NO: 70-SEQ ID NO: 80).

In some embodiments, at least any four of $X_{n1}$, $X_{n2}$, $X_{n3}$, $X_{n4}$, and $X_{n5}$ are P (SEQ ID NO: 81) in ERK$X_{n5}$C$X_{n1}X_{n2}$C$X_{n3}X_{n4}$C (SEQ ID NO: 2). In some embodiments, $X_{n1}$, $X_{n2}$, $X_{n3}$, and $X_{n4}$ are P (SEQ ID NO: 82). In some embodiments, $X_{n2}$, $X_{n3}$, $X_{n4}$, and $X_{n5}$ are P (SEQ ID NO: 83). In some embodiments, $X_{n1}$, $X_{n3}$, $X_{n4}$, and $X_{n5}$ are P (SEQ ID NO: 84). In some embodiments, $X_{n1}$, $X_{n2}$, $X_{n4}$, and $X_{n5}$ are P (SEQ ID NO: 85). The remaining positions can be any amino acid (SEQ ID NO: 81-SEQ ID NO: 85).

In some embodiments all of $X_{n1}$, $X_{n2}$, $X_{n3}$, $X_{n4}$, and $X_{n5}$ is P (SEQ ID NO: 86).

In some embodiments, the extension sequence comprises greater than 70% sequence identity to the ERK$X_{n5}$C$X_{n1}X_{n2}$C$X_{n3}X_{n4}$C (SEQ ID NO: 2) sequence, for example, 75%, 85%, or 95%. In some embodiments, a nucleic acid sequence is provided that encodes for ERK$X_{n5}$C$X_{n1}X_{n2}$C$X_{n3}X_{n4}$C (SEQ ID NO: 2). The nucleic acid sequence can comprise conservative substitutions of ERK$X_{n5}$C$X_{n1}X_{n2}$C$X_{n3}X_{n4}$C (SEQ ID NO: 2), which results in expression of conservatively modified variant of the sequence.

In some embodiments the extension sequence is ELKTPLGDTTHTC$X_{n1}X_{n2}$C$X_{n3}X_{n4}$C (SEQ ID NO: 3). $X_{n1}$ can be any amino acid. $X_{n2}$ can be any amino acid. $X_{n3}$ can be any amino acid. $X_{n4}$ can be any amino acid.

In some embodiments, any of $X_{n1}$, $X_{n2}$, $X_{n3}$, and $X_{n4}$ are P (SEQ ID NO: 87) in ELKTPLGDTTHTC$X_{n1}X_{n2}$C$X_{n3}X_{n4}$C (SEQ ID NO: 3).

In some embodiments, at least one of $X_{n1}$, $X_{n2}$, $X_{n3}$, and $X_{n4}$ is P (SEQ ID NO: 88) in ELKTPLGDTTHTC$X_{n1}X_{n2}$C$X_{n3}X_{n4}$C (SEQ ID NO: 3). In some embodiments, $X_{n1}$ is P (SEQ ID NO: 89). In some embodiments, $X_{n2}$ is P (SEQ ID NO: 90). In some embodiments, $X_{n3}$ is P (SEQ ID NO: 91). In some embodiments, $X_{n4}$ is P (SEQ ID NO: 92). The remaining positions can be any amino acid (SEQ ID NO: 87-SEQ ID NO: 92).

In some embodiments, at least any two of $X_{n1}$, $X_{n2}$, $X_{n3}$, and $X_{n4}$ are P (SEQ ID NO: 93) in ELKTPLGDTTHTC$X_{n1}X_{n2}$C$X_{n3}X_{n4}$C (SEQ ID NO: 3). In some embodiments, $X_{n1}$ and $X_{n2}$ are P (SEQ ID NO: 94). In some embodiments $X_{n1}$ and $X_{n3}$ are P (SEQ ID NO: 95). In some embodiments, $X_{n1}$ and $X_{n4}$ are P (SEQ ID NO: 96). In some embodiments, $X_{n2}$ and $X_{n3}$ are P (SEQ ID NO: 97). In some embodiments, $X_{n2}$ and $X_{n4}$ are P (SEQ ID NO: 98). In some embodiments $X_{n3}$ and $X_{n4}$ are P (SEQ ID NO: 99). The remaining positions can be any amino acid (SEQ ID NO: 93-SEQ ID NO: 99).

In some embodiments, at least any three of $X_{n1}$, $X_{n2}$, $X_{n3}$, and $X_{n4}$ are P (SEQ ID NO: 100) in ELKTPLGDTTHTC$X_{n1}X_{n2}$C$X_{n3}X_{n4}$C (SEQ ID NO: 3). In some embodiments, $X_{n1}$, $X_{n2}$, and $X_{n3}$ are P (SEQ ID NO: 101). In some embodiments, $X_{n1}$, $X_{n2}$, and $X_{n4}$ are P (SEQ ID NO: 102). In some embodiments, $X_{n1}$, $X_{n3}$, and $X_{n4}$ are P (SEQ ID NO: 103). In some embodiments, $X_{n2}$, $X_{n3}$, and $X_{n4}$ are P (SEQ ID NO: 104).

In some embodiments all of $X_{n1}$, $X_{n2}$, $X_{n3}$, and $X_{n4}$ are P (SEQ ID NO: 105). The remaining positions can be any amino acid (SEQ ID NO: 100-SEQ ID NO: 104).

In some embodiments, the extension sequence comprises greater than 70% sequence identity to the ELKTPLGDTTHTC$X_{n1}X_{n2}$C$X_{n3}X_{n4}$C (SEQ ID NO: 3) sequence, for example, 75%, 85%, or 95%. In some embodiments, a nucleic acid sequence is provided that encodes for ELKTPLGDTTHTC$X_{n1}X_{n2}$C$X_{n3}X_{n4}$C (SEQ ID NO: 3). The nucleic acid sequence can comprise conservative substitutions of ELKTPLGDTTHTC$X_{n1}X_{n2}$C$X_{n3}X_{n4}$C (SEQ ID NO: 3), which results in expression of a conservatively modified variant of the sequence.

In some embodiments the extension sequence is ESKYGPPC$X_{n1}X_{n2}$C$X_{n3}X_{n4}$C (SEQ ID NO: 4). $X_{n1}$ can be any amino acid. $X_{n2}$ can be any amino acid. $X_{n3}$ can be any amino acid. $X_{n4}$ can be any amino acid.

In some embodiments, any of $X_{n1}$, $X_{n2}$, $X_{n3}$, and $X_{n4}$ are P (SEQ ID NO: 106) in ESKYGPPC$X_{n1}X_{n2}$C$X_{n3}X_{n4}$C (SEQ ID NO: 4).

In some embodiments, at least one of $X_{n1}$, $X_{n2}$, $X_{n3}$, and $X_{n4}$ is P (SEQ ID NO: 107). In some embodiments, $X_{n1}$ is P (SEQ ID NO: 108) in ESKYGPPC$X_{n1}X_{n2}$C$X_{n3}X_{n4}$C (SEQ ID NO: 4). In some embodiments, $X_{n2}$ is P (SEQ ID NO: 109). In some embodiments, $X_{n3}$ is P (SEQ ID NO: 110). In some embodiments, $X_{n4}$ is P (SEQ ID NO: 111). The remaining positions can be any amino acid (SEQ ID NO: 106-SEQ ID NO: 111).

In some embodiments, at least any two of $X_{n1}$, $X_{n2}$, $X_{n3}$, and $X_{n4}$ are P (SEQ ID NO: 112) in ESKYGPPC$X_{n1}X_{n2}$C$X_{n3}X_{n4}$C (SEQ ID NO: 4). In some embodiments, $X_{n1}$ and $X_{n2}$ are P (SEQ ID NO: 113). In some embodiments $X_{n1}$ and $X_{n3}$ are P (SEQ ID NO: 114). In some embodiments, $X_{n1}$ and $X_{n4}$ are P (SEQ ID NO: 115). In some embodiments, $X_{n2}$ and $X_{n3}$ are P (SEQ ID NO: 116). In some embodiments, $X_{n2}$ and $X_{n4}$ are P (SEQ ID NO: 117). In some embodiments $X_{n3}$ and $X_{n4}$ are P (SEQ ID NO: 118).

In some embodiments, at least any three of $X_{n1}$, $X_{n2}$, $X_{n3}$, and $X_{n4}$ are P (SEQ ID NO: 119) in ESKYGPPC$X_{n1}X_{n2}$C$X_{n3}X_{n4}$C (SEQ ID NO: 4). In some embodiments, $X_{n1}$, $X_{n2}$, and $X_{n3}$ are P (SEQ ID NO: 120). In some embodiments, $X_{n1}$, $X_{n2}$, and $X_{n4}$ are P (SEQ ID NO: 121). In some embodiments, $X_{n1}$, $X_{n3}$, and $X_{n4}$ are P (SEQ ID NO: 122). In some embodiments, $X_{n2}$, $X_{n3}$, and $X_{n4}$ are P (SEQ ID NO: 123).

In some embodiments all of $X_{n1}$, $X_{n2}$, $X_{n3}$, and $X_{n4}$ are P (SEQ ID NO: 124) in ESKYGPPC$X_{n1}X_{n2}$C$X_{n3}X_{n4}$C (SEQ ID NO: 4). The remaining positions can be any amino acid (SEQ ID NO: 112-SEQ ID NO: 123).

In some embodiments, the extension sequence comprises greater than 70% sequence identity to the ESKYGPPC$X_{n1}X_{n2}$C$X_{n3}X_{n4}$C (SEQ ID NO: 4) sequence, for example, 75%, 85%, or 95%. In some embodiments, a nucleic acid sequence is provided that encodes for ESKYGPPC$X_{n1}X_{n2}$C$X_{n3}X_{n4}$C (SEQ ID NO: 4). The nucleic acid sequence can comprise conservative substitutions of ESKYGPPC$X_{n1}X_{n2}$C$X_{n3}X_{n4}$C (SEQ ID NO: 4), which results in expression of a conservatively modified variant of the sequence.

In some embodiments the extension sequence comprises the motif, $X_{n1}X_{n2}$C. In some embodiments, this motif repeats 1, 2, 3, 4, 5, or 6 times. This can also be expressed as C$X_{n1}X_{n2}$ in a repeating motif. $X_{n1}X_{n2}$ can be any amino acid, but are preferably one or more proline.

In some embodiments, there is no C-terminus cysteine. In some embodiments, there is no N-terminus cysteine. In some embodiments, both terminal cysteines are removed.

In some embodiments, the extension sequence is C$X_{n1}X_{n2}$C$X_{n3}X_{n4}$C (SEQ ID NO: 16). $X_{n1}$ can be any amino acid. $X_{n2}$ can be any amino acid. $X_{n3}$ can be any amino acid. $X_{n4}$ can be any amino acid. In some embodiments, any one of $X_{n1}$, $X_{n2}$, $X_{n3}$, $X_{n4}$ are P (SEQ ID NO: 125). In some embodiments, any two of $X_{n1}$, $X_{n2}$, $X_{n3}$, $X_{n4}$ are P (SEQ ID NO: 126). In some embodiments, any three of $X_{n1}$, $X_{n2}$, $X_{n3}$, $X_{n4}$ are P (SEQ ID NO: 127). In some embodiments, the extension sequence is CPPCPPC (SEQ ID NO; 5). In some embodiments the C-terminus cysteine is removed. In some embodiments, the N-terminus cysteine is removed. In some embodiments, both terminal cysteines are removed.

In some embodiments, the extension sequence is $CX_{n1}X_{n2}CX_{n3}X_{n4}CX_{n5}X_{n6}C$ (SEQ ID NO: 12). $X_{n1}$ can be any amino acid. $X_{n2}$ can be any amino acid. $X_{n3}$ can be any amino acid. $X_{n4}$ can be any amino acid. $X_{n5}$ can be any amino acid. $X_{n6}$ can be any amino acid. In some embodiments, any one of $X_{n1}$, $X_{n2}$, $X_{n3}$, $X_{n4}$, $X_{n5}$, $X_{n6}$ are P (SEQ ID NO: 128). In some embodiments, any two of $X_{n1}$, $X_{n2}$, $X_{n3}$, $X_{n4}$, $X_{n5}$, $X_{n6}$ are P (SEQ ID NO: 129). In some embodiments, any three of $X_{n1}$, $X_{n2}$, $X_{n3}$, $X_{n4}$, $X_{n5}$, $X_{n6}$ are P (SEQ ID NO: 130). In some embodiments, any four of $X_{n1}$, $X_{n2}$, $X_{n3}$, $X_{n4}$, $X_{n5}$, $X_{n6}$ are P (SEQ ID NO: 131). In some embodiments, any five of $X_{n1}$, $X_{n2}$, $X_{n3}$, $X_{n4}$, $X_{n5}$, $X_{n6}$ are P (SEQ ID NO: 132). In some embodiments, the extension sequence is CPPCPPCPPC (SEQ ID NO: 6). In some embodiments, the C-terminus cysteine is removed. In some embodiments, the N-terminus cysteine is removed. In some embodiments, both terminal cysteines are removed.

In some embodiments the extension sequence is $CX_{n1}X_{n2}CX_{n3}X_{n4}CX_{n5}X_{n6}CX_{n7}X_{n8}C$ (SEQ ID NO: 13). $X_{n1}$ can be any amino acid. $X_{n2}$ can be any amino acid. $X_{n3}$ can be any amino acid. $X_{n4}$ can be any amino acid. $X_{n5}$ can be any amino acid. $X_{n6}$ can be any amino acid. $X_{n7}$ can be any amino acid. $X_{n8}$ can be any amino acid. In some embodiments, any one of $X_{n1}$, $X_{n2}$, $X_{n3}$, $X_{n4}$, $X_{n5}$, $X_{n6}$, $X_{n7}$, $X_{n8}$ are P (SEQ ID NO: 133). In some embodiments, any two of $X_{n1}$, $X_{n2}$, $X_{n3}$, $X_{n4}$, $X_{n5}$, $X_{n6}$, $X_{n7}$, $X_{n8}$ are P (SEQ ID NO: 134). In some embodiments, any three of $X_{n1}$, $X_{n2}$, $X_{n3}$, $X_{n4}$, $X_{n5}$, $X_{n6}$, $X_{n7}$, $X_{n8}$ are P (SEQ ID NO: 135). In some embodiments, any four of $X_{n1}$, $X_{n2}$, $X_{n3}$, $X_{n4}$, $X_{n5}$, $X_{n6}$, $X_{n7}$, $X_{n8}$ are P (SEQ ID NO: 136). In some embodiments, any five of $X_{n1}$, $X_{n2}$, $X_{n3}$, $X_{n4}$, $X_{n5}$, $X_{n6}$, $X_{n7}$, $X_{n8}$ are P (SEQ ID NO: 137). In some embodiments, any six of $X_{n1}$, $X_{n2}$, $X_{n3}$, $X_{n4}$, $X_{n5}$, $X_{n6}$, $X_{n7}$, $X_{n8}$ are P (SEQ ID NO: 138). In some embodiments, any seven of $X_{n1}$, $X_{n2}$, $X_{n3}$, $X_{n4}$, $X_{n5}$, $X_{n6}$, $X_{n7}$, $X_{n8}$ are P (SEQ ID NO: 139). In some embodiments, the extension sequence is CPPCPPCPPCPPC (SEQ ID NO: 8). In some embodiments, the C-terminus cysteine is removed. In some embodiments, the N-terminus cysteine is removed. In some embodiments, both terminal cysteines are removed.

In some embodiments, the extension sequence is $CX_{n1}X_{n2}CX_{n3}X_{n4}CX_{n5}X_{n6}CX_{n7}X_{n8}CX_{n9}X_{n10}C$ (SEQ ID NO: 14). $X_{n1}$ can be any amino acid. $X_{n2}$ can be any amino acid. $X_{n3}$ can be any amino acid. $X_{n4}$ can be any amino acid. $X_{n5}$ can be any amino acid. $X_{n6}$ can be any amino acid. $X_{n7}$ can be any amino acid. $X_{n8}$ can be any amino acid. $X_{n9}$ can be any amino acid. $X_{n10}$ can be any amino acid. In some embodiments, any one of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 140). In some embodiments, any two of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, are P (SEQ ID NO: 141). In some embodiments, any three of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 142). In some embodiments, any four of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 143). In some embodiments, any five of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 144). In some embodiments, any six of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 145). In some embodiments, any seven of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 146). In some embodiments, any eight of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 147). In some embodiments, any nine of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$ are P (SEQ ID NO: 148). In some embodiments, the extension sequence is CPPCPPCPPCPPCPPC (SEQ ID NO: 9). In some embodiments, the C-terminus cysteine is removed. In some embodiments, the N-terminus cysteine is removed. In some embodiments, both terminal cysteines are removed.

In some embodiments, the extension sequence is $CX_{n1}X_{n2}CX_{n3}X_{n4}CX_{n5}X_{n6}CX_{n7}X_{n8}CX_{n9}X_{n10}CX_{n11}X_{n12}C$ (SEQ ID NO: 15). $X_{n1}$ can be any amino acid. $X_{n2}$ can be any amino acid. $X_{n3}$ can be any amino acid. $X_{n4}$ can be any amino acid. $X_{n5}$ can be any amino acid. $X_{n6}$ can be any amino acid. $X_{n7}$ can be any amino acid. $X_{n8}$ can be any amino acid. $X_{n9}$ can be any amino acid. $X_{n10}$ can be any amino acid. $X_{n11}$ can be any amino acid. $X_{n12}$ can be any amino acid. In some embodiments, any one of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 149). In some embodiments, any two of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 150). In some embodiments, any three of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 151). In some embodiments, any four of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 152). In some embodiments, any five of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 153). In some embodiments, any six of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 154). In some embodiments, any seven of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 155). In some embodiments, any eight of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 156). In some embodiments, any nine of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 157). In some embodiments, any ten of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 158). In some embodiments, any eleven of $X_{n1}$, $X_{n2}$, $X_{n3}$, $X_{n4}$, $X_{n5}$, $X_{n6}$, $X_{n7}$, $X_{n8}$, $X_{n9}$, $X_{n10}$, $X_{n11}$, $X_{n12}$ are P (SEQ ID NO: 159). In some embodiments, the extension sequence is CPPCPPCPPCPPCPPCPPC (SEQ ID NO: 10). In some embodiments, the C-terminus cysteine is removed. In some embodiments, the N-terminus cysteine is removed. In some embodiments, both terminal cysteines are removed.

In some embodiments, the extension sequence comprises greater than 70% sequence identity to any one of the following extension sequences: CPPC (SEQ ID NO: 7), CPPCPPC (SEQ ID NO: 5), CPPCPPCPPC (SEQ ID NO: 6), CPPCPPCPPCPPC (SEQ ID NO: 8), CPPCPPCPPCPPCPPC (SEQ ID NO: 9), or CPPCPPCPPCPPCPPCPPC (SEQ ID NO: 10), for example, 75%, 85%, or 95%. In some embodiments, a nucleic acid sequence is provided that encodes for one of the following extension sequences: CPPC (SEQ ID NO: 7), CPPCPPC (SEQ ID NO: 5), CPPCPPCPPC (SEQ ID NO: 6), CPPCPPCPPCPPC (SEQ ID NO: 8), CPPCPPCPPCPPCPPC (SEQ ID NO: 9), or CPPCPPCPPCPPCPPCPPC (SEQ ID NO: 10). The nucleic acid sequence can comprise conservative substitutions, which provides a conservatively modified variant of the sequence.

In some embodiments, the extension sequence comprises $GGC(PPC)$. (SEQ ID NO: 11), wherein n is 1, 2, 3, 4, 5, 6, 7, 8, or 9. In some embodiments, the extension sequence comprises $GGC(X_{n1}X_{n2}C)_n$ (SEQ ID NO: 17), wherein n is 1, 2, 3, 4, 5, 6, 7, 8, or 9, and wherein $X_{n1}$ $X_{n2}$ can be any amino acid. In some embodiments, at least 50% of the amino acids within the $X_{n1}$ and $X_{n2}$ are prolines. In some embodiments, at least 60, 70, 80, 90, or 100% of the amino acids within $X_{n1}$ and $X_{n2}$ are prolines.

In some embodiments, the diabody comprises a cys-diabody comprising a heavy chain variable domain, a light chain variable domain and an extension sequence.

Extension sequences can associate the different chains and/or domains in different orientations. In some embodiments, the extension sequence (working as a pair of extension sequences) connects the C-terminus of the first $V_H$ domain to the C-terminus of the second $V_H$ variable domain via a covalent bond (e.g., one or more disulfide bonds). In some embodiments, the extension sequence (working as a pair of extension sequences) connects the C-terminus of the $V_L$ domain to the C-terminus of the $V_L$ domain via a covalent bond (e.g., one or more disulfide bonds). In some embodiments, the covalent bonds involve one or more disulfide bonds via the presence of the cysteines in the extension sequence. Any discussion herein of an extension sequence regarding one orientation also allows for the reverse orientation and both orientations. In some embodiments, 2, 3, 4, 5, 6, or more disulfide bonds are present in the assembled diabody.

Figure 2A:
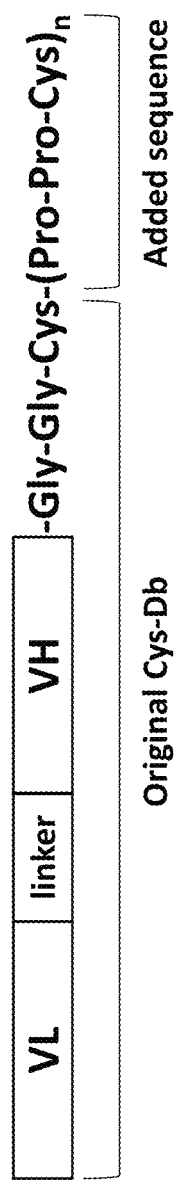
FIG. 2A depicts the structure of the original Cys-diabody in which a (PPC)$_n$ motif has been added.
Figure 2C:
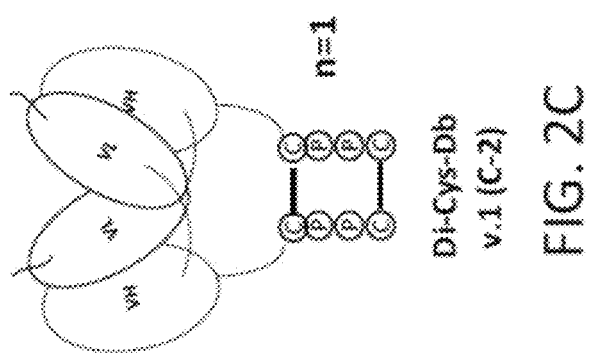
FIG. 2C depicts the structure of a Cys-diabody in which a (PPC) motif has been added.
Figure 2B:
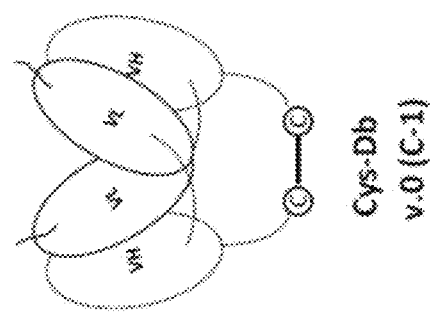
FIG. 2B depicts the structure of the original Cys-diabody.
Figure 2E:
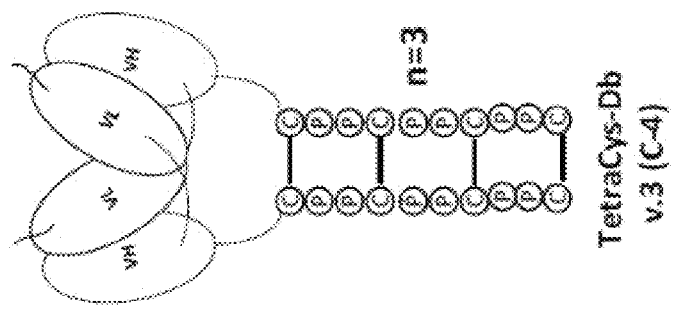
FIG. 2E depicts the structure of a Cys-diabody in which a (PPC)$_3$ motif has been added.
Figure 2D:
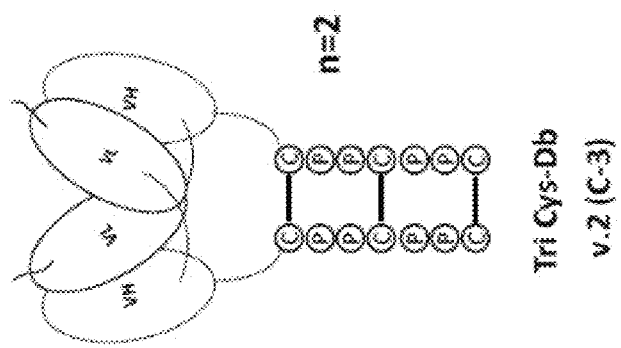
FIG. 2D depicts the structure of a Cys-diabody in which a (PPC)$_2$ motif has been added.

In some embodiments, extension sequences work in pairs, as shown for example in FIGS. 2C, 2D, and 2E. Each extension sequence providing half of the cysteines needed for the targeted number of disulfide bonds. When these extension sequences are paired together, they can be termed "paired extension sequences" or other similar term. Not all of the cysteines need to be paired together in any one paired extension sequence within a diabody in order to obtain a benefit from the extension sequences. For example, unpaired cysteines allow for additional binding sites for other atoms or molecules, such as detectable markers, therapeutic agents, PEG, etc.

In some embodiments, the extension sequences within the diabodies provide the diabodies with additional functional characteristics. In some embodiments, the extension sequence increases the stability of the diabody, for example, through causing a diabody to retain its dimeric protein structure. Retention of the dimeric structure can result in reduced presence of unpaired scFv impurities after purification and analysis of the diabody.

In some embodiments, the extension sequences can impact the binding activity of a diabody by, for example, increasing the affinity of the diabody for an antigen. In some embodiments, the extension sequences have no impact on binding activity of the diabody. In some embodiments, the extension sequence increases the biological activity of the diabody by, for example, causing the diabody to retain its dimeric structure. Examples of increased biological activity include, but are not limited to, causing the diabody to more efficiently target tumors.

In some embodiments, any of the extension sequences described herein comprise at least 3 cysteines. In some embodiments, any of the extension sequences described herein comprise at least 4 cysteines. In some embodiments, any of the extension sequences described herein comprise at least 5 cysteines. In some embodiments, any of the extension sequences described herein comprise at least 6 cysteines. In some embodiments, any of the extension sequences described herein comprise at least 7 cysteines.

In some embodiments, the cysteine residues can be part of a PPC motif. In some embodiments, the extension sequence comprises a repeating PPC motif such as: CPPC (SEQ ID NO; 7), CPPCPPC (SEQ ID NO: 5), CPPCPPCPPC (SEQ ID NO: 6), CPPCPPCPPCPPC (SEQ ID NO: 8), CPPCPPCPPCPPCPPC (SEQ ID NO: 9), or CPPCPPCPPCPPCPPCPPC (SEQ ID NO: 10). In some embodiments the C-terminus cysteine is removed. In some embodiments the N-terminus cysteine is removed. In some embodiments both the C-terminus and N-terminus cysteines are removed.

Linker

In some embodiments, the heavy chain variable domain and light chain variable domain within a single chain can associate in different ways depending on how the linker connects the domains to form the single chain. Linker sequences can allow for a $V_L$-$V_H$ or $V_H$-$V_L$ orientation within the single chain. In some embodiments, the linker connects the C-terminus of the $V_H$ domain to the N-terminus of the $V_L$ domain. In some embodiments, the linker connects the C-terminus of the $V_L$ domain to the N-terminus of the $V_H$ domain. Any disclosure of a linker provided herein regarding one orientation also allows for the reverse orientation and both orientations. In some embodiments, the linker connects the heavy and light chain variable domains via a peptide backbone connection between the $V_H$ and $V_L$ domains.

In some embodiments, the linker is about 1 to about 50 amino acids in length, for example, 2 to 15, 2-14, 3-13, 4-10, or 5 amino acids to 8 amino acids. In some embodiments, more than 1 linker is provided, for example, 2, 3, or 4 linkers. If more than 1 linker is provided, each of the linkers can be the same length or different lengths. In some embodiments, a modified amino acid can be used. Use of (i) different amounts of linkers, (i) different lengths of linkers, and (iii) different orientations of linkers allows for conformational flexibility and range-of-motion of the diabody to ensure formation of disulfide bonds. The linker connects the $V_H$ domain to the $V_L$ domain via the linker's peptide backbone. The linker will link the two domains as a continuous, single chain.

In some embodiments, the linker is a GlySer linker. The GlySer linker can be a polypeptide that is rich in Gly and/or Ser residues. In some embodiments, at least about 40% of the amino acid residues of the GlySer linker are Gly, Ser, or a combination of Gly and Ser, for example at least about 40%, 50%, 60%, 70%, 80%, or 90%. In some embodiments, the GlySer linker is at least about 2 amino acids long, for example at least about 3, 4, 5, 6, 7, 8, 9, 10, 11, 12, 13, 14, 15, 16, 17, 18, 19, 20, 25, 30, 35, or 40 amino acids long. In some embodiments, the linker comprises at least one threonine. In some embodiments, the linker is short enough to allow for cross-pairing between the domains in the diabody (such that the $V_L$ and $V_H$ domains within a single chain do not form a binding domain, but instead the binding domains are formed between the two chains, e.g., a $V_H$ from a first chain with a $V_L$ from a second chain and a $V_L$ from the first chain with the $V_H$ from the second chain).

Method of Making a Diabody

In some embodiments methods of making the diabodies, antigen binding constructs, or extension sequences described herein are provided. In some embodiments cell lines are provided that produce any of the diabodies, antigen binding constructs, or extension sequences described herein. The cell lines can be a mammalian cell such as the CHO-K1 cell line. In some embodiments, a method of making a diabody in yeast is provided. The method comprises providing yeast comprising a nucleic acid encoding any of the diabodies described herein and expressing any of the diabodies described herein. In some embodiments, one or more of a wide variety of mammalian or non-mammalian expression systems are used to produce the diabodies, antigen binding constructs, or extension sequences disclosed herein including, but not limited to mammalian expression systems (for example, CHO-K1 cells), bacterial expression systems (for example, *E. coli, B. subtilis*) yeast expression systems (for example, *Pichia, S. cerevisiae*) or any other known expression system. Other systems can include insect cells and/or plant cells.

In some embodiments, any of the extension and/or linker sequences can be employed in one or more of the antigen binding constructs, e.g., diabody, provided herein. In some embodiment, the diabody has some or all of the amino acid sequence shown in FIGS. 22-24. In some embodiments, the diabody is at least 80% identical to any one or more of SEQ ID NO: 161-163, e.g., 80, 85, 90, 91, 92, 93, 94, 95, 96, 97, 98, 99%, or higher. In some embodiments, the percent identity is at least 80% identical to any one or more of SEQ ID NO: 161-163, e.g., 80, 85, 90, 91, 92, 93, 94, 95, 96, 97, 98, 99%, or higher but the extension sequence within the sequence is 100% identical to one or more of the sequences provided herein.

Method of Use/Diabody Kit

In some embodiments kits are provided that comprise an antigen binding construct that comprises an extension sequence and a detectable marker. Any of the extension sequences provided herein can be employed. In some embodiments, the extension sequences include EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPC (SEQ ID NO: 7), CPPCPPC (SEQ ID NO: 5), CPPCPPCPPC (SEQ ID NO: 6), CPPCPPCPPCPPC (SEQ ID NO: 8), CPPCPPCPPCPPCPPC (SEQ ID NO: 9), CPPCPPCPPCPPCPPCPPC (SEQ ID NO: 10), or GGC (PPC)$_n$ (SEQ ID NO: 11), wherein n is 2, 3, 4, 5, 6, 7, 8, or 9, and wherein X$_{n1}$, X$_{n2}$, X$_{n3}$, X$_{n4}$, and X$_{n5}$ can be any amino acid. Detectable markers include, but are not limited to, a radioisotope, a fluorescent compound, a bioluminescent compound, a chemiluminescent compound, a metal chelator or an enzyme. The extension sequence can be on the end of a heavy or light chain variable region of a diabody.

In some embodiments kits are provided that comprise a diabody that comprise an extension sequence and a detectable marker. Any of the extension sequences provided herein can be employed. Extension sequences include EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPC (SEQ ID NO: 7) CPPCPPC (SEQ ID NO: 5), CPPCPPCPPC (SEQ ID NO: 6), CPPCPPCPPCPPC (SEQ ID NO: 8), CPPCPPCPPCPPCPPC (SEQ ID NO: 9), CPPCPPCPPCPPCPPCPPC (SEQ ID NO: 10), or GGC (PPC)$_n$ (SEQ ID NO: 11), wherein n is 2, 3, 4, 5, 6, 7, 8, or 9, and wherein X$_{n1}$, X$_{n2}$, X$_{n3}$, X$_{n4}$, and X$_{n5}$ can be any amino acid. Detectable markers include, but are not limited to, a radioisotope, a fluorescent compound, a bioluminescent compound, a chemiluminescent compound, a metal chelator or an enzyme.

In some embodiments a method is provided for detecting the presence or absence of a marker. The method comprises applying any of the diabodies described herein to a sample and detecting the presence or absence of a marker. Markers (or targets) that can be employed include, but are not limited to, PCSA, PMSA, CD8, PDL-1, Her2/neu. In some embodiments, any target or marker can be selected.

In some embodiments, the diabody is incubated with the sample for no more than 20 hours. In some embodiments, the diabody is incubated with the sample for no more than 6 hours. In some embodiments, there is no time limit for how long the diabody is incubated with the sample.

Methods of Treatment

In some embodiments, a method of treatment is provided comprising administering a therapeutically effective amount of the pharmaceutical composition of the diabody (which will include one or more of the disclosed extension sequences) to an individual in need thereof. The pharmaceutical compositions described herein can be administered by any suitable route of administration. A route of administration can refer to any administration pathway known in the art, including but not limited to aerosol, enteral, nasal, ophthalmic, oral, parenteral, rectal, transdermal (e.g., topical cream or ointment, patch), or vaginal. "Transdermal" administration can be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the antigen binding construct can be delivered intraoperatively as a local administration during an intervention or resection.

In some embodiments any of the pharmaceutical compositions or therapeutic agents described herein can be used to target a therapeutic molecule, for example a cytotoxin, to a target positive cell, such as a cell expressing the target molecule. Thus, some embodiments include methods of targeting a therapeutic agent or a pharmaceutical composition to a target positive cell. The method can include administering a pharmaceutical composition or therapeutic agent to a subject. The subject can be a subject in need, for example a subject in need of elimination or neutralization of at least some target positive cells. In some embodiments, the therapeutic agent or pharmaceutical composition can be directly conjugated to the extension sequence, antigen binding construct, or diabody via a covalent bond, such as a disulfide bond. In some embodiments, the subject can benefit from the localization of a target molecule positive cell to another cell or agent.

In some embodiments, before and/or after administration of the therapeutic agent or pharmaceutical composition, the number and/or localization of the target positive cells of the patient is determined. For example, determining the number and/or localization of target positive cells prior to administration can indicate whether the patient is likely to benefit from neutralization and/or elimination of the target positive cells. Determining the number and/or localization of the target positive cells after administration can indicate whether the target positive cells were eliminated in the patient.

In some embodiments, the disorder to be treated is one that expresses an elevated level of at least one of PSCA, PSMA, CD8, HER2/new and/or PSMA and CD3. In some embodiments, the disorder to be treated is one that can be targeted and/or detected by a diabody that binds to at least one of PSCA, PSMA, CD8, HER2/new and/or PSMA and CD3.

In some embodiments, diabody IAB1C (JAB1C-1, IAB1C-2 and/or JAB1C-3) can be used to target (including deliver a payload to) a PSCA expressing cell for treatment of a disorder related thereto.

In some embodiments, diabody IAB2C (IAB2C-1, IAB2C-2 and/or IAB2C-3) can be used to target (including deliver a payload to) a PSMA expressing cell for treatment of a disorder related thereto.

In some embodiments, diabody IAB22C (IAB22C-1, IAB22C-2 and/or IAB22C-3) can be used to target (including deliver a payload to) a CD8 expressing cell for treatment of a disorder related thereto.

In some embodiments, diabody IAB8C (IAB8C-1, IAB8C-3 and/or IAB8C-4) can be used to target (including deliver a payload to) a Her2/neu expressing cell for treatment of a disorder related thereto.

In some embodiments, diabody bC-PSMAxCD3-1 bC-CD3xPSMA-1 or bC-PSMAxCD3-3bC-CD3xPSMA-3 can be used to target (including deliver a payload to) a PSMAxCD3 expressing cell for treatment of a disorder related thereto.

In some embodiments, a method for reducing cells expressing PCSA, PSMA, CD8, HER2, CD3, 5T4, PD-L1, folate receptor alpha, Mesothelin, CA19-9, CD19, CD20, and/or Her2/neu is provided. The method comprises using one or more of the diabodies with the extension sequence(s) provided herein, with a therapeutic agent, cytotoxin, or other payload to deliver the payload to the cells expressing one or more of: PCSA, PSMA, CD8, HER2, CD3, 5T4, PD-L1, folate receptor alpha, Mesothelin, CA19-9, CD19, CD20, and/or Her2/neu.

In some embodiments, a method of detecting a cell expressing or overexpressing one or more of PCSA, PSMA, CD8, HER2, CD3, 5T4, PD-L1, folate receptor alpha, Mesothelin, CA19-9, CD19, CD20, and/or Her2/neu is provided. The method comprises using one or more of the diabodies with the extension sequence(s) provided herein, with a detectable marker to localize the detectable marker to the cells expressing one or more of: PCSA, PSMA, CD8, HER2, CD3, 5T4, PD-L1, folate receptor alpha, Mesothelin, CA19-9, CD19, CD20, and/or Her2/neu.

In some embodiments, the diabody or other antigen binding construct provided herein can be used in the treatment and/or prevention of one or more of: non-small cell lung cancer (NSCLC), Small Cell Lung Cancer (SCLC), Thymic Carcinoma, Lymphoma, Myxoid/Round Cell Liposarcoma, Liposarcoma, Synovial Sarcoma, Recurrent Adult Soft Tissue Sarcoma, Gliosarcoma, Astrocytoma, Acute Myelogenous Leukemia (AML), Malignant Solitary Fibrous Tumor of the Pleura (MSFT), Penile Cancer, Diffuse Intrinsic Pontine Glioma (DIPG), Thyroid Carcinoma, Head and neck Squamous Carcinoma (SCCHN), Adenocarcinoma of the Lung, Vulvar Cancer (squamous cell carcinoma), Bladder Cancer, Cervical Squamous Cell Carcinoma, Germ Cell Tumors, Testicular Cancer, Pancreatic Ductal Adenocarcinoma, Pancreatic Adenocarcinoma, Non-Melanoma Skin Cancers, Retroperitoneal and Peritoneal Carcinoma, Melanoma, Unresectable or Metastatic Melanoma, Mucosal Melanoma of the Head and Neck, Uveal Melanoma, Non-Cutaneous Melanoma, Cutaneous T-Cell Lymphoma, Occult Primary tumors, Biliary Cancer, Gastrointestinal Stromal Tumors (GIST), Mesothelioma, Biphasic Mesothelioma, Malignant Pleural Mesothelioma, Kidney cancer, Myelodysplastic syndrome, Liver Hepatocellular Carcinoma, Esophageal and Esophagogastric Junction Carcinoma, Extrahepatic Bile Duct Adenocarcinoma, Small Intestinal Malignancies, Gastric Adenocarcinoma, Cholangiocarcinoma, Intrahepatic ad extrahepatic Cholangiocarcinomas, Ovarian Surface Epithelial Carcinomas, Non-epithelial and epithelial Ovarian cancers, Breast Carcinoma, Triple Negative Breast Cancer, Endometrial carcinoma, Uterine sarcoma, Bone Cancers, Colorectal Adenocarcinoma, Prostatic Adenocarcinoma, Hormone-Resistant Prostate Cancer, Neuroendocrine tumors, Solid tumors, Follicular Lymphoma, Kaposi Sarcoma, Carcinoma of the Genitourinary Tract, Fallopian Tube Cancer, Malignant Glioma, Waldenstrom Macroglobulinemia, Richter Syndrome, Refractory Splenic Marginal Zone Lymphoma, Refractory Small Lymphocytic Lymphoma, Refractory Nodal Marginal Zone Lymphoma, Refractory Lymphoplasmacytic Lymphoma, Refractory Extranodal Marginal Zone Lymphoma of the Mucosa-Associated Lymphoid Tissue, Refractory Chronic Lymphocytic Leukemia, Multiple Myeloma, Hodgkin's Lymphoma, Non-Hodgkin's Lymphoma, Diffuse Large B-Cell Lymphoma, Nasopharyngeal Carcinoma, Gastroesophageal Junction Adenocarcinoma, renal cell carcinomas, colon carcinomas, Transitional cell carcinoma (TCC), urothelial carcinoma (UCC), glioblastoma multiforme (GBM), Gallbladder cancers, and Merkel Cell Carcinoma.

In some embodiments, the diabody or other antigen binding construct provided herein can be used in the treatment and/or prevention of one or more of: Prostate cancer, Lung cancers, Melanoma, Breast malignancies, CNS and brain Malignancies, Skin malignancies, Occult Primary tumors, Kidney cancers, Gastrointestinal malignancies, Ovarian Neoplasms, Renal Cancers, Biliary Cancer, Bladder cancer, Esophageal Neoplasms, Cervical cancers, Solid tumors, Head and neck cancers, Urogenital Neoplasms, Germ Cell Tumors, Testicular Cancer, Pancreatic cancers, Glioma, Liver cancers, Malignant Neoplasms of the Bone, Colorectal cancers, Thyroid Cancer, Thoracic and respiratory tumors, Lymphomas, Male and female genitourinary Malignancies, Bile duct cancers, Hematological Malignancies, Multiple Myeloma, Gallbladder cancers, endocrine tumors, ocular cancers, and Tumors of the hematopoietic and lymphoid tissues. In some embodiments, the diabody or other antigen binding construct provided herein can be used in the treatment and/or prevention of one or more of: Non-Small Cell Lung Cancer (NSCLC), Prostate Cancer, Melanoma, and Breast Cancer.

In some embodiments, any one or more of the methods of treatment noted above can instead be a method of preparing a medicament for the treatment of any one or more of the indications noted above, In some embodiments, any one or more of the diabodies and/or antigen binding constructs provided herein can be used as a composition for the treatment of any one or more of: non-small cell lung cancer (NSCLC), Small Cell Lung Cancer (SCLC), Thymic Carcinoma, Lymphoma, Myxoid/Round Cell Liposarcoma, Liposarcoma, Synovial Sarcoma, Recurrent Adult Soft Tissue Sarcoma, Gliosarcoma, Astrocytoma, Acute Myelogenous Leukemia (AML), Malignant Solitary Fibrous Tumor of the Pleura (MSFT), Penile Cancer, Diffuse Intrinsic Pontine Glioma (DWG), Thyroid Carcinoma, Head and neck Squamous Carcinoma (SCCHN), Adenocarcinoma of the Lung, Vulvar Cancer (squamous cell carcinoma), Bladder Cancer, Cervical Squamous Cell Carcinoma, Germ Cell Tumors, Testicular Cancer, Pancreatic Ductal Adenocarcinoma, Pancreatic Adenocarcinoma, Non-Melanoma Skin Cancers, Retroperitoneal and Peritoneal Carcinoma, Melanoma, Unresectable or Metastatic Melanoma, Mucosal Melanoma of the Head and Neck, Uveal Melanoma, Non-Cutaneous Melanoma, Cutaneous T-Cell Lymphoma, Occult Primary tumors, Biliary Cancer, Gastrointestinal Stromal Tumors (GIST), Mesothelioma, Biphasic Mesothelioma, Malignant Pleural Mesothelioma, Kidney cancer, Myelodysplastic syndrome, Liver Hepatocellular Carcinoma, Esophageal and Esophagogastric Junction Carcinoma, Extrahepatic Bile Duct Adenocarcinoma, Small Intestinal Malignancies, Gastric Adenocarcinoma, Cholangiocarcinoma, Intrahepatic ad extrahepatic Cholangiocarcinomas, Ovarian Surface Epithelial Carcinomas, Non-epithelial and epithelial Ovarian cancers, Breast Carcinoma, Triple Negative Breast Cancer, Endometrial carcinoma, Uterine sarcoma, Bone Cancers, Colorectal Adenocarcinoma, Prostatic Adenocarcinoma, Hormone-Resistant Prostate Cancer, Neuroendocrine tumors, Solid tumors, Follicular Lymphoma, Kaposi Sarcoma, Carcinoma of the Genitourinary Tract, Fallopian Tube Cancer, Malignant Glioma, Waldenstrom Macroglobulinemia, Richter Syndrome, Refractory Splenic Marginal Zone Lymphoma, Refractory Small Lymphocytic Lymphoma, Refractory Nodal Marginal Zone Lymphoma, Refractory Lymphoplasmacytic Lymphoma, Refractory Extranodal Marginal Zone Lymphoma of the Mucosa-Associated Lymphoid Tissue, Refractory Chronic Lymphocytic Leukemia, Multiple Myeloma, Hodgkin's Lymphoma, Non-Hodgkin's Lymphoma, Diffuse Large B-Cell Lymphoma, Nasopharyngeal Carcinoma, Gastroesophageal Junction Adenocarcinoma, renal cell carcinomas, colon carcinomas, Transitional cell carcinoma (TCC), urothelial carcinoma (UCC), glioblastoma multiforme (GBM), Gallbladder cancers, Merkel Cell Carcinoma, Prostate cancer, Lung cancers, Melanoma, Breast malignancies, CNS and brain Malignancies, Skin malignancies, Occult Primary tumors, Kidney cancers, Gastrointestinal malignancies, Ovarian Neoplasms, Renal Cancers, Biliary Cancer, Bladder cancer, Esophageal Neoplasms, Cervical cancers, Solid tumors, Head and neck cancers, Urogenital Neoplasms, Germ Cell Tumors, Testicular Cancer, Pancreatic cancers, Glioma, Liver cancers, Malignant Neoplasms of the Bone, Colorectal cancers, Thyroid Cancer, Thoracic and respiratory tumors, Lymphomas, Male and female genitourinary Malignancies, Bile duct cancers, Hematological Malignancies, Multiple Myeloma, Gallbladder cancers, endocrine tumors, ocular cancers, and Tumors of the hematopoietic and lymphoid tissues. In some embodiments, the diabody or other antigen binding construct provided herein can be used in the treatment and/or prevention of one or more of: Non-Small Cell Lung Cancer (NSCLC), Prostate Cancer, Melanoma, and Breast Cancer.

In some embodiments, the diabody and/or antigen binding construct is present in an amount effective for reducing one or more symptom of any one or more of the disorders provided herein. In some embodiments, the diabody and/or antigen binding construct is conjugated to a therapeutic agent and/or cytotoxic agent for the therapy or therapeutic.

Nucleic Acids

In some embodiments, a nucleic acid sequence is provided that encodes any of the diabodies disclosed herein. In some embodiments, a nucleic acid sequence is provided that encodes any of the extension sequences disclosed herein. In some embodiments, an expression vector is provided that comprises these nucleic acid sequences. In some embodiments, the expression vector includes pcDNA3.1™/myc-His (−) Version A vector for mammalian expression (Invitrogen, Inc.) or a variant thereof. The pcDNA3.1 expression vector features a CMV promoter for mammalian expression and both mammalian (Neomycin) and bacterial (Ampicillin) selection markers. In some embodiments, the expression vector includes a plasmid. In some embodiments, the vector includes a viral vector, for example a retroviral or adenoviral vector. In embodiments, the vector includes a cosmid, YAC, or BAC.

Any of the extension sequences described herein can be configured for use within an antigen binding construct. In some embodiments, the extension sequence is located within an antibody fragment. In some embodiments, the extension sequence is located within antibody. The antibody can be mono-specific or bi-specific. Bi-specific antibodies can be assembled in a 1:1 ratio. In some embodiments, the extension sequence is part of a diabody. In some embodiments, the extension sequence is part of a diabody that is disclosed in Table 2.1.

In some embodiments a nucleic acid sequence is provided that encodes for any of the extension sequences described herein.

In some embodiments a vector is provided that comprises a nucleic acid that encodes for any of the extension sequences, antigen binding constructs, or diabodies described herein. In some embodiments, the vector includes pcDNA3.1™/myc-His (−) Version A vector for mammalian expression (Invitrogen, Inc.) or a variant thereof. The pcDNA3.1 expression vector features a CMV promoter for mammalian expression and both mammalian (Neomycin) and bacterial (Ampicillin) selection markers. In some embodiments, the expression vector includes a plasmid. In some embodiments, the vector includes a viral vector, for example a retroviral or adenoviral vector. In embodiments, the vector includes a cosmid, YAC, or BAC.

Therapeutic Agent

In some embodiments any of the extension sequences, antibody binding constructs, or diabodies described herein can be covalently attached to one or more additional molecules, such as a therapeutic agent or detectable marker. A therapeutic agent as used herein is an atom, molecule, or compound that is useful in the treatment of a disorder related to a target molecule. Examples of therapeutic agents include, but are not limited to, drugs, chemotherapeutic agents, therapeutic antibodies and antibody fragments, toxins, radioisotopes, enzymes (for example, enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles. In some embodiments, the extension sequences can be connected to a therapeutic agent to a disorder associated with the expression of a target molecule. In some embodiments, 1, 2, 3, 4, 5, 6, 7, 8, 9, 10, 11, 12 or more molecules of therapeutic agents can be attached to each pair of extension sequences (for example 1, 2, 3, 4, 5, or 6 agents on each strand).

In some embodiments the agent is a cytotoxic agent. In some embodiments, the cytotoxic agent is one such as maytansine, auristatin, PBD, docetaxel, or etoposide. Additional embodiments of cytotoxic agents include ricin, doxorubicin, daunorubicin, taxol, ethiduim bromide, mitomycin, tenoposide, vincristine, vinblastine, colchicine, dihydroxy anthracin dione, actinomycin D, diphtheria toxin, Pseudomonas exotoxin (PE) A, PE40, abrin, and glucocorticoid and other chemotherapeutic agents, as well as radioisotopes. Embodiments of cytotoxins further include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that can be used as detectable markers in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, alltransretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte—colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, maytansinoids, auristatins and pyrrolobenzodiazepines, or zoledronic acid.

In some embodiments a pharmaceutical composition is provided that comprises any of the extension sequences, antigen binding constructs, or diabodies described herein. In some embodiments, the pharmaceutical composition can also include a pharmaceutically acceptable carrier. A pharmaceutically acceptable carrier can be a pharmaceutically acceptable material, composition, or vehicle that is involved in carrying or transporting a compound of interest from one tissue, organ, or portion of the body to another tissue, organ, or portion of the body. For example, the carrier can be a liquid or solid filler, diluent, excipient, solvent, or encapsulating material, or some combination thereof. Each component of the carrier is "pharmaceutically acceptable" in that it is compatible with the other ingredients of the formulation. It is also suitable for contact with any tissue, organ, or portion of the body that it can encounter, meaning that, ideally it will not carry a significant risk of toxicity, irritation, allergic response, immunogenicity, or any other complication that excessively outweighs its therapeutic benefits.

In some embodiments, a therapeutic agent is provided that is covalently attached to any of the extension sequences, antigen binding constructs, or diabodies described herein. Examples of therapeutic agents include, but are not limited to, drugs, chemotherapeutic agents, therapeutic antibodies and antibody fragments, toxins, radioisotopes, enzymes (for example, enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles.

In some embodiments a pharmaceutical composition comprising any of the extension sequences described herein is provided. In some embodiments the pharmaceutical composition comprises a diabody that comprises an extension sequence or an antigen binding construct that comprises an extension sequence. In some embodiments a pharmaceutical composition comprising any one or more of the following sequences: EPKSX$_{n5}$DKTHTCX$_{n1}$X$_{n2}$CX$_{n3}$X$_{n4}$C (SEQ ID NO: 1), ERKX$_{n5}$CX$_{n1}$X$_{n2}$CX$_{n3}$X$_{n4}$C (SEQ ID NO: 2), ELKTPLGDTTHTCX$_{n1}$X$_{n2}$CX$_{n3}$X$_{n4}$C (SEQ ID NO: 3), ESKYGPPCX$_{n1}$X$_{n2}$CX$_{n3}$X$_{n4}$C (SEQ ID NO: 4), CPPC (SEQ ID NO: 7) CPPCPPC (SEQ ID NO: 5), CPPCPPCPPC (SEQ ID NO: 6), CPPCPPCPPCPPC (SEQ ID NO: 8), CPPCPPCPPCPPCPPC (SEQ ID NO: 9), CPPCPPCPPCPPCPPCPPC (SEQ ID NO: 10), or and GGC (PPC)$_n$ (SEQ ID NO: 11), wherein n is 2, 3, 4, 5, 6, 7, 8, or 9, and wherein X$_{n1}$, X$_{n2}$, X$_{n3}$, X$_{n4}$, and X$_{n5}$ can be any amino acid.

In some embodiments, the pharmaceutical composition can also include a pharmaceutically acceptable carrier. A pharmaceutically acceptable carrier can be a pharmaceutically acceptable material, composition, or vehicle that is involved in carrying or transporting a compound of interest from one tissue, organ, or portion of the body to another tissue, organ, or portion of the body. For example, the carrier can be a liquid or solid filler, diluent, excipient, solvent, or encapsulating material, or some combination thereof. Each component of the carrier is "pharmaceutically acceptable" in that it is compatible with the other ingredients of the formulation. It is also suitable for contact with any tissue, organ, or portion of the body that it can encounter, meaning that, ideally it will not carry a significant risk of toxicity, irritation, allergic response, immunogenicity, or any other complication that excessively outweighs its therapeutic benefits.

Detectable Marker

As used herein, a "detectable marker" includes an atom, molecule, or compound that is useful in diagnosing, detecting or visualizing a location and/or quantity of a target molecule, cell, tissue, organ and the like. Detectable markers that can be used in accordance with the embodiments herein include, but are not limited to, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, some nanoparticles, for example quantum dots and metal nanoparticles (described below) can be suitable for use as a detection agent. In some embodiments, the detectable marker is IndoCyanine Green (ICG) or one of the dyes that fluoresces in the near infrared region such as IR800 for surgical applications.

Exemplary radioactive substances that can be used as detectable markers in accordance with the embodiments herein include, but are not limited to, $^{18}$F, $^{18}$F-FAC, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{90}$Y, $^{89}$Sr, $^{89}$Zr, $^{94}$Tc, $^{94}$Tc, $^{99}$mTc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Exemplary Paramagnetic ions substances that can be used as detectable markers include, but are not limited to ions of transition and lanthanide metals (e.g. metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

In some embodiments, the detectable marker can be a radionuclide such as Yttrium-90, Lutetium-177, or Actinium-227. Additional embodiments of a radionuclide include Copper-67, Astatine-211, Lead-212/Bismuth-212, Actinium-225/Bismuth-213, and Thorium. In some embodiments, treatment of a target cell with these radionuclides can result in cell damage and death to a target tissue.

In some embodiments, the detectable marker is a bioluminescence or fluorescent compound Examples include, fluorescein, fluorescein isothiocyanate (FITC), OREGON GREEN™, rhodamine, Texas red, tetrarhodimine isothiocynate (TRITC), Cy3, Cy5, and the like), fluorescent markers (e.g., green fluorescent protein (GFP), phycoerythrin, and the like), autoquenched fluorescent compounds that are activated by tumor-associated proteases, enzymes (e.g., luciferase, horseradish peroxidase, alkaline phosphatase, and the like), nanoparticles, biotin, digoxigenin or combination thereof.

In some embodiments, any of the detectable markers described herein can be conjugated to the diabody.

PEG

In some embodiments, any of the extension sequences, antigen binding constructs or diabodies described herein further comprise polyethylene glycol (PEG). PEG can be conjugated to a cysteine, lysine, histidine, arginine, aspartic acid, serine, or threonine of the extension sequence. In some embodiments, PEG is conjugated to a terminal cysteine of the diabody. The PEG can be a branched polyether or a linear polyether. The PEG can have terminal hydroxyl groups. In some embodiments, PEG increases the half-life of the diabody. In some embodiments, PEG controls the route of clearance. Examples of controlling the route of clearance include reducing blood clearance of the diabody and preventing clearance of the diabody through the kidney. In some embodiments, PEG results in higher tumor uptake of the diabody.

In some embodiments, any of the above options (therapeutic agents, detectable markers, PEG) or other options (such as carbohydrates) can be attached at one or more of the cysteines in the extension sequence(s). In some embodiments, 1, 2, 3, 4, 5, 6, 7, 8, 9, 10, or more such atoms or molecules are attached to the extension sequence(s). In some embodiments, different combinations of these molecules can be attached (for example, a detectable marker and a PEG and a therapeutic agent).

Example 1

Cys-Diabody Constructs

The original Cys-diabody was designed to form a single Cys-Cys bridge at the C-terminus when the $V_L$-linker-$V_H$-GGC monomers assemble into a diabody. Cys-diabody can be assembled in both $V_L$-linker-$V_H$-GGC and $V_H$-linker-$V_L$-GGC configurations as shown in FIG. 1. Cys residues are added to the C-terminus of the construct with Gly-Gly spacer. The purpose of adding these GGC sequences is to enable site-specific conjugation.

Studies showed that insertion of a repeating "PPC" (Pro-Pro-Cys) motif into a hinge of a human IgG1 based minibody molecule results in stabilization of minibody dimers and proper disulfide pairing. $(PPC)_n$ motifs were added to the C-terminus of the Cys-Db (FIGS. 2A and 2B) to determine if they could stabilize the diabody without introducing significant levels of aggregation. Experimentally n=1 (two total cysteines; FIG. 2C), n=2 (three cysteines; FIG. 2D) and n=4 (four cysteines; FIG. 2E) motifs were tested. Additional cysteine residues were added to determine if they allowed for site-specific conjugation while maintaining the protein as an intact dimer.

Figures 3A, 3B:
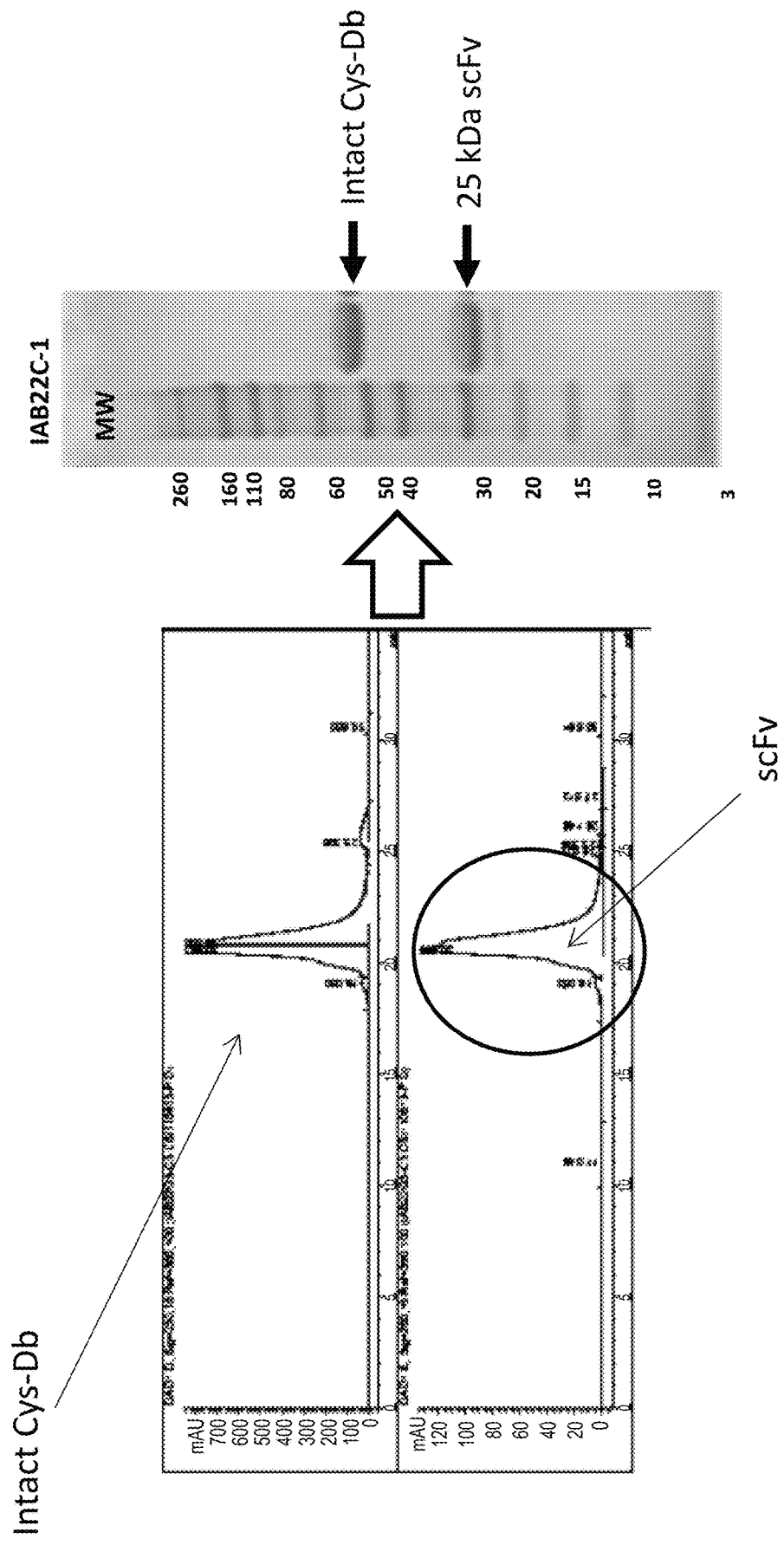
FIG. 3A depicts HPLC that shows peaks that corresponding to both an intact Cys-diabody and single chain fragment variable.
FIG. 3B depicts an SDS-PAGE gel that shows bands that correspond to both an intact Cys-diabody and a single chain fragment variable. Samples used for analysis were derived both from mammalian and yeast cells.

Expression of the Cys-Db-v0 (FIG. 2B) in a mammalian and/or yeast cells yielded a protein with approximately 10-50% of dimer protein that lacks a proper Cys-Cys bridge (variability was observed depending on the CDRs). When a Db containing a single Cys was run on a denaturing, non-reducing SDS-PAGE gel, a prominent 25 kDa band corresponding to the single chain was always present (FIG. 3B). The 25 kDa fragment is the single chain fragment variable (scFv) of the Cys-diabody (i.e. scFv dimer) that dissociated upon electrophoresis in the presence of SDS. A diabody containing a single Cys at the C-terminus maintained its intact dimeric form in solution based on noncovalent, inter-domain affinity of $V_L$ and $V_H$ chains as shown by SE-HPLC chromatography—a single, 50 kDa peak was usually detected on SEC (See FIG. 3A).

Uncoupled scFvs may arise during intracellular processing or post-secretion. The amount of scFv varies depending on the CDRs in the construct. It is reasonable to hypothesize that there is either a "strain" or an "excessive flexibility" at the C-termini of the individual scFv chains in the Cys-Db that contributes to heterogeneity during initial intracellular assembly or secretion into culture media.

Example 2

Synthesizing Monospecific and Bi-Specific Cys-Diabody Proteins

DNA expression constructs that encode for Cys-diabody proteins were synthesized that contain different CPPC (SEQ ID NO: 7) extension sequence motifs (Table 2.1).

TABLE 2.1

| | PSCA IAB1C | PSMA IAB2C | CD8 IAB22C | Her2/neu IAB8C | PSMAxCD3 Bs (huOKT3) |
|---|---|---|---|---|---|
| 1 Cys (GGC) | IAB1C-1 | IAB2C-1 | IAB22C-1 (e.g., FIG. 22) | IAB8C-1 | bC-PSMAxCD3-1 bC-CD3xPSMA-1 |
| 2 Cys; (CPPC; SEQ ID NO: 7) | IAB1C-2 | IAB2C-2 | IAB22C-2 (e.g., FIG. 23) | NA | NA |
| 3 Cys; (CPPCPPC; SEQ ID NO: 5) | IAB1C-3 | IAB2C-3 | IAB22C-3 (e.g., FIG. 24) | IAB8C-3 | bC-PSMAxCD3-3 bC-CD3xPSMA-3 |
| 4 Cys; (CPPCPPCPPC; SEQ ID NO: 6) | | | | IAB8C-4 | |

Example 3

Non-Reducing SDS-Page Analysis Revealed that Increasing the CPPC (SEQ ID NO: 7) Motifs to the Expression Constructs Resulted in Increased Stability Protein samples were evaluated for the presence of dimeric and scFvs using Sodium Dodecyl Sulfate (SDS) polyacrylamide gel electrophoresis (SDS-PAGE) under non-reducing conditions. Samples were prepared by dissolving 3-5 µg of each protein in 10 µL NuPAGE LDS sample buffer (Life Technologies). Each sample was loaded onto 1.0 mm, 12-well 4-12% Bis-Tris Protein Gel cassette (NuPAGE Novex), and the proteins separated after applying a constant potential of 198V for 35 minutes The sizes of the half molecules were determined using SDS-PAGE analysis and reducing conditions. Briefly, a 1:100 dilutions of b-mercaptoethanol was added to the sample buffer. The samples were incubated at 70° C. for 5 minutes prior to loading onto the gels. Each sample was loaded onto a 1.0 mm, 12-well 4-12% Bis-Tris Protein Gel cassette (NuPAGE Novex), and a constant potential of 198V was applied for 35 minutes.

The gels were removed from the plastic cassette and incubated in deionized water for 3 times for 5 minutes. The protein staining was completed by incubating the gel for 2 hours in a solution of Coomassie blue dye (GelCode Blue Safe Protein Stain, Thermo Scientific).

Figures 4A, 4B, 4C:
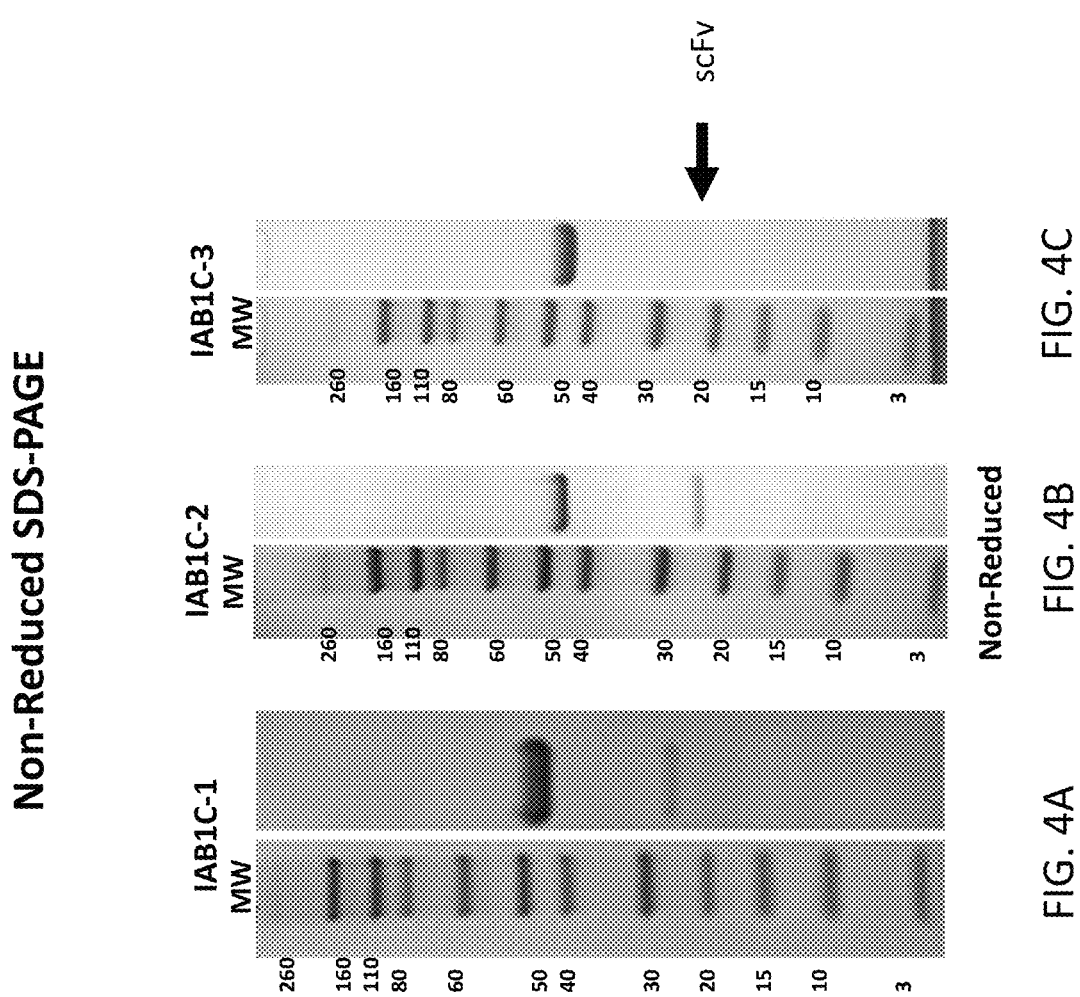
FIG. 4A depicts an SDS-PAGE gel that shows bands that correspond to both an intact Cys-diabody and a single chain fragment variable derived from the IAB1C-1 construct.
FIG. 4B depicts an SDS-PAGE gel that shows bands that correspond to both an intact Cys-diabody and a single chain fragment variable derived from the IAB1C-2 construct.
FIG. 4C depicts an SDS-PAGE gel that shows bands that correspond to an intact Cys-diabody from the IAB1C-3 construct with no detectable scFV.
Figures 6A, 6B, 6C:
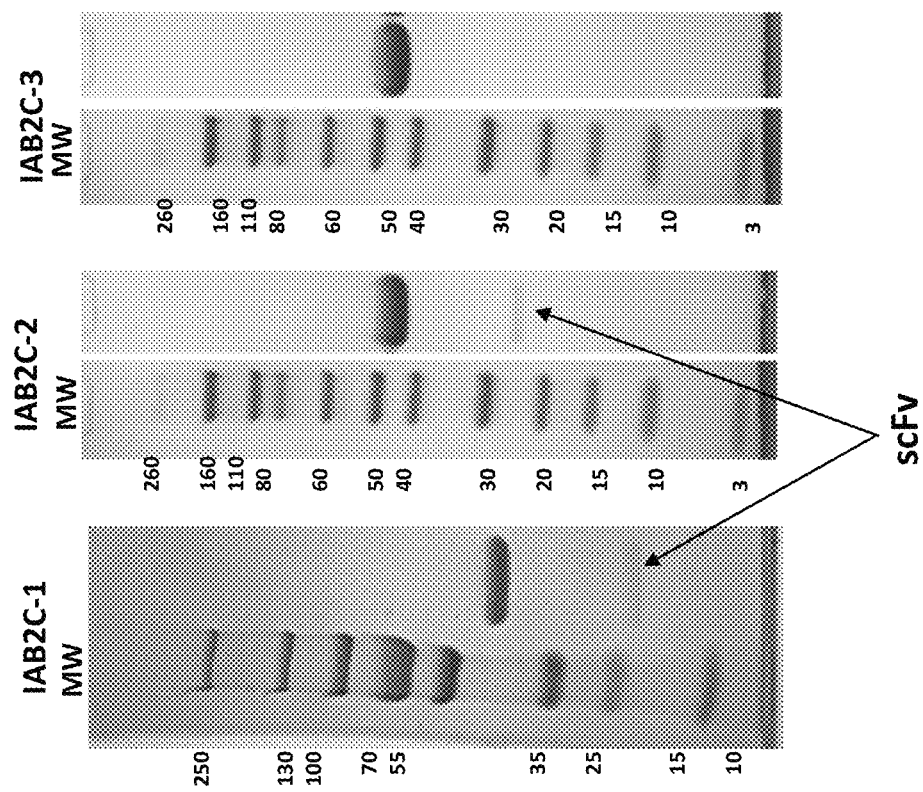
FIG. 6A depicts an SDS-PAGE gel that shows bands that correspond to both an intact Cys-diabody and a single chain fragment variable derived from the IAB2C-1 construct.
FIG. 6B depicts an SDS-PAGE gel that shows bands that correspond to both an intact Cys-diabody and a single chain fragment variable derived from the IAB2C-2 construct.
FIG. 6C depicts an SDS-PAGE gel that shows bands that correspond to an intact Cys-diabody from the IAB2C-3 construct with no detectable scFv.
Figures 8A, 8B, 8C:
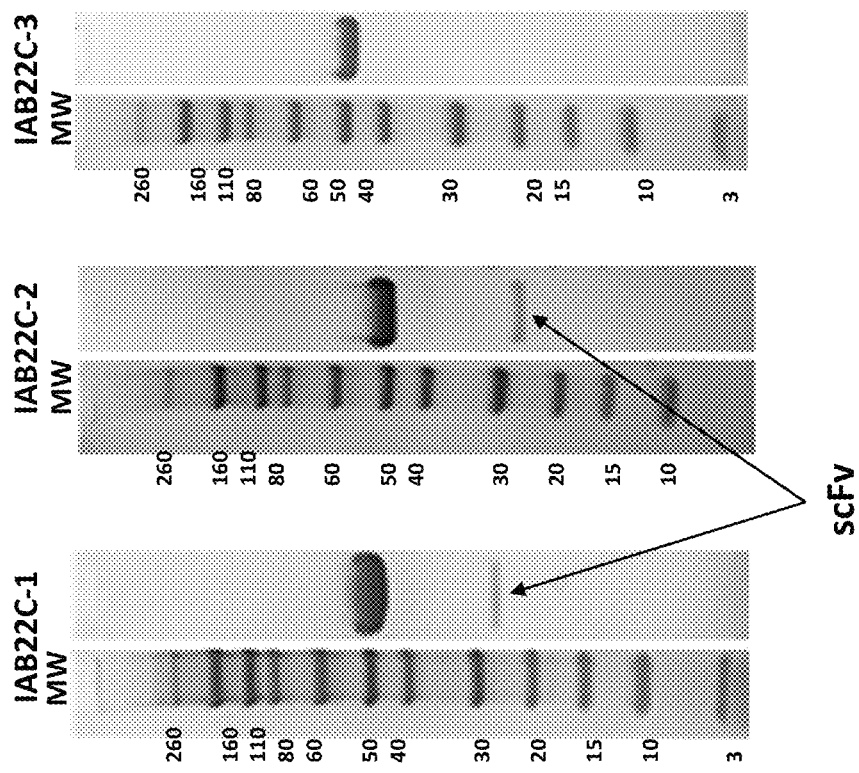
FIG. 8A depicts an SDS-PAGE gel that shows bands that correspond to both an intact Cys-diabody and a single chain fragment variable derived from the IAB22C-1 construct.
FIG. 8B depicts an SDS-PAGE gel that shows bands that correspond to both an intact Cys-diabody and a single chain fragment variable derived from the IAB22C-2 construct.
FIG. 8C depicts an SDS-PAGE gel that shows bands that correspond to an intact Cys-diabody from the IAB22C-3 construct with no detectable scFv.
Figures 12A, 12B, 12C:
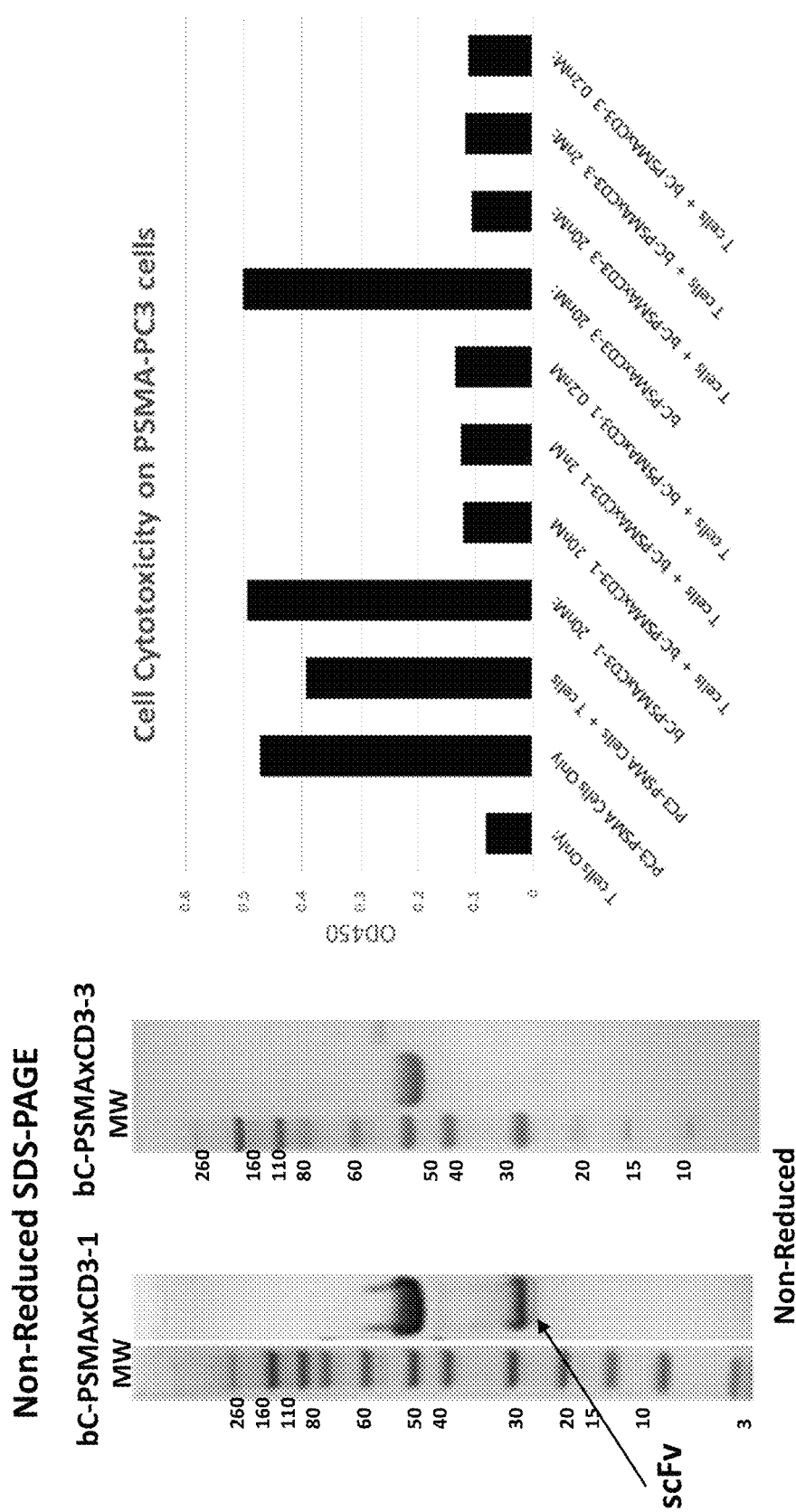
FIG. 12A depicts a SDS-PAGE gel that shows bands that correspond to an intact Cys-diabody and a single chain fragment variable derived from the bC-PSMAxCD3-1 construct.
FIG. 12B depicts a SDS-PAGE gel that shows bands that correspond to an intact Cys-diabody derived from the bC-PSMAxCD3-3 construct with no detectable scFv.
FIG. 12C depicts levels of cell cytotoxicity on PSMA-PC3 cells when treated with various constructs.
Figure 13:
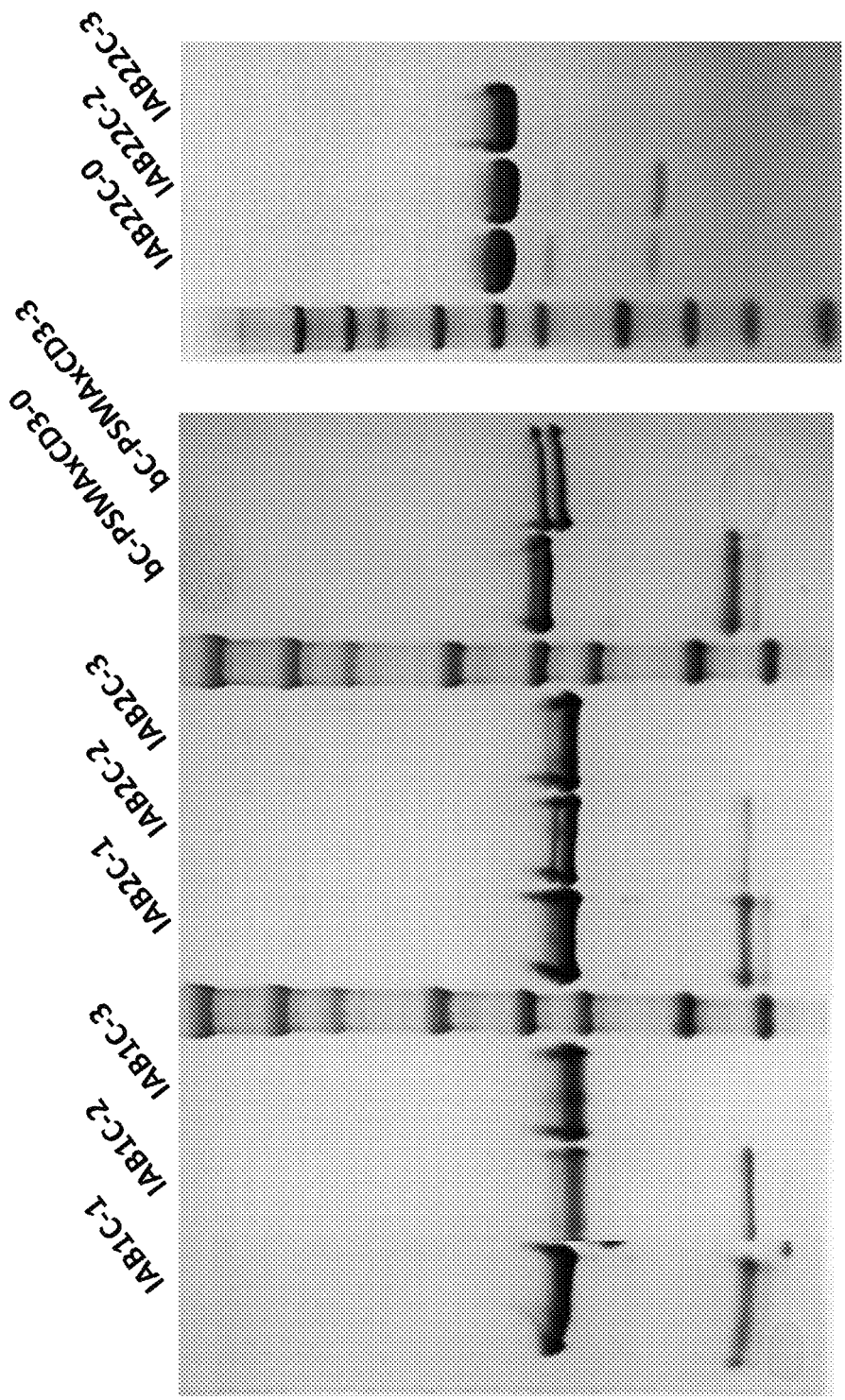
FIG. 13 depicts SDS-PAGE gels that summarize expression of intact Cys-diabodies and single chain fragment variables across various constructs.

As shown in FIG. 4A, the JAB1 Cys-diabody containing 1 CPPC (SEQ ID NO: 7) motif produces a heterogeneous composition in which a 25 kd band appears that represents the scFv. When 2 CPPC (SEQ ID NO: 7) motifs are present the intensity of this 25 kd band decreases as shown in FIG. 4B resulting in a more homogeneous composition. When 3 CPPC (SEQ ID NO: 7) motifs are present there is no 25 kd band as shown in FIG. 4C. Similar results are shown with (i) the IAB2C Cys-diabody (See FIGS. 6A, 6B, and 6C), (ii) the IAB22C Cys-diabody (See FIGS. 8A, 8B, and 8C), (iii) the IAB8C Cys-diabody (See FIGS. 10A, 10B, and 10C). In addition, FIGS. 12A and 12B show that the bispecific bC-PMSA construct that contains 1 CPPC (SEQ ID NO: 7) motif produces a 25 kd band that represents the scFv, whereas when 3 CPPC (SEQ ID NO: 7) motifs are added the scFv band disappears. FIG. 13 shows a summary of the various Cys-diabody variants revealing improved homogeneity (reduced expression of the scFv band) when CPPC (SEQ ID NO: 7) motifs are added to the constructs.

In summary, adding one PPC with two total Cys is not enough to maintain dimeric protein through purification and analysis. However, adding two PPC with a total of three Cys results in a very homogeneous protein with no monomer. Adding three PPC with a total of four Cys results in a very homogeneous protein with no monomer. Thus, SDS-PAGE analysis of Cys diabodies with different PPC motifs shows benefit of adding cysteine residues.

Example 4

FACS Analysis of the Constructs Shows that Adding CPPC (SEQ ID NO: 7) Motifs to the C-Terminus does not Impact Binding CPPC (SEQ ID NO: 7) motifs added to the C-terminus do not impact binding of IAB1C to PSCA expressed on SW780 cells. SW780 cells were cultured in Dulbecco's MEM and harvested by washing with sterile Dulbecco's phosphate buffer saline (without Calcium and Magnesium). The cells were detached with Accutase solution followed by centrifugation at 400 rpm for 5 minutes. The supernatant was removed and the cells were counted and re-suspended at a density of 1-2×10$^6$ cells/mL in the staining buffer (1% BSA in phosphate buffer saline, 0.09% sodium azide).

50,000-200,000 cells were placed into each well of a 96 well conical bottom plate in a volume of 100 ul. The respective protein samples were prepared at 2× the maximum concentration. 12 serial dilutions ranging from 100 nM-0.0006 nM were prepared by aliquoting 3× dilutions in 1% BSA in phosphate buffer saline, 0.09% sodium azide buffer. 100 uL of each of the diluted protein samples were combined with the cells and incubated at 4° C. for 30 minutes. The cells were centrifuged at 400 rpm for 5 minutes and the supernatant discarded. A working solution of 2 µg/mL Biotinylated protein was prepared according to the manufacturer's recommendation. 100 uL of this solution was added to the cells and the plate incubated at 4° C. for 30 minutes. Cells were centrifuged at 400 rpm for 5 minutes and the supernatant discarded.

A 1:500 dilution of Strep-avidin conjugated with Allophycocyanine was prepared according to the manufacturer's recommendation. 100 uL of this solution was added to the cells and the plate incubated at 4° C. for 30 minutes. Cells were centrifuged at 400 rpm for 5 minutes and the supernatant discarded. The cells were fixed by adding 100 ul of 4% paraformaldehyde and incubated at room temperature for 10 minutes.

Figure 5A:
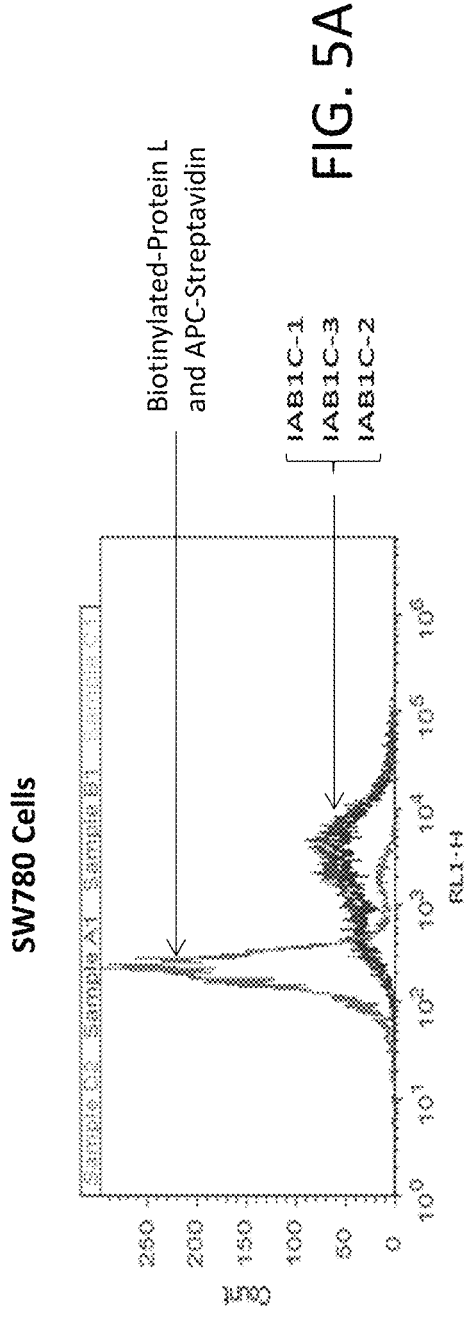
FIG. 5A depicts peaks showing binding of the IAB1C-1, IAB1C-2, and IAB1C-3 constructs to PSCA expressed on SW780 bladder cancer cells.
Figure 5B:
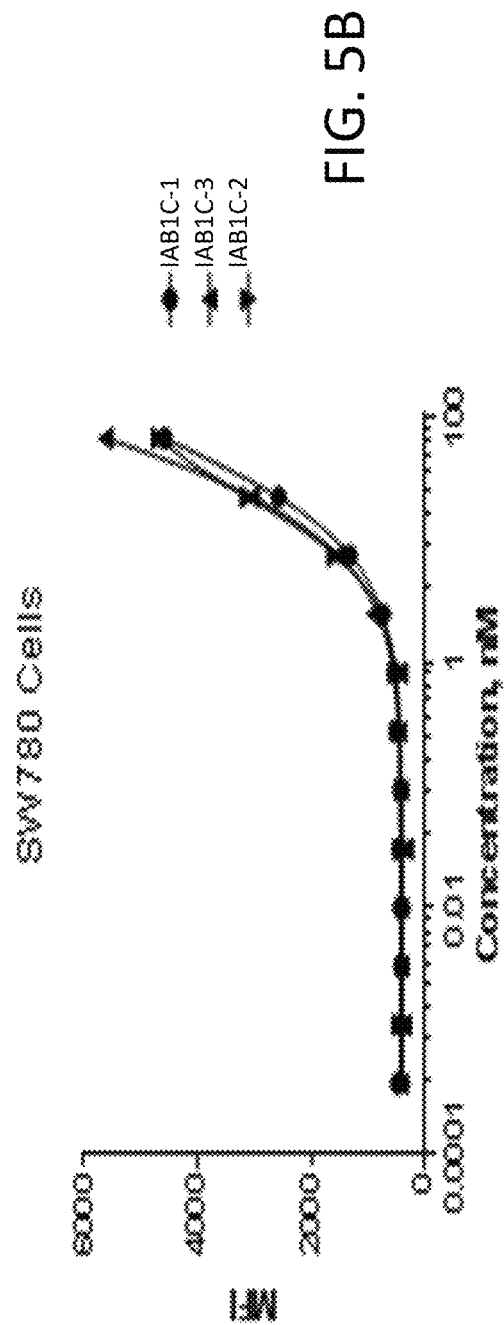
FIG. 5B depicts a graph that compares binding of the IAB1C-1, IAB1C-2, and IAB1C-3 constructs to PSCA at different concentrations of the constructs.

The cells were centrifuged at 400 rpm for 5 minutes, re-suspended in 200 uL of cell staining buffer (1% BSA in phosphate buffer saline, 0.09% sodium azide). Data were acquired on the Attune Acoustic Focusing Cytometer (Applied Biosystems, Foster City, Calif.) (FIG. 5A) and Mean Fluorescent Intensity (MFI) values were plotted against concentration for each sample (FIG. 5B). Best fit binding curves and IC$_{50}$ values were generated with four-parameter logistic nonlinear regression using GraphPad Prism version 6 for Windows (GraphPad Software, La Jolla, Calif.) and binding assessed on an Attune acoustic focusing cytometer (Applied Biosystems) (Table 4.1).

TABLE 4.1

|  | IAB1C-1 | IAB1C-2 | IAB1C-3 |
|---|---|---|---|
| EC$_{50}$ (nM) | 56.2 | 86.6 | 21.3 |

CPPC (SEQ ID NO: 7) motifs added to the C-terminus do not impact binding of IAB2C to PSMA expressed on PC3-PSMA cells. PC3-PSMA cells were cultured in Dulbecco's MEM and harvested by washing with sterile Dulbecco's phosphate buffer saline (without Calcium and Magnesium). The cells were detached with Accutase solution followed by centrifugation at 400 rpm for 5 minutes. The supernatant was removed and the cells were counted and re-suspended at a density of 1-2×10$^6$ cells/mL in the staining buffer (1% BSA in phosphate buffer saline, 0.09% sodium azide).

50,000-200,000 cells were placed into each well of a 96 well conical bottom plate in a volume of 100 ul. The respective protein samples were prepared at 2× the maximum concentration. 12 serial dilutions ranging from 100 nM-0.0006 nM were prepared by aliquoting 3× dilutions in 1% BSA in phosphate buffer saline, 0.09% sodium azide buffer. 100 uL of each of the diluted protein samples were combined with the cells and incubated at 4° C. for 30 minutes. The cells were centrifuged at 400 rpm for 5 minutes and the supernatant discarded. A working solution of 2 µg/mL Biotinylated protein was prepared according to the manufacturer's recommendation. 100 uL of this solution was added to the cells and the plate incubated at 4° C. for 30 minutes. Cells were centrifuged at 400 rpm for 5 minutes and the supernatant discarded.

A 1:500 dilution of Strep-avidin conjugated with Allophycocyanine was prepared according to the manufacturer's recommendation. 100 uL of this solution was added to the cells and the plate incubated at 4° C. for 30 minutes. Cells were centrifuged at 400 rpm for 5 minutes and the supernatant discarded. The cells were fixed by adding 100 ul of 4% paraformaldehyde and incubated at room temperature for 10 minutes.

The cells were centrifuged at 400 rpm for 5 minutes, re-suspended in 200 uL of cell staining buffer (1% BSA in phosphate buffer saline, 0.09% sodium azide). Data were acquired on the Attune Acoustic Focusing Cytometer (Applied Biosystems, Foster City, Calif.) (FIG. 7A) and Mean Fluorescent Intensity (MFI) values were plotted against concentration for each sample (FIG. 7B). Best fit binding curves and $IC_{50}$ values were generated with four-parameter logistic nonlinear regression using GraphPad Prism version 6 for Windows (GraphPad Software, La Jolla, Calif.) and binding assessed on an Attune acoustic focusing cytometer (Applied Biosystems) (Table 4.2).

TABLE 4.2

|  | IAB2C-1 | IAB2C-2 | IAB2C-3 |
| --- | --- | --- | --- |
| $EC_{50}$ (nM) | 4.4 | 7.5 | 5.3 |

CPPC (SEQ ID NO: 7) motifs added to the C-terminus does not impact binding of IAB22C to CD8 expressed on HPB-ALL cells. HPB-ALL cells were cultured in RPMI medium and harvested by centrifugation at 400 rpm for 5 minutes. The supernatant was removed and the cells were counted and re-suspended at a density of $1-2 \times 10^6$ cells/mL in the staining buffer (1% BSA in phosphate buffer saline, 0.09% sodium azide).

50,000-200,000 cells were placed into each well of a 96 well conical bottom plate in a volume of 100 ul. The respective protein samples were prepared at 2× the maximum concentration. 12 serial dilutions ranging from 100 nM-0.0006 nM were prepared by aliquoting 3× dilutions in 1% BSA in phosphate buffer saline, 0.09% sodium azide buffer. 100 uL of each of the diluted protein samples were combined with the cells and incubated at 4° C. for 30 minutes. The cells were centrifuged at 400 rpm for 5 minutes and the supernatant discarded. A working solution of 2 µg/mL Biotinylated protein was prepared according to the manufacturer's recommendation. 100 uL of this solution was added to the cells and the plate incubated at 4° C. for 30 minutes. Cells were centrifuged at 400 rpm for 5 minutes and the supernatant discarded.

A 1:500 dilution of Strep-avidin conjugated with Allophycocyanine was prepared according to the manufacturer's recommendation. 100 uL of this solution was added to the cells and the plate incubated at 4° C. for 30 minutes. Cells were centrifuged at 400 rpm for 5 minutes and the supernatant discarded. The cells were fixed by adding 100 ul of 4% paraformaldehyde and incubated at room temperature for 10 minutes.

The cells were centrifuged at 400 rpm for 5 minutes, re-suspended in 200 uL of cell staining buffer (1% BSA in phosphate buffer saline, 0.09% sodium azide). Data were acquired on the Attune Acoustic Focusing Cytometer (Applied Biosystems, Foster City, Calif.) (FIG. 9A) and Mean Fluorescent Intensity (MFI) values were plotted against concentration for each sample (FIG. 9B). Best fit binding curves and $IC_{50}$ values were generated with four-parameter logistic nonlinear regression using GraphPad Prism version 6 for Windows (GraphPad Software, La Jolla, Calif.). and binding assessed on an Attune acoustic focusing cytometer (Applied Biosystems) (Table 4.3).

TABLE 4.3

|  | IAB22C-1 | IAB22C-2 | IAB22C-3 |
| --- | --- | --- | --- |
| $EC_{50}$ (nM) | 0.08 | 0.15 | 0.13 |

CPPC (SEQ ID NO: 7) motifs added to the C-terminus do not impact binding of IAB8C to Her2/neu expressed on NCI-N87 cells. NCI-N87 cells were cultured in Dulbecco's MEM and harvested by washing with sterile Dulbecco's phosphate buffer saline (without Calcium and Magnesium). The cells were detached with Accutase solution followed by centrifugation at 400 rpm for 5 minutes. The supernatant was removed and the cells were counted and re-suspended at a density of $1-2 \times 10^6$ cells/mL in the staining buffer (1% BSA in phosphate buffer saline, 0.09% sodium azide).

50,000-200,000 cells were placed into each well of a 96 well conical bottom plate in a volume of 100 ul. The respective protein samples were prepared at 2× the maximum concentration. 12 serial dilutions ranging from 100 nM-0.0006 nM were prepared by aliquoting 3× dilutions in 1% BSA in phosphate buffer saline, 0.09% sodium azide buffer. 100 uL of each of the diluted protein samples were combined with the cells and incubated at 4° C. for 30 minutes. The cells were centrifuged at 400 rpm for 5 minutes and the supernatant discarded. A working solution of 2 µg/mL Biotinylated protein was prepared according to the manufacturer's recommendation. 100 uL of this solution was added to the cells and the plate incubated at 4° C. for 30 minutes. Cells were centrifuged at 400 rpm for 5 minutes and the supernatant discarded.

A 1:500 dilution of Strep-avidin conjugated with Allophycocyanine was prepared according to the manufacturer's recommendation. 100 uL of this solution was added to the cells and the plate incubated at 4° C. for 30 minutes. Cells were centrifuged at 400 rpm for 5 minutes and the supernatant discarded. The cells were fixed by adding 100 ul of 4% paraformaldehyde and incubated at room temperature for 10 minutes.

Figure 11A:
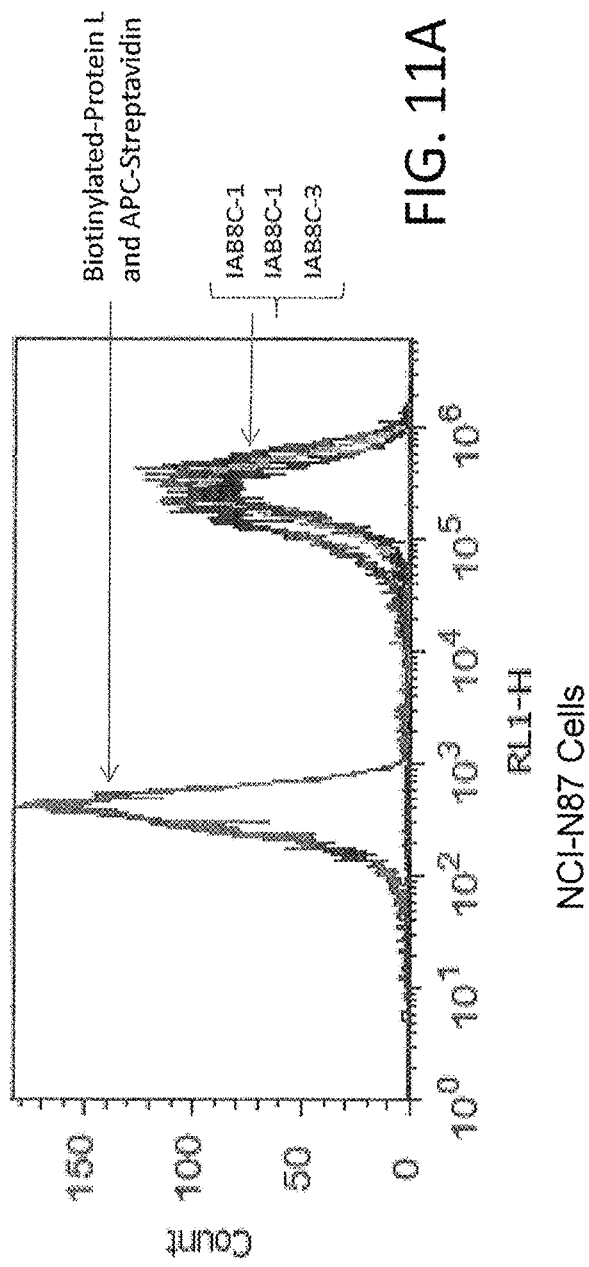
FIG. 11A depicts peaks showing binding of the IAB8C-1, IAB8C-3, and IAB8C-4 constructs to Her2/neu expressed on the surface of NCI-N87 gastric cancer cells.
Figure 11B:
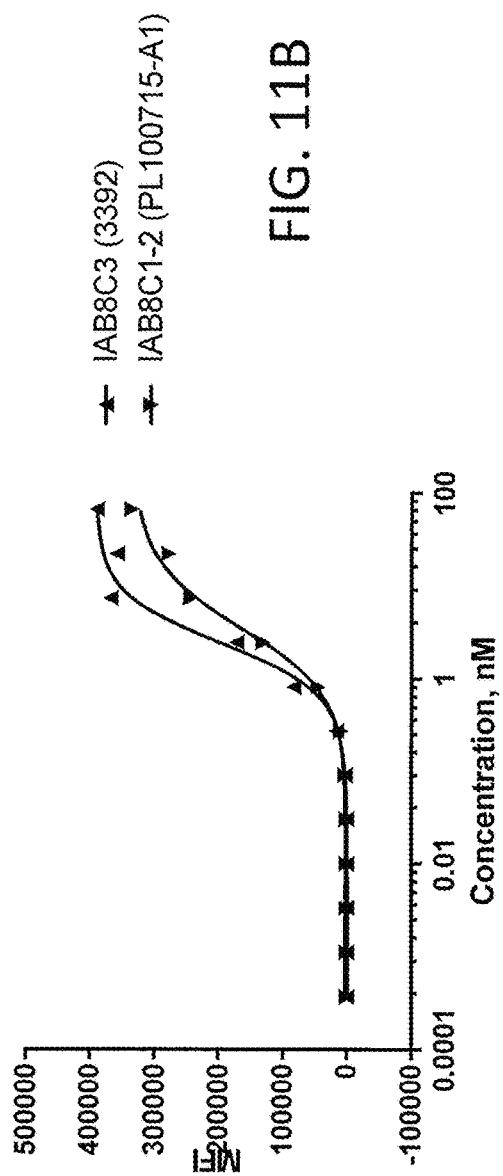
FIG. 11B depicts a graph that compares binding of the IAB2C-1, IAB2C-2, and IAB2C-3 constructs to Her2/neu at different concentrations of the constructs.

The cells were centrifuged at 400 rpm for 5 minutes, re-suspended in 200 uL of cell staining buffer (1% BSA in phosphate buffer saline, 0.09% sodium azide). Data were acquired on the Attune Acoustic Focusing Cytometer (Applied Biosystems, Foster City, Calif.) (FIG. 11A) and Mean Fluorescent Intensity (MFI) values were plotted against concentration for each sample (FIG. 11B). Best fit binding curves and $IC_{50}$ values were generated with four-parameter logistic nonlinear regression using GraphPad Prism version 6 for Windows (GraphPad Software, La Jolla, Calif.) and binding assessed on an Attune acoustic focusing cytometer (Applied Biosystems) (Table 4.4).

TABLE 4.4

|  | IAB8C-3 | IAB8C-1 |
| --- | --- | --- |
| $EC_{50}$ (nM) | 2.4 | 3.5 |

Example 5

Bispecific BC-PSMA×CD3 Cys-Diabodies Bind to CD3 on T Cells and PSMA on Tumor Cells to Mediate Target Specific Cytotoxicity The anti-tumor activity of the anti-CD3× anti-PSMA bispecific Cys-diabodies was tested in T cell mediated cytotoxic assays using PC3-PSMA transfected cells. Freshly prepared human PBMCs or T cells isolated using MACs beads were incubated in 96 well plates together with PC3-PSMA expressing tumor cells in the presence or absence of the indicated concentration of cys-diabody. After incubation for 48 hours to allow time for killing, the metabolic indicator, WST, was added to each well. Incubation was continued for approximately 3 hours at 37° C. The absorbance at 450 nM in each well was determined using a plate reader. The result shown in FIG. 12C demonstrate that all anti-CD3× anti-PSMA bispecific Cys-diabodies showed potent and specific killing of PC3-PSMA(+ve) cells at all doses tested when incubated with human T cells in vitro. However, incubation of the bispecific Cys-diabody with the target PC3-PSMA cells in the absence of T cells showed no cytotoxic activity. In addition, Incubation of PC3-PSMA cells in the presence of T cells without adding the bispecific Cys-Db had no activity. These results show bispecific diabodies with C terminal extension sequences can bring 2 different cell types in close contact to mediate killing of antigen expressing target cells.

Example 6

Intact Mass Spectrometry Analysis Confirms that Increasing the Number of Disulfide Bonds Reduces the Levels of SCFV The intact mass analyses were performed using LC-MS at the City of Hope Core Facility. Expressed Cys-Diabody proteins were desalted and separated using Waters nanoAcquity UPLC equipped with a C4 nanotile column (150 µm ID×50 mm, Waters) operated at 3 µl/min, with 0.1% formic acid in water and 0.1% formic acid in acetonitrile as mobile phases. The HPLC was coupled to Waters Synapt G2 HDMS fitted with a Trizaic nanoESI source. The samples were analyzed for intact mass and the amount of the half molecule by LC/MS. Representative deconvoluted mass spectra are shown in FIGS. 14A, 14B, 15A, 15B, 15C, 16A, 16B, 16C, 17A, and 17B.

Figures 14C, 14D:
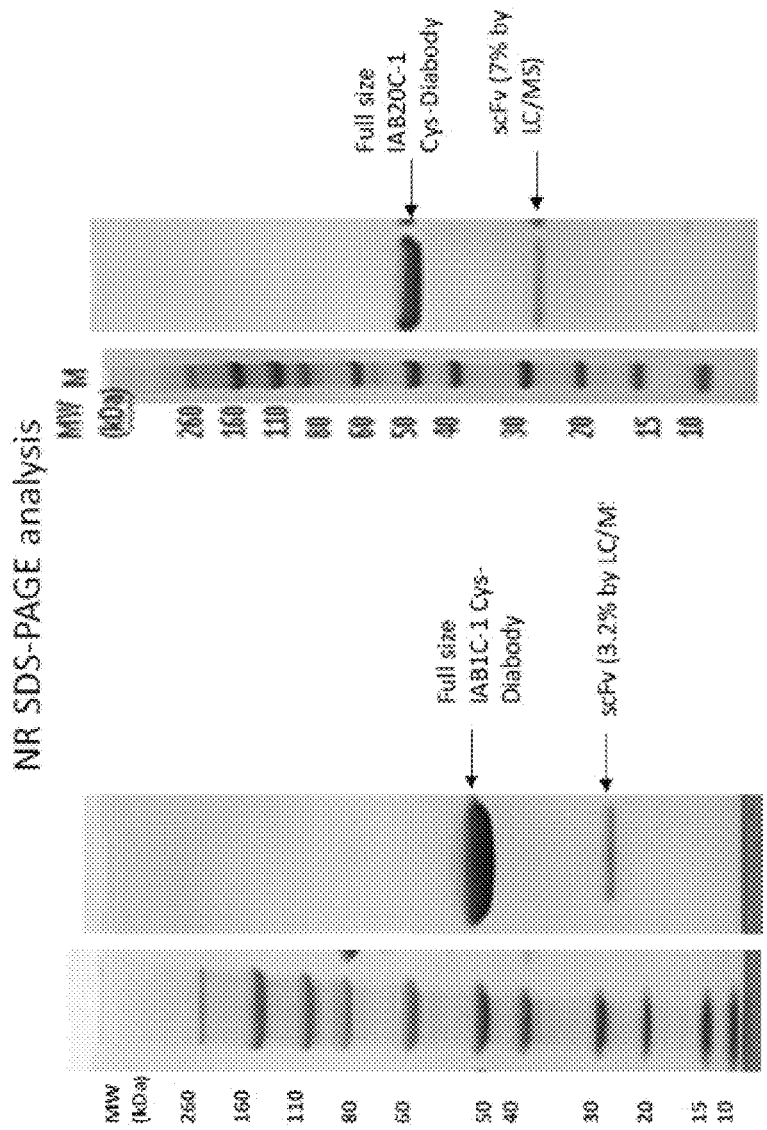
FIG. 14C depicts an SDS-PAGE gel that shows bands that correspond to the full size diabody of the IAB1C-1 construct.
FIG. 14D depicts and SDS-PAGE get that shows bands that correspond to the full size diabody of the IAB20C-1 construct.
Figures 16A, 16B, 16C:
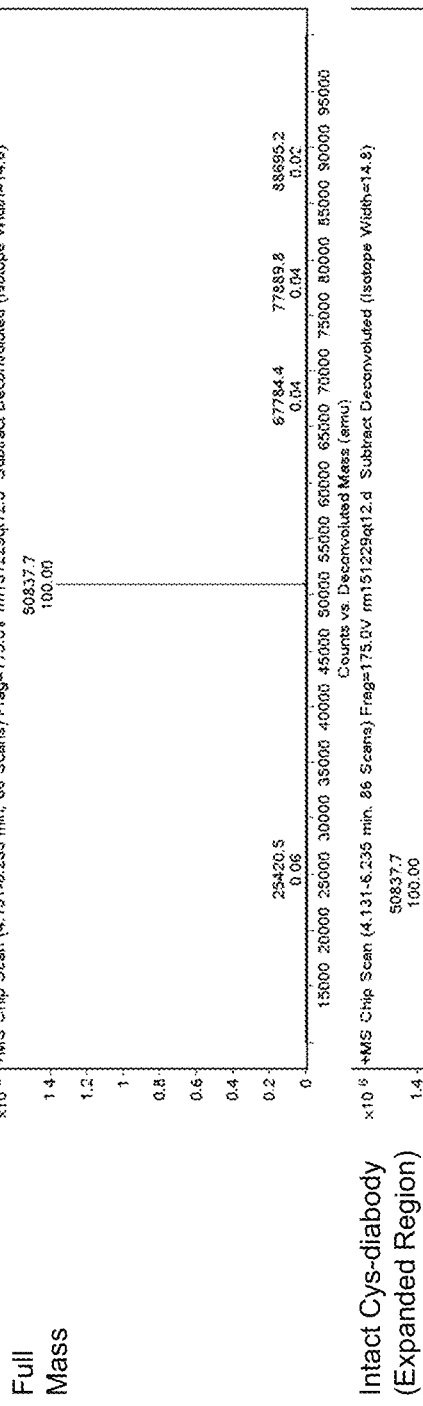
FIG. 16A depicts Mass Spectrometry analysis of the IAB22C-3 intact diabody.
FIG. 16B depicts Mass Spectrometry analysis of the relevant expanded region of the IAB22C-3 intact diabody.
FIG. 16C depicts Mass Spectrometry analysis of the IAB22C-3 single chain fragment variable.
Figure 17A:
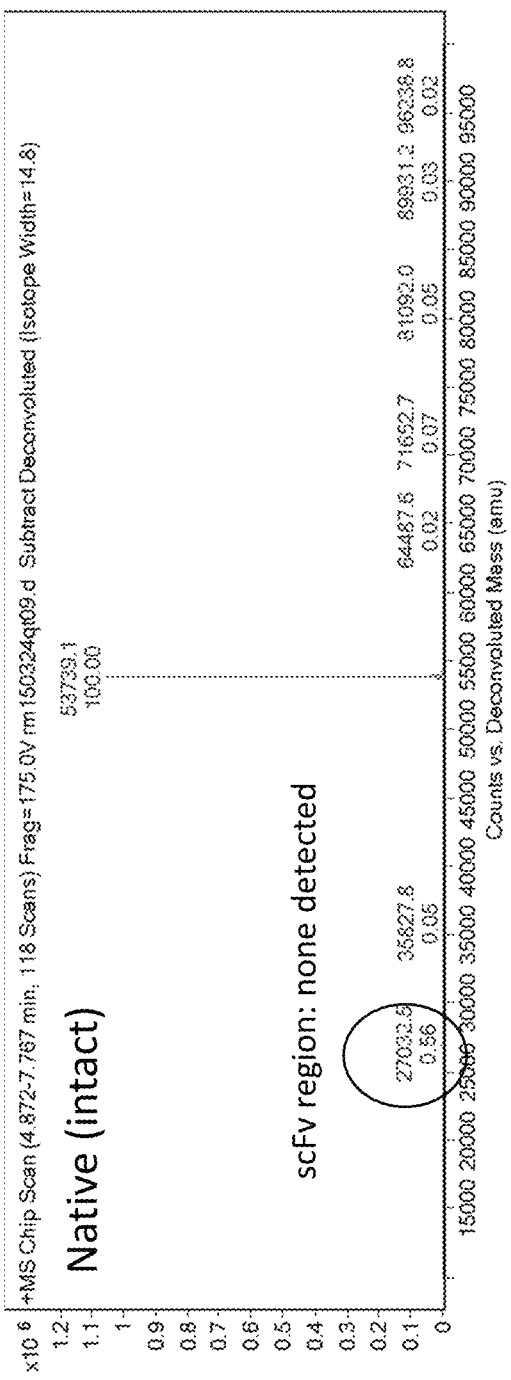
FIG. 17A depicts Mass Spectrometry of the intact bC-5T4×CD3 diabody.
Figure 17B:
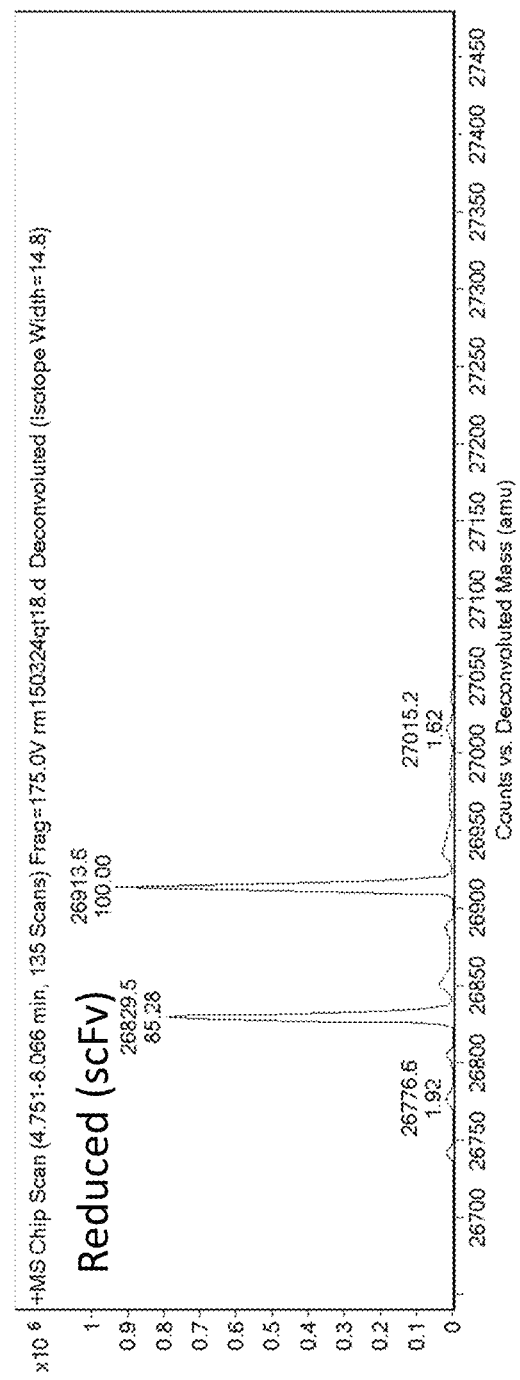
FIG. 17B depicts Mass Spectrometry of the reduced form of the bC-5T4×CD3 diabody showing 2 distinct protein peaks.

The IAb1C-1 and IAB20C diabodies that are linked by a single disulfide bond show high amounts of scFv or its Glutathione adduct when analyzed by mass spectrometry (FIGS. 14A and 14B). This result is confirmed when proteins are resolved on a non-reducing SDS-PAGE gel (FIGS. 14C and 14D). The IAB2C-3 and IAB22C-3 diabodies that are linked by three disulfides show only trace amounts of scFv (FIGS. 15A, 15B, 15C, 16A, 16B, and 16C). Analysis of bC-5T4×CD3 bispecific Cys diabody shows correct assembly of the bispecific diabody and undetectable levels of scFv (FIG. 17A). Efficient assembly of the bispecific Cys diabody with a 1:1 ratio of both chains in which only one molecule of expected molecular weight is produced, which is broken down into 2 scFV arms corresponding to the molecular mass of 5T4 and CD3 scFv's respectively (FIG. 17B).

Example 7

Figure 18:
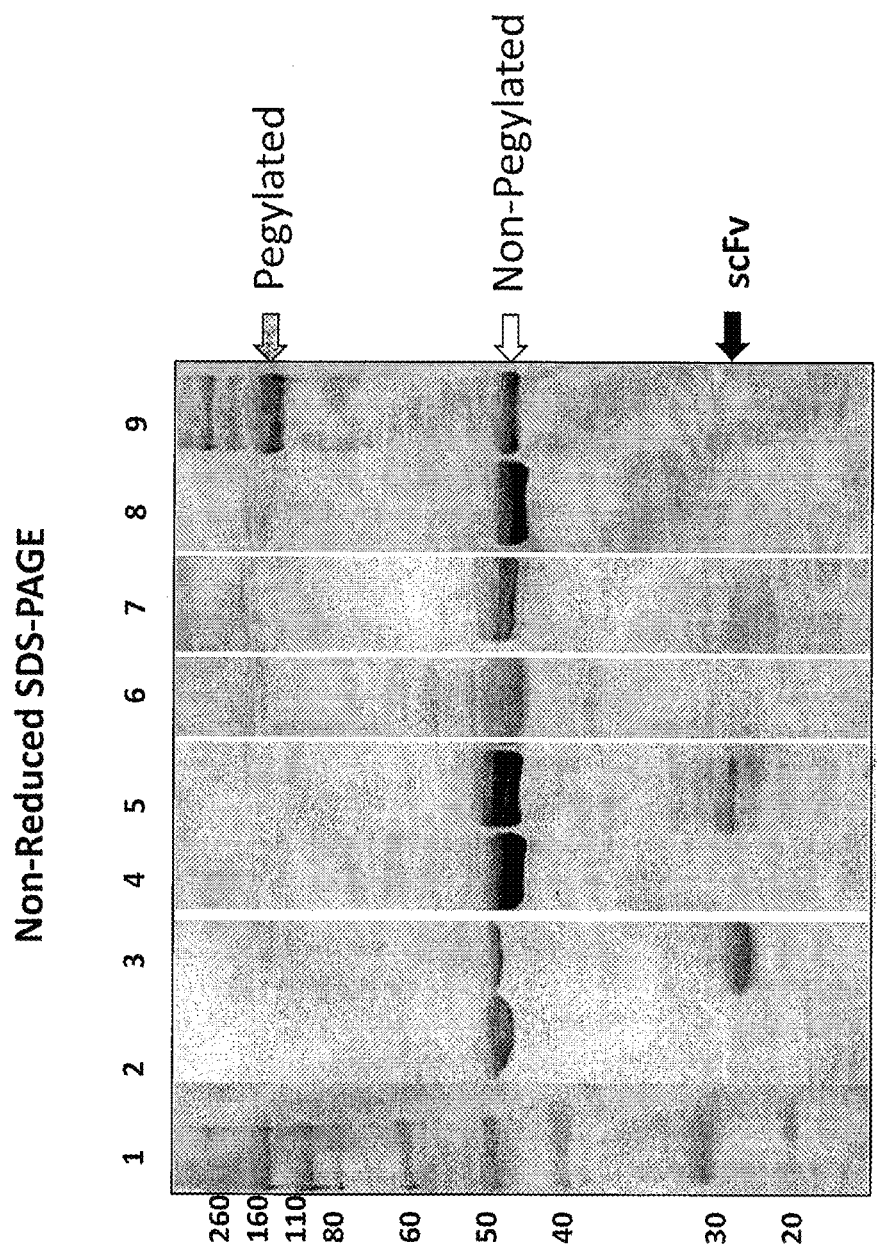
FIG. 18 depicts a SDS-PAGE gel showing bands that correspond to intact Cys-diabodies and single chain fragment variables after site-specific conjugation of single and multi-IAB8C Cys diabody proteins.

SCFV Formation after Site-Specific Conjugation of Single and Multi-IAB8C Cys Diabody Proteins IAB8C Cys-diabody proteins were gently reduced using limiting TCEP and free thiol handles were quantified using the Ellman's assay, to yield approx. 2 free thiols. The resulting products were reacted with maleimido-Df chelate reagent (B-772, Macrocyclics, Dallas, Tex.) or Maleimido-PEG10k (CreativePEGworks), purified and the amount of scFv was assessed by densitometry using non-reducing SDS-PAGE. The results are summarized in table 8.1 and FIG. 18. In FIG. 18, Molecular weight markers are shown in lane 1. Bottom arrow: scFv; middle arrow: intact Cys-Db; top arrow: major PEGylated product with 2 equivalents of PEG10k. In summary, only small amounts of scFv are detectable after reduction and conjugation of Deferoxamine (DO to cys residues in IAB8C-4 compared to conjugation on a single Cys in IAB8C-1 (FIG. 18 and Table 7.1).

TABLE 7.1

| Construct | Lane | Disulfide Bonds | Df or PEG 10k per Protein | scFv (%) |
|---|---|---|---|---|
| IAB8C-1 | 2 | 1-Cys | n/a | None |
| Df-IABC-1 | 3 | 1-Cys | 1.7 | 75% |
| IAB8C-3 | 4 | 3-Cys | n/a | None |
| Df-IAB8C-3 | 5 | 3-Cys | 1.9 | Approx. 8% |
| IAB8C-4 | 6 | 4-Cys | n/a | None |
| Df-IAB8C-4 | 7 | 4-Cys | 2 | Approx. 4% |
| IAB8C-4 | 8 | 4-Cys | n/a | None |
| PEG10k-IAB8C-4 | 9 | 4-Cys | 2 | None |

Example 8

In Vivo Evaluation of Single and Multi-Cys IAB8C Diabodies Following Conjugation of Df to Cys and Pegylation on Lysine The 10 and 20 kDa PEGylated Cys-Diabodies IAB8C-1 and IAB8C-4 were generated by conjugating to cys residues. Respective proteins were reduced with TCEP, reacted with maleimido-PEG and the resulting products purified by SE HPLC from the excess PEG and non-pegylated Cys-Diabody using Acquity BEH 200 column (4.6 mm×150 mm, Waters). The purified constructs were concentrated and buffer exchanged into borate buffer pH8.5. Deferoxamine (Df) was subsequently conjugated to lysine residues (isothiocyanate-Df, Macrocyclics). All conjugated diabodies were formulated in Hepes saline buffer pH7.0. The non-pegylated Cys-diabody, $^{89}$Zr-Df-IAB8C-1 was conjugated to cysteine residues using Maleimido-Df obtained from Macrocyclics. Table 8.1 summarizes this study design.

TABLE 8.1

| Construct | Disulfide Bonds | Df per Protein | PEG per protein |
|---|---|---|---|
| $^{89}$Zr-Df-IAB8C-1 | 1-Cys | 1.8 | None |
| $^{89}$Zr-Df-IAB8C-1-10kPEG | 1-Cys | 1.5 | 2.0 |
| $^{89}$Zr-Df-IAB8C-4-10kPEG | 4-Cys | 1.9 | ~3.0 |
| $^{89}$Zr-Df-IAB8C-4-20kPEG | 4-Cys | 2.4 | ~3.0 |

Figure 20:
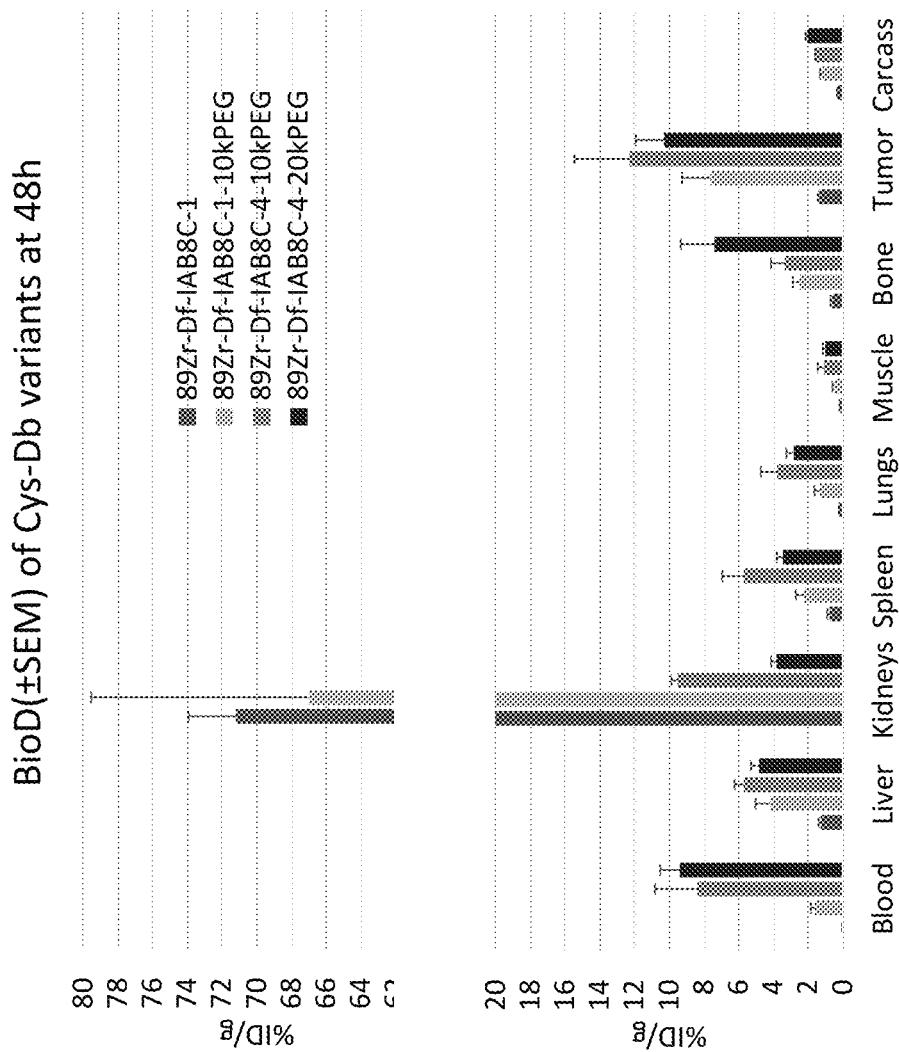
FIG. 20 depicts a graph showing biodistribution across various tissues of $^{89}$Zr-DF-IABDBC-1, $^{89}$Zr-DF-IABDBC-1-10kPEG, $^{89}$Zr-DF-IABDBC-4-10kPEG, $^{89}$Zr-DF-IABDBC-4-20kPEG 48 hours after injection.
Figure 21:
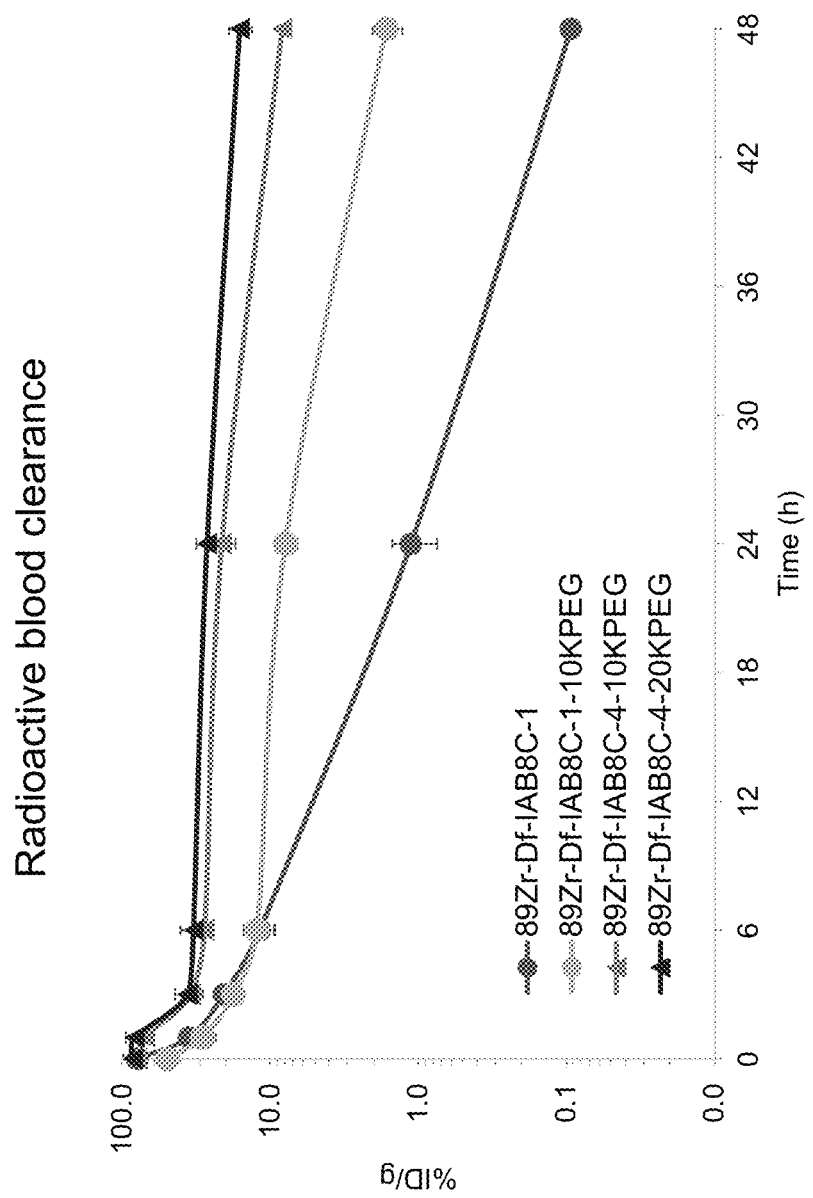
FIG. 21 depicts a graph showing blood clearance of $^{89}$Zr-DF-IABDBC-1, $^{89}$Zr-DF-IABDBC-1-10kPEG, $^{89}$Zr-DF-IABDBC-4-10kPEG, $^{89}$Zr-DF-IABDBC-4-20kPEG at different time points after injection.

The in vivo preclinical evaluation of Df-conjugated Cys-Db variants were conducted using female NOD SCID mice bearing human MCF7/HER2 breast cancer xenografts. To establish xenografts, mice were primed with 17β-estradiol in a biodegradable carrier-binder (1.7 mg estradiol/pellet) introduced subcutaneously (s.c.). After 6 days, 10 million MCF7/HER2 cells (mixed with 1:1 matrigel) in 300 µL volume were implanted subcutaneously into the right flank. Tumors were allowed to grow for three weeks before being imaged. For PET imaging, Cys-Db variants were conjugated to desferrioxamine (DO and radiolabeled with the positron emitting radionuclide, Zirconium-89 ($^{89}$Zr). Mice were divided into four groups of 3 mice each and ~10 µg of $^{89}$Zr-Df-IAB8C-1, $^{89}$Zr-Df-IAB8C-1-10kPEG, $^{89}$Zr-Df-IAB8C-4-10kPEG or $^{89}$Zr-Df-IAB8C-1-20kPEG were administered intravenously. Mice were imaged at 4 h, 24 h and 48 h, by PET for 10 minutes followed by a 2 minute CT scan for anatomical reference (FIGS. 19A, 19B, and 19C). All mice were sacrificed after the last scan at 48 hours and tumor, blood and organs of interest were harvested, weighted and counted in a gamma counter to determine the injected dose per gram (% ID/g) (FIG. 20 and Table 8.2). Blood samples were also collected throughout the imaging study and uptakes were plotted against time to determine the radioactive PK of the Cys-Db variants (FIG. 21).

TABLE 8.2

|  | $^{89}$Zr-Df-IAB8C-1 % ID/g(SEM) | $^{89}$Zr-Df-IAB8C-1-10kPEG % ID/g(SEM) | $^{89}$Zr-Df-IAB8C-4-10kPEG % ID/g(SEM) | $^{89}$Zr-Df-IAB8C-4-20kPEG SEM |
|---|---|---|---|---|
| Blood | 0.04(0.01) | 1.61(0.23) | 8.37(2.46) | 9.40(1.13) |
| Liver | 1.27(0.13) | 4.19(0.84) | 5.70(0.55) | 4.83(0.48) |
| Kidneys | 71.20(2.74) | 66.99(12.55) | 9.52(0.37) | 3.82(0.32) |
| Spleen | 0.78(0.12) | 2.26(0.45) | 5.70(1.25) | 3.45(0.35) |
| Lungs | 0.23(0.01) | 1.33(0.32) | 3.78(0.95) | 2.84(0.42) |
| Muscle | 0.15(0.04) | 0.51(0.10) | 1.10(0.35) | 1.02(0.14) |
| Bone | 0.61(0.09) | 2.48(0.39) | 3.34(0.80) | 7.41(1.95) |
| Tumor | 1.37(0.07) | 7.63(1.65) | 12.31(3.16) | 10.30(1.65) |
| Carcass | 0.29(0.04) | 1.16(0.16) | 1.58(0.02) | 2.04(0.11) |

Results show that $^{89}$Zr-Df-IAB8C-4-10kPEG10 and $^{89}$Zr-Df-IAB8C-4-10kPEG10 show higher tumor uptake. $^{89}$Zr-Df-IAB8C-4-10kPEG10 and $^{89}$Zr-Df-IAB8C-4-10kPEG10 are not cleared primarily through the kidney due to the larger overall size of the proteins. Clearance of $^{89}$Zr-Df-IAB8C-1-10kPEG10 via the kidneys suggests that a diabody with a single cys bond dissociates into scFvs in vivo allowing for renal clearance similar to that observed for $^{89}$Zr-Df-IAB8C-1. $^{89}$Zr-Df-IAB8C-4-10kPEG10 and $^{89}$Zr-Df-IAB8C-4-10kPEG10 show longer circulating half-lives as expected from PEGylated proteins. $^{89}$Zr-Df-IAB8C-1-10kPEG10 has an intermediate blood clearance. $^{89}$Zr-Df-IAB8C-1 clears very rapidly from the blood confirming results with other diabodies containing a single disulfide bond.

Example 9

A subject with a PSCA related disorder is identified. A diabody IAB1C (IAB1C-1, JAB1C-2 and/or in the alternative JAB1C-3) is used to deliver a cytotoxic payload to a PSCA expressing cell to kill the PSCA expressing cell. The subject's health improves with the removal of at least some of the PSCA expressing cells.

Example 10

A subject with a PSMA related disorder is identified. A diabody IAB2C (IAB2C-1, IAB2C-2 and/or in the alternative IAB2C-3) is used to deliver a cytotoxic payload to a PSMA expressing cell to kill the PSMA expressing cell. The subject's health improves with the removal of at least some of the PSMA expressing cells.

Example 11

A subject with a CD8 related disorder is identified. A diabody IAB22C (IAB22C-1, IAB22C-2 and/or in the alternative IAB22C-3) is used to deliver a cytotoxic payload to a CD8 expressing cell to kill the CD8 expressing cell. The subject's health improves with the removal of at least some of the CD8 expressing cells.

Example 12

A subject with a Her2/neu related disorder is identified. A diabody IAB8C (IAB8C-1, IAB8C-2 and/or in the alternative IAB8C-3) is used to deliver a cytotoxic payload to a Her2/neu expressing cell to kill the Her2/neu expressing cell. The subject's health improves with the removal of at least some of the Her2/neu expressing cells.

Example 13

A subject with a PSMAxCD3 related disorder is identified. A diabody bC-PSMAxCD3-1 bC-CD3xPSMA-1 or bC-PSMAxCD3-3bC-CD3xPSMA-3 is used to deliver a cytotoxic payload to a PSMAxCD3 expressing cell to kill the PSMAxCD3 expressing cell. The subject's health improves with the removal of at least some of the PSMAxCD3 expressing cells.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. A diabody comprising:
   a heavy chain variable domain;
   a light chain variable domain;
   a linker; and
   an extension sequence, wherein the extension sequence is selected from the group consisting of:

EPKSX$_{n5}$DKTHTCX$_{n1}$X$_{n2}$CX$_{n3}$X$_{n4}$C, (SEQ ID NO: 1)

ERKX$_{n5}$CX$_{n1}$X$_{n2}$CX$_{n3}$X$_{n4}$C, (SEQ ID NO: 2)

ELKTPLGDTTHTCX$_{n1}$X$_{n2}$CX$_{n3}$X$_{n4}$C, (SEQ ID NO: 3)

ESKYGPPCX$_{n1}$X$_{n2}$CX$_{n3}$X$_{n4}$C, (SEQ ID NO: 4)

CPPCPPC, (SEQ ID NO: 5)
   and

GGC(PPC)$_n$, (SEQ ID NO: 11)

wherein n is 2, 3, 4, 5, 6, 7, 8, or 9, and wherein X$_{n1}$, X$_{n2}$, X$_{n3}$, X$_{n4}$, and X$_{n5}$ can be any amino acid, wherein the extension sequence connects either a C-terminus of the heavy chain variable domain to a C-terminus of a different heavy chain variable domain of the diabody, or a C-terminus of the light chain variable domain to a C-terminus of a different light chain variable domain of the diabody, through one or more disulfide bonds.

2. An extension sequence configured for use within an antigen binding construct, wherein the extension sequence is selected from the group consisting of:

EPKSX$_{n5}$DKTHTC$_{n1}$X$_{n2}$CX$_{n3}$X$_{n4}$C, (SEQ ID NO: 1)

ERKX$_{n5}$CX$_{n1}$X$_{n2}$CX$_{n3}$X$_{n4}$C, (SEQ ID NO: 2)

ELKTPLGDTTHTCX$_{n1}$X$_{n2}$CX$_{n3}$X$_{n4}$C, (SEQ ID NO: 3)

ESKYGPPCX$_{n1}$X$_{n2}$CX$_{n3}$X$_{n4}$C, (SEQ ID NO: 4)

```
CPPCPPC,                                    (SEQ ID NO: 5)
and

GGC(PPC)ₙ                                   (SEQ ID NO: 11)
``` wherein n is 2, 3, 4, 5, 6, 7, 8, or 9, and
wherein $X_{n1}$, $X_{n2}$, $X_{n3}$, $X_{n4}$, and $X_{n5}$ can be any amino acid,
wherein the extension sequence is located at or within 10 amino acids from the C-terminus of a polypeptide chain of an antigen binding construct, wherein the polypeptide chain comprises either (i) a heavy chain variable domain; or (ii) a heavy chain variable domain and a light chain variable domain, wherein the extension sequence covalently connects the polypeptide chain with a different polypeptide chain of the antigen binding construct through one or more disulfide bonds.

3. The extension sequence of claim 2, wherein the extension sequence is located within an antibody.

4. The extension sequence of claim 3, wherein the antibody is a mono-specific antibody.

5. The extension sequence of claim 3, wherein the antibody is a bi-specific antibody.

6. The extension sequence of claim 2, wherein the extension sequence is located within an antibody fragment.

7. The extension sequence of claim 2, wherein the extension sequence is covalently attached to a detectable marker or a therapeutic agent.

8. The extension sequence of claim 2, further comprising a detectable marker.

9. The extension sequence of claim 8, wherein the detectable marker is a radionuclide.

10. The extension sequence of claim 9, wherein the radionuclide is selected from the group consisting of $^{90}$Y, $^{177}$Lu, and $^{227}$Ac.

11. The extension sequence of claim 5, wherein the bi-specific antibody is assembled in a 1:1 ratio.

12. A pharmaceutical composition comprising the extension sequence of claim 2.

13. A pharmaceutical composition comprising the diabody of claim 1.

14. A diabody comprising two chains, comprising:
a first chain comprising:
  a first heavy chain variable domain;
  a first light chain variable domain;
  a first linker that connects the first heavy chain variable domain and the first light chain variable domains; and
  a first extension sequence; and
a second chain comprising:
  a second heavy chain variable domain;
  a second light chain variable domain;
  a second linker that connects the second heavy and second light chain variable domains; and
  a second extension sequence,
  wherein the first extension sequence and the second extension sequence are covalently connected to one another, and connect either a) the first heavy chain variable domain to the second heavy chain variable domain, or b) the first light chain variable domain to the second light chain variable domain, through one or more disulfide bonds, wherein the first extension sequence and the second extension sequence are selected from the group consisting of:

```
EPKSX_n5DKTHTCX_n1X_n2CX_n3X_n4C,           (SEQ ID NO: 1)

ERKX_n5CX_n1X_n2CX_n3X_n4C,                 (SEQ ID NO: 2)

ELKTPLGDTTHTCX_n1X_n2CX_n3X_n4C,            (SEQ ID NO: 3)

ESKYGPPCX_n1X_n2CX_n3X_n4C,                 (SEQ ID NO: 4)
and

CPPCPPC,                                    (SEQ ID NO: 5)
and

GGC(PPC)_n,                                 (SEQ ID NO: 11)
``` wherein n is 2, 3, 4, 5, 6, 7, 8, or 9, and
wherein $X_{n1}$, $X_{n2}$, $X_{n3}$, $X_{n4}$, and $X_{n5}$ can be any amino acid.

15. The diabody of claim 1, wherein one or more of $X_{n1}$, $X_{n2}$, $X_{n3}$, $X_{n4}$ is a proline.

16. The extension sequence of claim 2, wherein one or more of $X_{n1}$, $X_{n2}$, $X_{n3}$, $X_{n4}$ is a proline.

17. The diabody of claim 14, wherein one or more of $X_{n1}$, $X_{n2}$, $X_{n3}$, $X_{n4}$ is a proline.

18. The diabody of claim 14, wherein the extension sequence connects either a C-terminus of the first heavy chain variable domain to a C-terminus of the second heavy chain variable domain, or a C-terminus of the first light chain variable domain to a C-terminus of the second light chain variable domain.

19. The extension sequence of claim 2, wherein the antigen binding construct is a diabody.

20. The extension sequence of claim 2, wherein the polypeptide chain comprises a linker.

21. The extension sequence of claim 20, wherein the polypeptide chain comprises the heavy chain variable domain and the light chain variable domain, and the linker connects the heavy chain variable domain to the light chain variable domain.

22. The diabody of claim 1, wherein the extension sequence is covalently attached to a detectable marker or a therapeutic agent.

23. The diabody of claim 22, wherein the detectable marker is a radionuclide.

24. The diabody of claim 23, wherein the radionuclide is selected from the group consisting of $^{90}$Y, $^{177}$Lu, and $^{227}$Ac.

25. The diabody of claim 14, wherein the first chain and the second chain recognize different epitopes.

* * * * *

SEQUENCE LISTING

<160> NUMBER OF SEQ ID NOS: 163

<210> SEQ ID NO 1
<211> LENGTH: 17

```
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 15, 16
<223> OTHER INFORMATION: Xaa can be any amino acid

<400> SEQUENCE: 1

Glu Pro Lys Ser Xaa Asp Lys Thr His Thr Cys Xaa Xaa Cys Xaa Xaa
1               5                   10                  15

Cys

<210> SEQ ID NO 2
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 9, 10
<223> OTHER INFORMATION: Xaa can be any amino acid

<400> SEQUENCE: 2

Glu Arg Lys Xaa Cys Xaa Xaa Cys Xaa Xaa Cys
1               5                   10

<210> SEQ ID NO 3
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 15, 17, 18
<223> OTHER INFORMATION: Xaa can be any amino acid

<400> SEQUENCE: 3

Glu Leu Lys Thr Pro Leu Gly Asp Thr Thr His Thr Cys Xaa Xaa Cys
1               5                   10                  15

Xaa Xaa Cys

<210> SEQ ID NO 4
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10, 12, 13
<223> OTHER INFORMATION: Xaa can be any amino acid

<400> SEQUENCE: 4

Glu Ser Lys Tyr Gly Pro Pro Cys Xaa Xaa Cys Xaa Xaa Cys
1               5                   10

<210> SEQ ID NO 5
<211> LENGTH: 7
<212> TYPE: PRT
<213> ORGANISM: Artificial
<220> FEATURE:
<223> OTHER INFORMATION: Synthetic

<400> SEQUENCE: 5
```

Cys Pro Pro Cys Pro Pro Cys
1               5

<210> SEQ ID NO 6
<211> LENGTH: 10
<212> TYPE: PRT
<213> ORGANISM: Artificial
<220> FEATURE:
<223> OTHER INFORMATION: Synthetic

<400> SEQUENCE: 6

Cys Pro Pro Cys Pro Pro Cys Pro Pro Cys
1               5                   10

<210> SEQ ID NO 7
<211> LENGTH: 4
<212> TYPE: PRT
<213> ORGANISM: Artificial
<220> FEATURE:
<223> OTHER INFORMATION: Synthetic

<400> SEQUENCE: 7

Cys Pro Pro Cys
1

<210> SEQ ID NO 8
<211> LENGTH: 13
<212> TYPE: PRT
<213> ORGANISM: Artificial
<220> FEATURE:
<223> OTHER INFORMATION: Synthetic

<400> SEQUENCE: 8

Cys Pro Pro Cys Pro Pro Cys Pro Pro Cys Pro Pro Cys
1               5                   10

<210> SEQ ID NO 9
<211> LENGTH: 16
<212> TYPE: PRT
<213> ORGANISM: Artificial
<220> FEATURE:
<223> OTHER INFORMATION: Synthetic

<400> SEQUENCE: 9

Cys Pro Pro Cys Pro Pro Cys Pro Pro Cys Pro Pro Cys Pro Pro Cys
1               5                   10                  15

<210> SEQ ID NO 10
<211> LENGTH: 19
<212> TYPE: PRT
<213> ORGANISM: Artificial
<220> FEATURE:
<223> OTHER INFORMATION: Synthetic

<400> SEQUENCE: 10

Cys Pro Pro Cys Pro Pro Cys Pro Pro Cys Pro Pro Cys Pro Pro Cys
1               5                   10                  15

Pro Pro Cys

<210> SEQ ID NO 11
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: REPEAT
<222> LOCATION: 4..6
<223> OTHER INFORMATION: ProProCys can be present 1, 2, 3, 4, 5, 6, 7, 8, or 9 times

<400> SEQUENCE: 11

Gly Gly Cys Pro Pro Cys
1               5

<210> SEQ ID NO 12
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9
<223> OTHER INFORMATION: Xaa can be any amino acid

<400> SEQUENCE: 12

Cys Xaa Xaa Cys Xaa Xaa Cys Xaa Xaa Cys
1               5                   10

<210> SEQ ID NO 13
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Xaa can be any amino acid

<400> SEQUENCE: 13

Cys Xaa Xaa Cys Xaa Xaa Cys Xaa Xaa Cys Xaa Xaa Cys
1               5                   10

<210> SEQ ID NO 14
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Xaa can be any amino acid

<400> SEQUENCE: 14

Cys Xaa Xaa Cys Xaa Xaa Cys Xaa Xaa Cys Xaa Xaa Cys Xaa Xaa Asn
1               5                   10                  15

Cys

<210> SEQ ID NO 15
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Xaa can be any amino acid

<400> SEQUENCE: 15

Cys Xaa Xaa Cys Xaa Xaa Cys Xaa Xaa Cys Xaa Xaa Cys Xaa Xaa Cys
1               5                   10                  15

Xaa Xaa Cys

```
<210> SEQ ID NO 16
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6
<223> OTHER INFORMATION: Xaa can be any amino acid

<400> SEQUENCE: 16
```

Cys Xaa Xaa Cys Xaa Xaa Cys
1               5

```
<210> SEQ ID NO 17
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 5
<223> OTHER INFORMATION: Xaa can be any amino acid
<220> FEATURE:
<221> NAME/KEY: VARIANT
<222> LOCATION: 4..6
<223> OTHER INFORMATION: XaaXaaCys can be present 1, 2, 3, 4, 5, 6, 7,
      8, or 9 times

<400> SEQUENCE: 17
```

Gly Gly Cys Xaa Xaa Cys
1               5

```
<210> SEQ ID NO 18
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 15, 16
<223> OTHER INFORMATION: Any Xaa positions are Pro, the remaining Xaa
      positions can be any amino acid

<400> SEQUENCE: 18
```

Glu Pro Lys Ser Xaa Asp Lys Thr His Thr Cys Xaa Xaa Cys Xaa Xaa
1               5                   10                  15

Cys

```
<210> SEQ ID NO 19
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 15, 16
<223> OTHER INFORMATION: At least one Xaa is Pro, the remaining Xaa
      positions can be any amino acid

<400> SEQUENCE: 19
```

Glu Pro Lys Ser Xaa Asp Lys Thr His Thr Cys Xaa Xaa Cys Xaa Xaa
1               5                   10                  15

Cys

```
<210> SEQ ID NO 20
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 13, 15, 16
<223> OTHER INFORMATION: Xaa can be any amino acid
<220> FEATURE:
<221> NAME/KEY: VARIANT
<222> LOCATION: 12
<223> OTHER INFORMATION: Xaa is Pro

<400> SEQUENCE: 20

Glu Pro Lys Ser Xaa Asp Lys Thr His Thr Cys Xaa Xaa Cys Xaa Xaa
1               5                   10                  15

Cys

<210> SEQ ID NO 21
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 15, 16
<223> OTHER INFORMATION: Xaa can be any amino acid
<220> FEATURE:
<221> NAME/KEY: VARIANT
<222> LOCATION: 13
<223> OTHER INFORMATION: Xaa is Pro

<400> SEQUENCE: 21

Glu Pro Lys Ser Xaa Asp Lys Thr His Thr Cys Xaa Xaa Cys Xaa Xaa
1               5                   10                  15

Cys

<210> SEQ ID NO 22
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 16
<223> OTHER INFORMATION: Xaa can be any amino acid
<220> FEATURE:
<221> NAME/KEY: VARIANT
<222> LOCATION: 15
<223> OTHER INFORMATION: Xaa is Pro

<400> SEQUENCE: 22

Glu Pro Lys Ser Xaa Asp Lys Thr His Thr Cys Xaa Xaa Cys Xaa Xaa
1               5                   10                  15

Cys

<210> SEQ ID NO 23
<211> LENGTH: 17
<212> TYPE: PRT
<213> ORGANISM: Artificial
<220> FEATURE:
<223> OTHER INFORMATION: Synthetic
<220> FEATURE:
```

```
<221> NAME/KEY: VARIANT
<222> LOCATION: 5, 12, 13, 15
<223> OTHER INFORMATION: Xaa can be any amino acid
<220> FEATURE:
<221> NAME/KEY: VARIANT
<222> LOCATION: 16
<223> OTHER INFORMATION: Xaa is Pro

<400> SEQUENCE: 23

Glu Pro Lys Ser Xaa Asp Lys Thr His Thr Cys Xaa Xaa Cys Xaa Xaa
1               5                   10                  15

Cys

<210> SEQ ID NO 24
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5
<223> OTHER INFORMATION: Xaa is Pro
<220> FEATURE:
<221> NAME/KEY: VARIANT
<222> LOCATION: 12, 13, 15, 16
<223> OTHER INFORMATION: Xaa can be any amino acid

<400> SEQUENCE: 24

Glu Pro Lys Ser Xaa Asp Lys Thr His Thr Cys Xaa Xaa Cys Xaa Xaa
1               5                   10                  15

Cys

<210> SEQ ID NO 25
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 15, 16
<223> OTHER INFORMATION: At least any two Xaa are Pro, the remaining Xaa
      positions can be any amino acid

<400> SEQUENCE: 25

Glu Pro Lys Ser Xaa Asp Lys Thr His Thr Cys Xaa Xaa Cys Xaa Xaa
1               5                   10                  15

Cys

<210> SEQ ID NO 26
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 15, 16
<223> OTHER INFORMATION: Xaa can be any amino acid
<220> FEATURE:
<221> NAME/KEY: VARIANT
<222> LOCATION: 12, 13
<223> OTHER INFORMATION: Xaa are Pro

<400> SEQUENCE: 26

Glu Pro Lys Ser Xaa Asp Lys Thr His Thr Cys Xaa Xaa Cys Xaa Xaa
1               5                   10                  15
```

Cys

<210> SEQ ID NO 27
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 13, 16
<223> OTHER INFORMATION: Xaa can be any amino acid
<220> FEATURE:
<221> NAME/KEY: VARIANT
<222> LOCATION: 12, 15
<223> OTHER INFORMATION: Xaa are Pro

<400> SEQUENCE: 27

Glu Pro Lys Ser Xaa Asp Lys Thr His Thr Cys Xaa Xaa Cys Xaa Xaa
1               5                   10                  15

Cys

<210> SEQ ID NO 28
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 13, 15
<223> OTHER INFORMATION: Xaa can be any amino acid
<220> FEATURE:
<221> NAME/KEY: VARIANT
<222> LOCATION: 12, 16
<223> OTHER INFORMATION: Xaa are Pro

<400> SEQUENCE: 28

Glu Pro Lys Ser Xaa Asp Lys Thr His Thr Cys Xaa Xaa Cys Xaa Xaa
1               5                   10                  15

Cys

<210> SEQ ID NO 29
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12
<223> OTHER INFORMATION: Xaa are Pro
<220> FEATURE:
<221> NAME/KEY: VARIANT
<222> LOCATION: 13, 15, 16
<223> OTHER INFORMATION: Xaa can be any amino acid

<400> SEQUENCE: 29

Glu Pro Lys Ser Xaa Asp Lys Thr His Thr Cys Xaa Xaa Cys Xaa Xaa
1               5                   10                  15

Cys

<210> SEQ ID NO 30
<211> LENGTH: 17
<212> TYPE: PRT
<213> ORGANISM: Artificial
<220> FEATURE:
<223> OTHER INFORMATION: Synthetic
<220> FEATURE:

<220> FEATURE:
<221> NAME/KEY: VARIANT
<222> LOCATION: 5, 12, 16
<223> OTHER INFORMATION: Xaa can be any amino acid
<220> FEATURE:
<221> NAME/KEY: VARIANT
<222> LOCATION: 13, 15
<223> OTHER INFORMATION: Xaa are Pro

<400> SEQUENCE: 30

Glu Pro Lys Ser Xaa Asp Lys Thr His Thr Cys Xaa Xaa Cys Xaa Xaa
1               5                   10                  15

Cys

<210> SEQ ID NO 31
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 15
<223> OTHER INFORMATION: Xaa can be any amino acid
<220> FEATURE:
<221> NAME/KEY: VARIANT
<222> LOCATION: 13, 16
<223> OTHER INFORMATION: Xaa are Pro

<400> SEQUENCE: 31

Glu Pro Lys Ser Xaa Asp Lys Thr His Thr Cys Xaa Xaa Cys Xaa Xaa
1               5                   10                  15

Cys

<210> SEQ ID NO 32
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 13
<223> OTHER INFORMATION: Xaa are Pro
<220> FEATURE:
<221> NAME/KEY: VARIANT
<222> LOCATION: 12, 15, 16
<223> OTHER INFORMATION: Xaa can be any amino acid

<400> SEQUENCE: 32

Glu Pro Lys Ser Xaa Asp Lys Thr His Thr Cys Xaa Xaa Cys Xaa Xaa
1               5                   10                  15

Cys

<210> SEQ ID NO 33
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13
<223> OTHER INFORMATION: Xaa can be any amino acid
<220> FEATURE:
<221> NAME/KEY: VARIANT
<222> LOCATION: 15, 16
<223> OTHER INFORMATION: Xaa are Pro

<400> SEQUENCE: 33

```
Glu Pro Lys Ser Xaa Asp Lys Thr His Thr Cys Xaa Xaa Cys Xaa Xaa
1               5                   10                  15

Cys
```

<210> SEQ ID NO 34
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 15
<223> OTHER INFORMATION: Xaa are Pro
<220> FEATURE:
<221> NAME/KEY: VARIANT
<222> LOCATION: 12, 13, 16
<223> OTHER INFORMATION: Xaa can be any amino acid

<400> SEQUENCE: 34

```
Glu Pro Lys Ser Xaa Asp Lys Thr His Thr Cys Xaa Xaa Cys Xaa Xaa
1               5                   10                  15

Cys
```

<210> SEQ ID NO 35
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 16
<223> OTHER INFORMATION: Xaa are Pro
<220> FEATURE:
<221> NAME/KEY: VARIANT
<222> LOCATION: 12, 13, 15
<223> OTHER INFORMATION: Xaa can be any amino acid

<400> SEQUENCE: 35

```
Glu Pro Lys Ser Xaa Asp Lys Thr His Thr Cys Xaa Xaa Cys Xaa Xaa
1               5                   10                  15

Cys
```

<210> SEQ ID NO 36
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 15, 16
<223> OTHER INFORMATION: At least any three Xaa are Pro, the remaining
      Xaa positions can be any amino acid

<400> SEQUENCE: 36

```
Glu Pro Lys Ser Xaa Asp Lys Thr His Thr Cys Xaa Xaa Cys Xaa Xaa
1               5                   10                  15

Cys
```

<210> SEQ ID NO 37
<211> LENGTH: 17
<212> TYPE: PRT
<213> ORGANISM: Artificial
<220> FEATURE:
<223> OTHER INFORMATION: Synthetic
<220> FEATURE:

```
<221> NAME/KEY: VARIANT
<222> LOCATION: 12, 13, 15
<223> OTHER INFORMATION: Xaa are Pro
<220> FEATURE:
<221> NAME/KEY: VARIANT
<222> LOCATION: 5, 16
<223> OTHER INFORMATION: Xaa can be any amino acid

<400> SEQUENCE: 37

Glu Pro Lys Ser Xaa Asp Lys Thr His Thr Cys Xaa Xaa Cys Xaa Xaa
1               5                   10                  15

Cys

<210> SEQ ID NO 38
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 13, 15, 16
<223> OTHER INFORMATION: Xaa are Pro
<220> FEATURE:
<221> NAME/KEY: VARIANT
<222> LOCATION: 5, 12
<223> OTHER INFORMATION: Xaa can be any amino acid

<400> SEQUENCE: 38

Glu Pro Lys Ser Xaa Asp Lys Thr His Thr Cys Xaa Xaa Cys Xaa Xaa
1               5                   10                  15

Cys

<210> SEQ ID NO 39
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 15, 16
<223> OTHER INFORMATION: Xaa are Pro
<220> FEATURE:
<221> NAME/KEY: VARIANT
<222> LOCATION: 12, 13
<223> OTHER INFORMATION: Xaa can be any amino acid

<400> SEQUENCE: 39

Glu Pro Lys Ser Xaa Asp Lys Thr His Thr Cys Xaa Xaa Cys Xaa Xaa
1               5                   10                  15

Cys

<210> SEQ ID NO 40
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 12, 13, 16
<223> OTHER INFORMATION: Xaa are Pro
<220> FEATURE:
<221> NAME/KEY: VARIANT
<222> LOCATION: 5, 15
<223> OTHER INFORMATION: Xaa can be any amino acid

<400> SEQUENCE: 40
```

Glu Pro Lys Ser Xaa Asp Lys Thr His Thr Cys Xaa Xaa Cys Xaa Xaa
1               5                   10                  15

Cys

<210> SEQ ID NO 41
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13
<223> OTHER INFORMATION: Xaa are Pro
<220> FEATURE:
<221> NAME/KEY: VARIANT
<222> LOCATION: 15, 16
<223> OTHER INFORMATION: Xaa can be any amino acid

<400> SEQUENCE: 41

Glu Pro Lys Ser Xaa Asp Lys Thr His Thr Cys Xaa Xaa Cys Xaa Xaa
1               5                   10                  15

Cys

<210> SEQ ID NO 42
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 12, 15, 16
<223> OTHER INFORMATION: Xaa are Pro
<220> FEATURE:
<221> NAME/KEY: VARIANT
<222> LOCATION: 5, 13
<223> OTHER INFORMATION: Xaa can be any amino acid

<400> SEQUENCE: 42

Glu Pro Lys Ser Xaa Asp Lys Thr His Thr Cys Xaa Xaa Cys Xaa Xaa
1               5                   10                  15

Cys

<210> SEQ ID NO 43
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 16
<223> OTHER INFORMATION: Xaa are Pro
<220> FEATURE:
<221> NAME/KEY: VARIANT
<222> LOCATION: 13, 15
<223> OTHER INFORMATION: Xaa can be any amino acid

<400> SEQUENCE: 43

Glu Pro Lys Ser Xaa Asp Lys Thr His Thr Cys Xaa Xaa Cys Xaa Xaa
1               5                   10                  15

Cys

<210> SEQ ID NO 44
<211> LENGTH: 17
<212> TYPE: PRT
<213> ORGANISM: Artificial

```
<220> FEATURE:
<223> OTHER INFORMATION: Synthetic
<220> FEATURE:
<221> NAME/KEY: VARIANT
<222> LOCATION: 5, 13, 15
<223> OTHER INFORMATION: Xaa are Pro
<220> FEATURE:
<221> NAME/KEY: VARIANT
<222> LOCATION: 12, 16
<223> OTHER INFORMATION: Xaa can be any amino acid

<400> SEQUENCE: 44

Glu Pro Lys Ser Xaa Asp Lys Thr His Thr Cys Xaa Xaa Cys Xaa Xaa
1               5                   10                  15

Cys

<210> SEQ ID NO 45
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 13, 16
<223> OTHER INFORMATION: Xaa are Pro
<220> FEATURE:
<221> NAME/KEY: VARIANT
<222> LOCATION: 12, 15
<223> OTHER INFORMATION: Xaa can be any amino acid

<400> SEQUENCE: 45

Glu Pro Lys Ser Xaa Asp Lys Thr His Thr Cys Xaa Xaa Cys Xaa Xaa
1               5                   10                  15

Cys

<210> SEQ ID NO 46
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 15
<223> OTHER INFORMATION: Xaa are Pro
<220> FEATURE:
<221> NAME/KEY: VARIANT
<222> LOCATION: 13, 16
<223> OTHER INFORMATION: Xaa can be any amino acid

<400> SEQUENCE: 46

Glu Pro Lys Ser Xaa Asp Lys Thr His Thr Cys Xaa Xaa Cys Xaa Xaa
1               5                   10                  15

Cys

<210> SEQ ID NO 47
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 15, 16
<223> OTHER INFORMATION: At least any four Xaa are Pro, the remaining
      Xaa positions can be any amino acid

<400> SEQUENCE: 47
```

Glu Pro Lys Ser Xaa Asp Lys Thr His Thr Cys Xaa Xaa Cys Xaa Xaa
1               5                   10                  15

Cys

<210> SEQ ID NO 48
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 12, 13, 15, 16
<223> OTHER INFORMATION: Xaa are Pro
<220> FEATURE:
<221> NAME/KEY: VARIANT
<222> LOCATION: 5
<223> OTHER INFORMATION: Xaa can be any amino acid

<400> SEQUENCE: 48

Glu Pro Lys Ser Xaa Asp Lys Thr His Thr Cys Xaa Xaa Cys Xaa Xaa
1               5                   10                  15

Cys

<210> SEQ ID NO 49
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 13, 15, 16
<223> OTHER INFORMATION: Xaa are Pro
<220> FEATURE:
<221> NAME/KEY: VARIANT
<222> LOCATION: 12
<223> OTHER INFORMATION: Xaa can be any amino acid

<400> SEQUENCE: 49

Glu Pro Lys Ser Xaa Asp Lys Thr His Thr Cys Xaa Xaa Cys Xaa Xaa
1               5                   10                  15

Cys

<210> SEQ ID NO 50
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 15, 16
<223> OTHER INFORMATION: Xaa are Pro
<220> FEATURE:
<221> NAME/KEY: VARIANT
<222> LOCATION: 13
<223> OTHER INFORMATION: Xaa can be any amino acid

<400> SEQUENCE: 50

Glu Pro Lys Ser Xaa Asp Lys Thr His Thr Cys Xaa Xaa Cys Xaa Xaa
1               5                   10                  15

Cys

<210> SEQ ID NO 51
<211> LENGTH: 17
<212> TYPE: PRT
<213> ORGANISM: Artificial

```
<220> FEATURE:
<223> OTHER INFORMATION: Synthetic
<220> FEATURE:
<221> NAME/KEY: VARIANT
<222> LOCATION: 5, 12, 13, 16
<223> OTHER INFORMATION: Xaa are Pro
<220> FEATURE:
<221> NAME/KEY: VARIANT
<222> LOCATION: 15
<223> OTHER INFORMATION: Xaa can be any amino acid

<400> SEQUENCE: 51

Glu Pro Lys Ser Xaa Asp Lys Thr His Thr Cys Xaa Xaa Cys Xaa Xaa
1               5                   10                  15

Cys

<210> SEQ ID NO 52
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 5, 12, 13, 15, 16
<223> OTHER INFORMATION: All Xaa are pro

<400> SEQUENCE: 52

Glu Pro Lys Ser Xaa Asp Lys Thr His Thr Cys Xaa Xaa Cys Xaa Xaa
1               5                   10                  15

Cys

<210> SEQ ID NO 53
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 9, 10
<223> OTHER INFORMATION: Any Xaa positions are Pro, the remaining Xaa
      positions can be any amino acid

<400> SEQUENCE: 53

Glu Arg Lys Xaa Cys Xaa Xaa Cys Xaa Xaa Cys
1               5                   10

<210> SEQ ID NO 54
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 9, 10
<223> OTHER INFORMATION: At least one Xaa is Pro, the remaining Xaa
      positions can be any amino acid

<400> SEQUENCE: 54

Glu Arg Lys Xaa Cys Xaa Xaa Cys Xaa Xaa Cys
1               5                   10

<210> SEQ ID NO 55
<211> LENGTH: 11
<212> TYPE: PRT
<213> ORGANISM: Artificial
<220> FEATURE:
```

```
<223> OTHER INFORMATION: Synthetic
<220> FEATURE:
<221> NAME/KEY: VARIANT
<222> LOCATION: 4, 7, 9, 10
<223> OTHER INFORMATION: Xaa can be any amino acid
<220> FEATURE:
<221> NAME/KEY: VARIANT
<222> LOCATION: 6
<223> OTHER INFORMATION: Xaa is Pro

<400> SEQUENCE: 55

Glu Arg Lys Xaa Cys Xaa Xaa Cys Xaa Xaa Cys
1               5                   10

<210> SEQ ID NO 56
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 7
<223> OTHER INFORMATION: Xaa is Pro
<220> FEATURE:
<221> NAME/KEY: VARIANT
<222> LOCATION: 4, 6, 9, 10
<223> OTHER INFORMATION: Xaa can be any amino acid

<400> SEQUENCE: 56

Glu Arg Lys Xaa Cys Xaa Xaa Cys Xaa Xaa Cys
1               5                   10

<210> SEQ ID NO 57
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9
<223> OTHER INFORMATION: Xaa is Pro
<220> FEATURE:
<221> NAME/KEY: VARIANT
<222> LOCATION: 4, 6, 7, 10
<223> OTHER INFORMATION: Xaa can be any amino acid

<400> SEQUENCE: 57

Glu Arg Lys Xaa Cys Xaa Xaa Cys Xaa Xaa Cys
1               5                   10

<210> SEQ ID NO 58
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 10
<223> OTHER INFORMATION: Xaa is Pro
<220> FEATURE:
<221> NAME/KEY: VARIANT
<222> LOCATION: 4, 6, 7, 9
<223> OTHER INFORMATION: Xaa can be any amino acid

<400> SEQUENCE: 58

Glu Arg Lys Xaa Cys Xaa Xaa Cys Xaa Xaa Cys
1               5                   10
```

```
<210> SEQ ID NO 59
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 9, 10
<223> OTHER INFORMATION: At least any two Xaa are Pro, the remaining Xaa
      positions can be any amino acid

<400> SEQUENCE: 59

Glu Arg Lys Xaa Cys Xaa Xaa Cys Xaa Xaa Cys
1               5                   10

<210> SEQ ID NO 60
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 6, 7
<223> OTHER INFORMATION: Xaa are Pro
<220> FEATURE:
<221> NAME/KEY: VARIANT
<222> LOCATION: 4, 9, 10
<223> OTHER INFORMATION: Xaa can be any amino acid

<400> SEQUENCE: 60

Glu Arg Lys Xaa Cys Xaa Xaa Cys Xaa Xaa Cys
1               5                   10

<210> SEQ ID NO 61
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 6, 9
<223> OTHER INFORMATION: Xaa are Pro
<220> FEATURE:
<221> NAME/KEY: VARIANT
<222> LOCATION: 4, 7, 10
<223> OTHER INFORMATION: Xaa can be any amino acid

<400> SEQUENCE: 61

Glu Arg Lys Xaa Cys Xaa Xaa Cys Xaa Xaa Cys
1               5                   10

<210> SEQ ID NO 62
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 6, 10
<223> OTHER INFORMATION: Xaa are Pro
<220> FEATURE:
<221> NAME/KEY: VARIANT
<222> LOCATION: 4, 7, 9
<223> OTHER INFORMATION: Xaa can be any amino acid

<400> SEQUENCE: 62

Glu Arg Lys Xaa Cys Xaa Xaa Cys Xaa Xaa Cys
1               5                   10
```

```
<210> SEQ ID NO 63
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6
<223> OTHER INFORMATION: Xaa are Pro
<220> FEATURE:
<221> NAME/KEY: VARIANT
<222> LOCATION: 7, 9, 10
<223> OTHER INFORMATION: Xaa can be any amino acid

<400> SEQUENCE: 63

Glu Arg Lys Xaa Cys Xaa Xaa Cys Xaa Xaa Cys
1               5                   10

<210> SEQ ID NO 64
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 7, 9
<223> OTHER INFORMATION: Xaa are Pro
<220> FEATURE:
<221> NAME/KEY: VARIANT
<222> LOCATION: 4, 6, 10
<223> OTHER INFORMATION: Xaa can be any amino acid

<400> SEQUENCE: 64

Glu Arg Lys Xaa Cys Xaa Xaa Cys Xaa Xaa Cys
1               5                   10

<210> SEQ ID NO 65
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 7, 10
<223> OTHER INFORMATION: Xaa are Pro
<220> FEATURE:
<221> NAME/KEY: VARIANT
<222> LOCATION: 4, 6, 9
<223> OTHER INFORMATION: Xaa can be any amino acid

<400> SEQUENCE: 65

Glu Arg Lys Xaa Cys Xaa Xaa Cys Xaa Xaa Cys
1               5                   10

<210> SEQ ID NO 66
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 7
<223> OTHER INFORMATION: Xaa are Pro
<220> FEATURE:
<221> NAME/KEY: VARIANT
<222> LOCATION: 6, 9, 10
<223> OTHER INFORMATION: Xaa can be any amino acid
```

<400> SEQUENCE: 66

Glu Arg Lys Xaa Cys Xaa Xaa Cys Xaa Xaa Cys
1               5                   10

<210> SEQ ID NO 67
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10
<223> OTHER INFORMATION: Xaa are Pro
<220> FEATURE:
<221> NAME/KEY: VARIANT
<222> LOCATION: 4, 6, 7
<223> OTHER INFORMATION: Xaa can be any amino acid

<400> SEQUENCE: 67

Glu Arg Lys Xaa Cys Xaa Xaa Cys Xaa Xaa Cys
1               5                   10

<210> SEQ ID NO 68
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 9
<223> OTHER INFORMATION: Xaa are Pro
<220> FEATURE:
<221> NAME/KEY: VARIANT
<222> LOCATION: 6, 7, 10
<223> OTHER INFORMATION: Xaa can be any amino acid

<400> SEQUENCE: 68

Glu Arg Lys Xaa Cys Xaa Xaa Cys Xaa Xaa Cys
1               5                   10

<210> SEQ ID NO 69
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 10
<223> OTHER INFORMATION: Xaa are Pro
<220> FEATURE:
<221> NAME/KEY: VARIANT
<222> LOCATION: 6, 7, 9
<223> OTHER INFORMATION: Xaa can be any amino acid

<400> SEQUENCE: 69

Glu Arg Lys Xaa Cys Xaa Xaa Cys Xaa Xaa Cys
1               5                   10

<210> SEQ ID NO 70
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 9, 10

```
<223> OTHER INFORMATION: At least any three Xaa are Pro, the remaining
      Xaa positions can be any amino acid

<400> SEQUENCE: 70

Glu Arg Lys Xaa Cys Xaa Xaa Cys Xaa Xaa Cys
1               5                   10

<210> SEQ ID NO 71
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 6, 7, 9
<223> OTHER INFORMATION: Xaa are Pro
<220> FEATURE:
<221> NAME/KEY: VARIANT
<222> LOCATION: 4, 10
<223> OTHER INFORMATION: Xaa can be any amino acid

<400> SEQUENCE: 71

Glu Arg Lys Xaa Cys Xaa Xaa Cys Xaa Xaa Cys
1               5                   10

<210> SEQ ID NO 72
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 7, 9, 10
<223> OTHER INFORMATION: Xaa are Pro
<220> FEATURE:
<221> NAME/KEY: VARIANT
<222> LOCATION: 4, 6
<223> OTHER INFORMATION: Xaa can be any amino acid

<400> SEQUENCE: 72

Glu Arg Lys Xaa Cys Xaa Xaa Cys Xaa Xaa Cys
1               5                   10

<210> SEQ ID NO 73
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 9, 10
<223> OTHER INFORMATION: Xaa are Pro
<220> FEATURE:
<221> NAME/KEY: VARIANT
<222> LOCATION: 6, 7
<223> OTHER INFORMATION: Xaa can be any amino acid

<400> SEQUENCE: 73

Glu Arg Lys Xaa Cys Xaa Xaa Cys Xaa Xaa Cys
1               5                   10

<210> SEQ ID NO 74
<211> LENGTH: 11
<212> TYPE: PRT
<213> ORGANISM: Artificial
<220> FEATURE:
<223> OTHER INFORMATION: Synthetic
<220> FEATURE:
```

```
<221> NAME/KEY: VARIANT
<222> LOCATION: 6, 7, 10
<223> OTHER INFORMATION: Xaa are Pro
<220> FEATURE:
<221> NAME/KEY: VARIANT
<222> LOCATION: 4, 9
<223> OTHER INFORMATION: Xaa can be any amino acid

<400> SEQUENCE: 74

Glu Arg Lys Xaa Cys Xaa Xaa Cys Xaa Xaa Cys
1               5                  10

<210> SEQ ID NO 75
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7
<223> OTHER INFORMATION: Xaa are Pro
<220> FEATURE:
<221> NAME/KEY: VARIANT
<222> LOCATION: 9, 10
<223> OTHER INFORMATION: Xaa can be any amino acid

<400> SEQUENCE: 75

Glu Arg Lys Xaa Cys Xaa Xaa Cys Xaa Xaa Cys
1               5                  10

<210> SEQ ID NO 76
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 6, 9, 10
<223> OTHER INFORMATION: Xaa are Pro
<220> FEATURE:
<221> NAME/KEY: VARIANT
<222> LOCATION: 4, 7
<223> OTHER INFORMATION: Xaa can be any amino acid

<400> SEQUENCE: 76

Glu Arg Lys Xaa Cys Xaa Xaa Cys Xaa Xaa Cys
1               5                  10

<210> SEQ ID NO 77
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 10
<223> OTHER INFORMATION: Xaa are Pro
<220> FEATURE:
<221> NAME/KEY: VARIANT
<222> LOCATION: 7, 9
<223> OTHER INFORMATION: Xaa can be any amino acid

<400> SEQUENCE: 77

Glu Arg Lys Xaa Cys Xaa Xaa Cys Xaa Xaa Cys
1               5                  10

<210> SEQ ID NO 78
<211> LENGTH: 11
```

```
-continued

<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 7, 9
<223> OTHER INFORMATION: Xaa are Pro
<220> FEATURE:
<221> NAME/KEY: VARIANT
<222> LOCATION: 6, 10
<223> OTHER INFORMATION: Xaa can be any amino acid

<400> SEQUENCE: 78

Glu Arg Lys Xaa Cys Xaa Xaa Cys Xaa Xaa Cys
1               5                   10

<210> SEQ ID NO 79
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 7, 10
<223> OTHER INFORMATION: Xaa are Pro
<220> FEATURE:
<221> NAME/KEY: VARIANT
<222> LOCATION: 6, 9
<223> OTHER INFORMATION: Xaa can be any amino acid

<400> SEQUENCE: 79

Glu Arg Lys Xaa Cys Xaa Xaa Cys Xaa Xaa Cys
1               5                   10

<210> SEQ ID NO 80
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 9
<223> OTHER INFORMATION: Xaa are Pro
<220> FEATURE:
<221> NAME/KEY: VARIANT
<222> LOCATION: 7, 10
<223> OTHER INFORMATION: Xaa can be any amino acid

<400> SEQUENCE: 80

Glu Arg Lys Xaa Cys Xaa Xaa Cys Xaa Xaa Cys
1               5                   10

<210> SEQ ID NO 81
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 9, 10
<223> OTHER INFORMATION: At least any four Xaa are Pro, the remaining
      Xaa positions can be any amino acid

<400> SEQUENCE: 81

Glu Arg Lys Xaa Cys Xaa Xaa Cys Xaa Xaa Cys
1               5                   10
```

```
<210> SEQ ID NO 82
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 6, 7, 9, 10
<223> OTHER INFORMATION: Xaa are Pro
<220> FEATURE:
<221> NAME/KEY: VARIANT
<222> LOCATION: 4
<223> OTHER INFORMATION: Xaa can be any amino acid

<400> SEQUENCE: 82

Glu Arg Lys Xaa Cys Xaa Xaa Cys Xaa Xaa Cys
1               5                   10

<210> SEQ ID NO 83
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 7, 9, 10
<223> OTHER INFORMATION: Xaa are Pro
<220> FEATURE:
<221> NAME/KEY: VARIANT
<222> LOCATION: 6
<223> OTHER INFORMATION: Xaa can be any amino acid

<400> SEQUENCE: 83

Glu Arg Lys Xaa Cys Xaa Xaa Cys Xaa Xaa Cys
1               5                   10

<210> SEQ ID NO 84
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 9, 10
<223> OTHER INFORMATION: Xaa are Pro
<220> FEATURE:
<221> NAME/KEY: VARIANT
<222> LOCATION: 7
<223> OTHER INFORMATION: Xaa can be any amino acid

<400> SEQUENCE: 84

Glu Arg Lys Xaa Cys Xaa Xaa Cys Xaa Xaa Cys
1               5                   10

<210> SEQ ID NO 85
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 10
<223> OTHER INFORMATION: Xaa are Pro
<220> FEATURE:
<221> NAME/KEY: VARIANT
<222> LOCATION: 9
<223> OTHER INFORMATION: Xaa can be any amino acid

<400> SEQUENCE: 85
```

```
Glu Arg Lys Xaa Cys Xaa Xaa Cys Xaa Xaa Cys
1               5                   10

<210> SEQ ID NO 86
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4, 6, 7, 9, 10
<223> OTHER INFORMATION: All Xaa are Pro

<400> SEQUENCE: 86

Glu Arg Lys Xaa Cys Xaa Xaa Cys Xaa Xaa Cys
1               5                   10

<210> SEQ ID NO 87
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 15, 17, 18
<223> OTHER INFORMATION: Any Xaa positions are Pro, the remaining Xaa
      positions can be any amino acid

<400> SEQUENCE: 87

Glu Leu Lys Thr Pro Leu Gly Asp Thr Thr His Thr Cys Xaa Xaa Cys
1               5                   10                  15

Xaa Xaa Cys

<210> SEQ ID NO 88
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 15, 17, 18
<223> OTHER INFORMATION: At least one Xaa is Pro, the remaining Xaa
      positions can be any amino acid

<400> SEQUENCE: 88

Glu Leu Lys Thr Pro Leu Gly Asp Thr Thr His Thr Cys Xaa Xaa Cys
1               5                   10                  15

Xaa Xaa Cys

<210> SEQ ID NO 89
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14
<223> OTHER INFORMATION: Xaa is Pro
<220> FEATURE:
<221> NAME/KEY: VARIANT
<222> LOCATION: 15, 17, 18
<223> OTHER INFORMATION: Xaa can be any amino acid

<400> SEQUENCE: 89
```

```
Glu Leu Lys Thr Pro Leu Gly Asp Thr Thr His Thr Cys Xaa Xaa Cys
1               5                   10                  15

Xaa Xaa Cys

<210> SEQ ID NO 90
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 15
<223> OTHER INFORMATION: Xaa is Pro
<220> FEATURE:
<221> NAME/KEY: VARIANT
<222> LOCATION: 14, 17, 18
<223> OTHER INFORMATION: Xaa can be any amino acid

<400> SEQUENCE: 90

Glu Leu Lys Thr Pro Leu Gly Asp Thr Thr His Thr Cys Xaa Xaa Cys
1               5                   10                  15

Xaa Xaa Cys

<210> SEQ ID NO 91
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 17
<223> OTHER INFORMATION: Xaa is Pro
<220> FEATURE:
<221> NAME/KEY: VARIANT
<222> LOCATION: 14, 15, 18
<223> OTHER INFORMATION: Xaa can be any amino acid

<400> SEQUENCE: 91

Glu Leu Lys Thr Pro Leu Gly Asp Thr Thr His Thr Cys Xaa Xaa Cys
1               5                   10                  15

Xaa Xaa Cys

<210> SEQ ID NO 92
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 18
<223> OTHER INFORMATION: Xaa is Pro
<220> FEATURE:
<221> NAME/KEY: VARIANT
<222> LOCATION: 14, 15, 17
<223> OTHER INFORMATION: Xaa can be any amino acid

<400> SEQUENCE: 92

Glu Leu Lys Thr Pro Leu Gly Asp Thr Thr His Thr Cys Xaa Xaa Cys
1               5                   10                  15

Xaa Xaa Cys

<210> SEQ ID NO 93
<211> LENGTH: 19
<212> TYPE: PRT
<213> ORGANISM: Artificial
```

```
<220> FEATURE:
<223> OTHER INFORMATION: Synthetic
<220> FEATURE:
<221> NAME/KEY: VARIANT
<222> LOCATION: 14, 15, 17, 18
<223> OTHER INFORMATION: At least any two Xaa are Pro, the remaining Xaa
      positions can be any amino acid

<400> SEQUENCE: 93

Glu Leu Lys Thr Pro Leu Gly Asp Thr Thr His Thr Cys Xaa Xaa Cys
1               5                   10                  15

Xaa Xaa Cys

<210> SEQ ID NO 94
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 15
<223> OTHER INFORMATION: Xaa are Pro
<220> FEATURE:
<221> NAME/KEY: VARIANT
<222> LOCATION: 17, 18
<223> OTHER INFORMATION: Xaa can be any amino acid

<400> SEQUENCE: 94

Glu Leu Lys Thr Pro Leu Gly Asp Thr Thr His Thr Cys Xaa Xaa Cys
1               5                   10                  15

Xaa Xaa Cys

<210> SEQ ID NO 95
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 17
<223> OTHER INFORMATION: Xaa are Pro
<220> FEATURE:
<221> NAME/KEY: VARIANT
<222> LOCATION: 15, 18
<223> OTHER INFORMATION: Xaa can be any amino acid

<400> SEQUENCE: 95

Glu Leu Lys Thr Pro Leu Gly Asp Thr Thr His Thr Cys Xaa Xaa Cys
1               5                   10                  15

Xaa Xaa Cys

<210> SEQ ID NO 96
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 18
<223> OTHER INFORMATION: Xaa are Pro
<220> FEATURE:
<221> NAME/KEY: VARIANT
<222> LOCATION: 15, 17
<223> OTHER INFORMATION: Xaa can be any amino acid

<400> SEQUENCE: 96
```

Glu Leu Lys Thr Pro Leu Gly Asp Thr Thr His Thr Cys Xaa Xaa Cys
1               5                   10                  15

Xaa Xaa Cys

<210> SEQ ID NO 97
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 15, 17
<223> OTHER INFORMATION: Xaa are Pro
<220> FEATURE:
<221> NAME/KEY: VARIANT
<222> LOCATION: 14, 18
<223> OTHER INFORMATION: Xaa can be any amino acid

<400> SEQUENCE: 97

Glu Leu Lys Thr Pro Leu Gly Asp Thr Thr His Thr Cys Xaa Xaa Cys
1               5                   10                  15

Xaa Xaa Cys

<210> SEQ ID NO 98
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 15, 18
<223> OTHER INFORMATION: Xaa are Pro
<220> FEATURE:
<221> NAME/KEY: VARIANT
<222> LOCATION: 14, 17
<223> OTHER INFORMATION: Xaa can be any amino acid

<400> SEQUENCE: 98

Glu Leu Lys Thr Pro Leu Gly Asp Thr Thr His Thr Cys Xaa Xaa Cys
1               5                   10                  15

Xaa Xaa Cys

<210> SEQ ID NO 99
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 17, 18
<223> OTHER INFORMATION: Xaa are Pro
<220> FEATURE:
<221> NAME/KEY: VARIANT
<222> LOCATION: 14, 15
<223> OTHER INFORMATION: Xaa can be any amino acid

<400> SEQUENCE: 99

Glu Leu Lys Thr Pro Leu Gly Asp Thr Thr His Thr Cys Xaa Xaa Cys
1               5                   10                  15

Xaa Xaa Cys

<210> SEQ ID NO 100
<211> LENGTH: 19
<212> TYPE: PRT
<213> ORGANISM: Artificial

```
<220> FEATURE:
<223> OTHER INFORMATION: Synthetic
<220> FEATURE:
<221> NAME/KEY: VARIANT
<222> LOCATION: 14, 15, 17, 18
<223> OTHER INFORMATION: At least any three Xaa are Pro, the remaining
      Xaa positions can be any amino acid

<400> SEQUENCE: 100

Glu Leu Lys Thr Pro Leu Gly Asp Thr Thr His Thr Cys Xaa Xaa Cys
1               5                   10                  15

Xaa Xaa Cys

<210> SEQ ID NO 101
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 15, 17
<223> OTHER INFORMATION: Xaa are Pro
<220> FEATURE:
<221> NAME/KEY: VARIANT
<222> LOCATION: 18
<223> OTHER INFORMATION: Xaa can be any amino acid

<400> SEQUENCE: 101

Glu Leu Lys Thr Pro Leu Gly Asp Thr Thr His Thr Cys Xaa Xaa Cys
1               5                   10                  15

Xaa Xaa Cys

<210> SEQ ID NO 102
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 15, 18
<223> OTHER INFORMATION: Xaa are Pro
<220> FEATURE:
<221> NAME/KEY: VARIANT
<222> LOCATION: 17
<223> OTHER INFORMATION: Xaa can be any amino acid

<400> SEQUENCE: 102

Glu Leu Lys Thr Pro Leu Gly Asp Thr Thr His Thr Cys Xaa Xaa Cys
1               5                   10                  15

Xaa Xaa Cys

<210> SEQ ID NO 103
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 17, 18
<223> OTHER INFORMATION: Xaa are Pro
<220> FEATURE:
<221> NAME/KEY: VARIANT
<222> LOCATION: 15
<223> OTHER INFORMATION: Xaa can be any amino acid

<400> SEQUENCE: 103
```

```
Glu Leu Lys Thr Pro Leu Gly Asp Thr Thr His Thr Cys Xaa Xaa Cys
1               5                   10                  15

Xaa Xaa Cys

<210> SEQ ID NO 104
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 15, 17, 18
<223> OTHER INFORMATION: Xaa are Pro
<220> FEATURE:
<221> NAME/KEY: VARIANT
<222> LOCATION: 14
<223> OTHER INFORMATION: Xaa can be any amino acid

<400> SEQUENCE: 104

Glu Leu Lys Thr Pro Leu Gly Asp Thr Thr His Thr Cys Xaa Xaa Cys
1               5                   10                  15

Xaa Xaa Cys

<210> SEQ ID NO 105
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 14, 15, 17, 18
<223> OTHER INFORMATION: All Xaa are Pro

<400> SEQUENCE: 105

Glu Leu Lys Thr Pro Leu Gly Asp Thr Thr His Thr Cys Xaa Xaa Cys
1               5                   10                  15

Xaa Xaa Cys

<210> SEQ ID NO 106
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10, 12, 13
<223> OTHER INFORMATION: Any Xaa positions are Pro, the remaining Xaa
      positions can be any amino acid

<400> SEQUENCE: 106

Glu Ser Lys Tyr Gly Pro Pro Cys Xaa Xaa Cys Xaa Xaa Cys
1               5                   10

<210> SEQ ID NO 107
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10, 12, 13
<223> OTHER INFORMATION: At least one Xaa is Pro, the remaining Xaa
      positions can be any amino acid

<400> SEQUENCE: 107
```

Glu Ser Lys Tyr Gly Pro Pro Cys Xaa Xaa Cys Xaa Xaa Cys
1               5                   10

<210> SEQ ID NO 108
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9
<223> OTHER INFORMATION: Xaa is Pro
<220> FEATURE:
<221> NAME/KEY: VARIANT
<222> LOCATION: 10, 12, 13
<223> OTHER INFORMATION: Xaa can be any amino acid

<400> SEQUENCE: 108

Glu Ser Lys Tyr Gly Pro Pro Cys Xaa Xaa Cys Xaa Xaa Cys
1               5                   10

<210> SEQ ID NO 109
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 10
<223> OTHER INFORMATION: Xaa is Pro
<220> FEATURE:
<221> NAME/KEY: VARIANT
<222> LOCATION: 9, 12, 13
<223> OTHER INFORMATION: Xaa can be any amino acid

<400> SEQUENCE: 109

Glu Ser Lys Tyr Gly Pro Pro Cys Xaa Xaa Cys Xaa Xaa Cys
1               5                   10

<210> SEQ ID NO 110
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 12
<223> OTHER INFORMATION: Xaa is Pro
<220> FEATURE:
<221> NAME/KEY: VARIANT
<222> LOCATION: 9, 10, 13
<223> OTHER INFORMATION: Xaa can be any amino acid

<400> SEQUENCE: 110

Glu Ser Lys Tyr Gly Pro Pro Cys Xaa Xaa Cys Xaa Xaa Cys
1               5                   10

<210> SEQ ID NO 111
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 13
<223> OTHER INFORMATION: Xaa is Pro
<220> FEATURE:

```
<221> NAME/KEY: VARIANT
<222> LOCATION: 9, 10, 12
<223> OTHER INFORMATION: Xaa can be any amino acid

<400> SEQUENCE: 111

Glu Ser Lys Tyr Gly Pro Pro Cys Xaa Xaa Cys Xaa Xaa Cys
1               5                   10

<210> SEQ ID NO 112
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10, 12, 13
<223> OTHER INFORMATION: At least any two Xaa are Pro, the remaining Xaa
      positions can be any amino acid

<400> SEQUENCE: 112

Glu Ser Lys Tyr Gly Pro Pro Cys Xaa Xaa Cys Xaa Xaa Cys
1               5                   10

<210> SEQ ID NO 113
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10
<223> OTHER INFORMATION: Xaa are Pro
<220> FEATURE:
<221> NAME/KEY: VARIANT
<222> LOCATION: 12, 13
<223> OTHER INFORMATION: Xaa can be any amino acid

<400> SEQUENCE: 113

Glu Ser Lys Tyr Gly Pro Pro Cys Xaa Xaa Cys Xaa Xaa Cys
1               5                   10

<210> SEQ ID NO 114
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 12
<223> OTHER INFORMATION: Xaa are Pro
<220> FEATURE:
<221> NAME/KEY: VARIANT
<222> LOCATION: 10, 13
<223> OTHER INFORMATION: Xaa can be any amino acid

<400> SEQUENCE: 114

Glu Ser Lys Tyr Gly Pro Pro Cys Xaa Xaa Cys Xaa Xaa Cys
1               5                   10

<210> SEQ ID NO 115
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 13
```

```
<223> OTHER INFORMATION: Xaa are Pro
<220> FEATURE:
<221> NAME/KEY: VARIANT
<222> LOCATION: 10, 12
<223> OTHER INFORMATION: Xaa can be any amino acid

<400> SEQUENCE: 115

Glu Ser Lys Tyr Gly Pro Pro Cys Xaa Xaa Cys Xaa Xaa Cys
1               5                   10

<210> SEQ ID NO 116
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 10, 12
<223> OTHER INFORMATION: Xaa are Pro
<220> FEATURE:
<221> NAME/KEY: VARIANT
<222> LOCATION: 9, 13
<223> OTHER INFORMATION: Xaa can be any amino acid

<400> SEQUENCE: 116

Glu Ser Lys Tyr Gly Pro Pro Cys Xaa Xaa Cys Xaa Xaa Cys
1               5                   10

<210> SEQ ID NO 117
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 10, 13
<223> OTHER INFORMATION: Xaa are Pro
<220> FEATURE:
<221> NAME/KEY: VARIANT
<222> LOCATION: 9, 12
<223> OTHER INFORMATION: Xaa can be any amino acid

<400> SEQUENCE: 117

Glu Ser Lys Tyr Gly Pro Pro Cys Xaa Xaa Cys Xaa Xaa Cys
1               5                   10

<210> SEQ ID NO 118
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 12, 13
<223> OTHER INFORMATION: Xaa are Pro
<220> FEATURE:
<221> NAME/KEY: VARIANT
<222> LOCATION: 9, 10
<223> OTHER INFORMATION: Xaa can be any amino acid

<400> SEQUENCE: 118

Glu Ser Lys Tyr Gly Pro Pro Cys Xaa Xaa Cys Xaa Xaa Cys
1               5                   10

<210> SEQ ID NO 119
<211> LENGTH: 14
<212> TYPE: PRT
<213> ORGANISM: Artificial
```

```
<220> FEATURE:
<223> OTHER INFORMATION: Synthetic
<220> FEATURE:
<221> NAME/KEY: VARIANT
<222> LOCATION: 9, 10, 12, 13
<223> OTHER INFORMATION: At least any three Xaa are Pro, the remaining
      Xaa positions can be any amino acid

<400> SEQUENCE: 119

Glu Ser Lys Tyr Gly Pro Pro Cys Xaa Xaa Cys Xaa Xaa Cys
1               5                   10

<210> SEQ ID NO 120
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10, 12
<223> OTHER INFORMATION: Xaa are Pro
<220> FEATURE:
<221> NAME/KEY: VARIANT
<222> LOCATION: 13
<223> OTHER INFORMATION: Xaa can be any amino acid

<400> SEQUENCE: 120

Glu Ser Lys Tyr Gly Pro Pro Cys Xaa Xaa Cys Xaa Xaa Cys
1               5                   10

<210> SEQ ID NO 121
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10, 13
<223> OTHER INFORMATION: Xaa are Pro
<220> FEATURE:
<221> NAME/KEY: VARIANT
<222> LOCATION: 12
<223> OTHER INFORMATION: Xaa can be any amino acid

<400> SEQUENCE: 121

Glu Ser Lys Tyr Gly Pro Pro Cys Xaa Xaa Cys Xaa Xaa Cys
1               5                   10

<210> SEQ ID NO 122
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 12, 13
<223> OTHER INFORMATION: Xaa are Pro
<220> FEATURE:
<221> NAME/KEY: VARIANT
<222> LOCATION: 10
<223> OTHER INFORMATION: Xaa can be any amino acid

<400> SEQUENCE: 122

Glu Ser Lys Tyr Gly Pro Pro Cys Xaa Xaa Cys Xaa Xaa Cys
1               5                   10

<210> SEQ ID NO 123
<211> LENGTH: 14
```

```
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 10, 12, 13
<223> OTHER INFORMATION: Xaa are Pro
<220> FEATURE:
<221> NAME/KEY: VARIANT
<222> LOCATION: 9
<223> OTHER INFORMATION: Xaa can be any amino acid

<400> SEQUENCE: 123

Glu Ser Lys Tyr Gly Pro Pro Cys Xaa Xaa Cys Xaa Xaa Cys
1               5                   10

<210> SEQ ID NO 124
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 9, 10, 12, 13
<223> OTHER INFORMATION: All Xaa are Pro

<400> SEQUENCE: 124

Glu Ser Lys Tyr Gly Pro Pro Cys Xaa Xaa Cys Xaa Xaa Cys
1               5                   10

<210> SEQ ID NO 125
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6
<223> OTHER INFORMATION: Any one Xaa positions are Pro

<400> SEQUENCE: 125

Cys Xaa Xaa Cys Xaa Xaa Cys
1               5

<210> SEQ ID NO 126
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6
<223> OTHER INFORMATION: Any two Xaa are Pro

<400> SEQUENCE: 126

Cys Xaa Xaa Cys Xaa Xaa Cys
1               5

<210> SEQ ID NO 127
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6
```

```
<223> OTHER INFORMATION: Any three Xaa are Pro

<400> SEQUENCE: 127

Cys Xaa Xaa Cys Xaa Xaa Cys
1               5

<210> SEQ ID NO 128
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9
<223> OTHER INFORMATION: Any one Xaa positions are Pro

<400> SEQUENCE: 128

Cys Xaa Xaa Cys Xaa Xaa Cys Xaa Xaa Cys
1               5                   10

<210> SEQ ID NO 129
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9
<223> OTHER INFORMATION: Any two Xaa are Pro

<400> SEQUENCE: 129

Cys Xaa Xaa Cys Xaa Xaa Cys Xaa Xaa Cys
1               5                   10

<210> SEQ ID NO 130
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9
<223> OTHER INFORMATION: Any three Xaa are Pro

<400> SEQUENCE: 130

Cys Xaa Xaa Cys Xaa Xaa Cys Xaa Xaa Cys
1               5                   10

<210> SEQ ID NO 131
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9
<223> OTHER INFORMATION: Any four Xaa are Pro

<400> SEQUENCE: 131

Cys Xaa Xaa Cys Xaa Xaa Cys Xaa Xaa Cys
1               5                   10

<210> SEQ ID NO 132
<211> LENGTH: 10
<212> TYPE: PRT
```

```
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9
<223> OTHER INFORMATION: Any five Xaa are Pro

<400> SEQUENCE: 132

Cys Xaa Xaa Cys Xaa Xaa Cys Xaa Xaa Cys
1               5                   10

<210> SEQ ID NO 133
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Any one Xaa positions are Pro

<400> SEQUENCE: 133

Cys Xaa Xaa Cys Xaa Xaa Cys Xaa Xaa Cys Xaa Xaa Cys
1               5                   10

<210> SEQ ID NO 134
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Any two Xaa are Pro

<400> SEQUENCE: 134

Cys Xaa Xaa Cys Xaa Xaa Cys Xaa Xaa Cys Xaa Xaa Cys
1               5                   10

<210> SEQ ID NO 135
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Any three Xaa are Pro

<400> SEQUENCE: 135

Cys Xaa Xaa Cys Xaa Xaa Cys Xaa Xaa Cys Xaa Xaa Cys
1               5                   10

<210> SEQ ID NO 136
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Any four Xaa are Pro

<400> SEQUENCE: 136

Cys Xaa Xaa Cys Xaa Xaa Cys Xaa Xaa Cys Xaa Xaa Cys
```

<210> SEQ ID NO 137
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Any five Xaa are Pro

<400> SEQUENCE: 137

Cys Xaa Xaa Cys Xaa Xaa Cys Xaa Xaa Cys Xaa Xaa Cys
1               5                   10

<210> SEQ ID NO 138
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Any six Xaa are Pro

<400> SEQUENCE: 138

Cys Xaa Xaa Cys Xaa Xaa Cys Xaa Xaa Cys Xaa Xaa Cys
1               5                   10

<210> SEQ ID NO 139
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12
<223> OTHER INFORMATION: Any seven Xaa are Pro

<400> SEQUENCE: 139

Cys Xaa Xaa Cys Xaa Xaa Cys Xaa Xaa Cys Xaa Xaa Cys
1               5                   10

<210> SEQ ID NO 140
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any one Xaa positions are Pro

<400> SEQUENCE: 140

Cys Xaa Xaa Cys Xaa Xaa Cys Xaa Xaa Cys Xaa Xaa Cys Xaa Xaa Cys
1               5                   10                  15

<210> SEQ ID NO 141
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any two Xaa are Pro

<400> SEQUENCE: 141

Cys Xaa Xaa Cys Xaa Xaa Cys Xaa Xaa Cys Xaa Xaa Cys Xaa Xaa Cys
1               5                   10                  15

<210> SEQ ID NO 142
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any three Xaa are Pro

<400> SEQUENCE: 142

Cys Xaa Xaa Cys Xaa Xaa Cys Xaa Xaa Cys Xaa Xaa Cys Xaa Xaa Cys
1               5                   10                  15

<210> SEQ ID NO 143
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any four Xaa are Pro

<400> SEQUENCE: 143

Cys Xaa Xaa Cys Xaa Xaa Cys Xaa Xaa Cys Xaa Xaa Cys Xaa Xaa Cys
1               5                   10                  15

<210> SEQ ID NO 144
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any five Xaa are Pro

<400> SEQUENCE: 144

Cys Xaa Xaa Cys Xaa Xaa Cys Xaa Xaa Cys Xaa Xaa Cys Xaa Xaa Cys
1               5                   10                  15

<210> SEQ ID NO 145
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any six Xaa are Pro

<400> SEQUENCE: 145

Cys Xaa Xaa Cys Xaa Xaa Cys Xaa Xaa Cys Xaa Xaa Cys Xaa Xaa Cys
1               5                   10                  15

<210> SEQ ID NO 146
<211> LENGTH: 16

```
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any seven Xaa are Pro

<400> SEQUENCE: 146

Cys Xaa Xaa Cys Xaa Xaa Cys Xaa Xaa Cys Xaa Xaa Cys Xaa Xaa Cys
1               5                   10                  15

<210> SEQ ID NO 147
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any eight Xaa are Pro

<400> SEQUENCE: 147

Cys Xaa Xaa Cys Xaa Xaa Cys Xaa Xaa Cys Xaa Xaa Cys Xaa Xaa Cys
1               5                   10                  15

<210> SEQ ID NO 148
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15
<223> OTHER INFORMATION: Any nine Xaa are Pro

<400> SEQUENCE: 148

Cys Xaa Xaa Cys Xaa Xaa Cys Xaa Xaa Cys Xaa Xaa Cys Xaa Xaa Cys
1               5                   10                  15

<210> SEQ ID NO 149
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any one Xaa positions are Pro

<400> SEQUENCE: 149

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 150
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any two Xaa are Pro
```

-continued

<400> SEQUENCE: 150

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 151
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any three Xaa are Pro

<400> SEQUENCE: 151

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 152
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any four Xaa are Pro

<400> SEQUENCE: 152

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 153
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any five Xaa are Pro

<400> SEQUENCE: 153

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 154
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any six Xaa are Pro

<400> SEQUENCE: 154

Cys Xaa Xaa Cys Xaa Xaa Cys Xaa Xaa Cys Xaa Xaa Cys Xaa Xaa Cys

```
1               5                   10                  15

Xaa Xaa Cys

<210> SEQ ID NO 155
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any seven Xaa are Pro

<400> SEQUENCE: 155

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 156
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any eight Xaa are Pro

<400> SEQUENCE: 156

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 157
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any nine Xaa are Pro

<400> SEQUENCE: 157

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 158
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any ten Xaa are Pro

<400> SEQUENCE: 158

Cys Xaa Xaa Cys Xaa Xaa Cys Xaa Xaa Cys Xaa Xaa Cys Xaa Xaa Cys
1               5                   10                  15

Xaa Xaa Cys
```

<210> SEQ ID NO 159
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 2, 3, 5, 6, 8, 9, 11, 12, 14, 15, 17, 18
<223> OTHER INFORMATION: Any eleven Xaa are Pro

<400> SEQUENCE: 159

Cys Xaa Xaa Cys Xaa Xaa Cys Xaa Xaa Cys Xaa Xaa Cys Xaa Xaa Cys
1               5                   10                  15

Xaa Xaa Cys

<210> SEQ ID NO 160
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: VARIANT
<222> LOCATION: 4
<223> OTHER INFORMATION: Xaa is Pro
<220> FEATURE:
<221> NAME/KEY: VARIANT
<222> LOCATION: 6, 7, 9, 10
<223> OTHER INFORMATION: Xaa can be any amino acid

<400> SEQUENCE: 160

Glu Arg Lys Xaa Cys Xaa Xaa Cys Xaa Xaa Cys
1               5                   10

<210> SEQ ID NO 161
<211> LENGTH: 236
<212> TYPE: PRT
<213> ORGANISM: Artificial
<220> FEATURE:
<223> OTHER INFORMATION: Synthetic

<400> SEQUENCE: 161

Asp Val Gln Ile Thr Gln Ser Pro Ser Ser Leu Ser Ala Ser Val Gly
1               5                   10                  15

Asp Arg Val Thr Ile Thr Cys Arg Thr Ser Arg Ser Ile Ser Gln Tyr
                20                  25                  30

Leu Ala Trp Tyr Gln Gln Lys Pro Gly Lys Val Pro Lys Leu Leu Ile
            35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Asn Pro Leu
                85                  90                  95

Thr Phe Gly Gly Gly Thr Lys Val Glu Ile Lys Gly Gly Ser Gly
            100                 105                 110

Gly Gly Gly Glu Val Gln Leu Val Glu Ser Gly Gly Leu Val Gln
            115                 120                 125

Pro Gly Gly Ser Leu Arg Leu Ser Cys Ala Ala Ser Gly Phe Asn Ile
            130                 135                 140

Lys Asp Thr Tyr Ile His Phe Val Arg Gln Ala Pro Gly Lys Gly Leu

```
145                 150                 155                 160
Glu Trp Ile Gly Arg Ile Asp Pro Ala Asn Asp Asn Thr Leu Tyr Ala
                165                 170                 175
Ser Lys Phe Gln Gly Lys Ala Thr Ile Ser Ala Asp Thr Ser Lys Asn
                180                 185                 190
Thr Ala Tyr Leu Gln Met Asn Ser Leu Arg Ala Glu Asp Thr Ala Val
                195                 200                 205
Tyr Tyr Cys Gly Arg Gly Tyr Gly Tyr Val Phe Asp His Trp Gly
        210                 215                 220
Gln Gly Thr Leu Val Thr Val Ser Ser Gly Gly Cys
225                 230                 235

<210> SEQ ID NO 162
<211> LENGTH: 236
<212> TYPE: PRT
<213> ORGANISM: Artificial
<220> FEATURE:
<223> OTHER INFORMATION: Synthetic

<400> SEQUENCE: 162

Asp Val Gln Ile Thr Gln Ser Pro Ser Ser Leu Ser Ala Ser Val Gly
1               5                   10                  15
Asp Arg Val Thr Ile Thr Cys Arg Thr Ser Arg Ser Ile Ser Gln Tyr
                20                  25                  30
Leu Ala Trp Tyr Gln Gln Lys Pro Gly Lys Val Pro Lys Leu Leu Ile
            35                  40                  45
Tyr Ser Gly Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Gln His Asn Glu Asn Pro Leu
                85                  90                  95
Thr Phe Gly Gly Gly Thr Lys Val Glu Ile Lys Ser Gly Gly Gly Gly
                100                 105                 110
Glu Val Gln Leu Val Glu Ser Gly Gly Gly Leu Val Gln Pro Gly Gly
            115                 120                 125
Ser Leu Arg Leu Ser Cys Ala Ala Ser Gly Phe Asn Ile Lys Asp Thr
130                 135                 140
Tyr Ile His Phe Val Arg Gln Ala Pro Gly Lys Gly Leu Glu Trp Ile
145                 150                 155                 160
Gly Arg Ile Asp Pro Ala Asn Asp Asn Thr Leu Tyr Ala Ser Lys Phe
                165                 170                 175
Gln Gly Lys Ala Thr Ile Ser Ala Asp Thr Ser Lys Asn Thr Ala Tyr
                180                 185                 190
Leu Gln Met Asn Ser Leu Arg Ala Glu Asp Thr Ala Val Tyr Tyr Cys
            195                 200                 205
Gly Arg Gly Tyr Gly Tyr Val Phe Asp His Trp Gly Gln Gly Thr
        210                 215                 220
Leu Val Thr Val Ser Ser Gly Gly Cys Pro Pro Cys
225                 230                 235

<210> SEQ ID NO 163
<211> LENGTH: 239
<212> TYPE: PRT
<213> ORGANISM: Artificial
<220> FEATURE:
<223> OTHER INFORMATION: Synthetic
```

```
<400> SEQUENCE: 163

Asp Val Gln Ile Thr Gln Ser Pro Ser Ser Leu Ser Ala Ser Val Gly
1               5                   10                  15

Asp Arg Val Thr Ile Thr Cys Arg Thr Ser Arg Ser Ile Ser Gln Tyr
                20                  25                  30

Leu Ala Trp Tyr Gln Gln Lys Pro Gly Lys Val Pro Lys Leu Leu Ile
            35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Asn Pro Leu
                85                  90                  95

Thr Phe Gly Gly Gly Thr Lys Val Glu Ile Lys Ser Gly Gly Gly Gly
                100                 105                 110

Glu Val Gln Leu Val Glu Ser Gly Gly Gly Leu Val Gln Pro Gly Gly
            115                 120                 125

Ser Leu Arg Leu Ser Cys Ala Ala Ser Gly Phe Asn Ile Lys Asp Thr
130                 135                 140

Tyr Ile His Phe Val Arg Gln Ala Pro Gly Lys Gly Leu Glu Trp Ile
145             150                 155                 160

Gly Arg Ile Asp Pro Ala Asn Asp Asn Thr Leu Tyr Ala Ser Lys Phe
                165                 170                 175

Gln Gly Lys Ala Thr Ile Ser Ala Asp Thr Ser Lys Asn Thr Ala Tyr
            180                 185                 190

Leu Gln Met Asn Ser Leu Arg Ala Glu Asp Thr Ala Val Tyr Tyr Cys
            195                 200                 205

Gly Arg Gly Tyr Gly Tyr Tyr Val Phe Asp His Trp Gly Gln Gly Thr
            210                 215                 220

Leu Val Thr Val Ser Ser Gly Gly Cys Pro Pro Cys Pro Pro Cys
225                 230                 235
```

UNITED STATES PATENT AND TRADEMARK OFFICE
CERTIFICATE OF CORRECTION

| | | |
|---|---|---|
| PATENT NO. | : 11,266,745 B2 | Page 1 of 1 |
| APPLICATION NO. | : 15/866870 | |
| DATED | : March 8, 2022 | |
| INVENTOR(S) | : Gudas et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this
Twelfth Day of December, 2023

*Katherine Kelly Vidal*

Katherine Kelly Vidal
*Director of the United States Patent and Trademark Office*